(12) United States Patent
Lu et al.

(10) Patent No.: US 12,409,161 B2
(45) Date of Patent: Sep. 9, 2025

(54) COMPOUND FOR TREATING NEURODEGENERATIVE DISORDERS

(71) Applicant: FUDAN UNIVERSITY, Shanghai (CN)

(72) Inventors: Boxun Lu, Shanghai (CN); Yiyan Fei, Shanghai (CN); Yu Ding, Shanghai (CN); Yongjun Dang, Shanghai (CN)

(73) Assignee: Fudan University, Shanghai (CN)

( * ) Notice: Subject to any disclaimer, the term of this patent is extended or adjusted under 35 U.S.C. 154(b) by 1032 days.

(21) Appl. No.: 17/437,976

(22) PCT Filed: Mar. 11, 2020

(86) PCT No.: PCT/CN2020/078779
§ 371 (c)(1),
(2) Date: Sep. 10, 2021

(87) PCT Pub. No.: WO2020/182144
PCT Pub. Date: Sep. 17, 2020

(65) Prior Publication Data
US 2022/0249433 A1  Aug. 11, 2022

(30) Foreign Application Priority Data

Mar. 11, 2019 (CN) .......................... 201910180674.7
Oct. 21, 2019 (CN) .......................... 201911000198.2

(51) Int. Cl.
*A61K 31/353* (2006.01)
*A61K 31/352* (2006.01)
*A61K 31/517* (2006.01)
*A61P 25/00* (2006.01)
*C07D 311/20* (2006.01)
*C07D 311/22* (2006.01)

(52) U.S. Cl.
CPC .......... *A61K 31/353* (2013.01); *A61K 31/517* (2013.01); *A61P 25/00* (2018.01)

(58) Field of Classification Search
CPC ..... A61K 31/353; A61K 31/352; A61P 25/00; C07D 311/20; C07D 311/22
See application file for complete search history.

(56) References Cited

FOREIGN PATENT DOCUMENTS

| | | |
|---|---|---|
| CN | 102499917 A | 6/2012 |
| WO | 2008021210 A2 | 2/2008 |
| WO | 2010/011964 A2 | 1/2010 |
| WO | 2010/047674 A1 | 4/2010 |
| WO | 2010/056758 A1 | 5/2010 |
| WO | 2010/075286 A1 | 7/2010 |
| WO | 2013/061279 A1 | 5/2013 |
| WO | 2018203559 A1 | 11/2018 |

OTHER PUBLICATIONS

Li et al., Allele-selective lowering of mutant HTT protein by HTT-LC3 linker compounds, Nature, vol. 575, No. 7781, pp. 203-209 (Year: 2019).*
Extended European Search Report issued Mar. 24, 2023 in EP Application No. 20771013.8.
Herbst, Martin, et al., "Therapeutic approaches to polyglutamine diseases: Combating protein misfolding and aggregation," Current Pharmaceutical Design, Bentham Science Publishers, NL, vol. 12, No. 20, pp. 2543-2555, Jul. 1, 2006.
Li et al., Discovery and optimization of novel 3-piperazinylcoumarin antagonist of chemokine-like factor 1 with oral antiasthma activity in mice. J Med Chem. Feb. 25, 2010;53(4):1741-54.
International Search Report and Written Opinion for Application No. PCT/CN2020/078779, dated Jun. 11, 2020, 16 pages.

* cited by examiner

*Primary Examiner* — Brenda L Coleman
(74) *Attorney, Agent, or Firm* — IceMiller LLP

(57) ABSTRACT

The present invention relates to use of a compound with a substituted bicyclic structure, a pharmaceutically acceptable salt, stereoisomer, solvate, polymorph, tautomer, isotopic compound, metabolite or prodrug thereof in the preparation of a medicament for preventing or treating polyglutamine (polyQ) related disorders.

6 Claims, 9 Drawing Sheets
Specification includes a Sequence Listing.

t=4.41,df=11   t=1.35,df=11

SEQUENCE LISTING

<160> NUMBER OF SEQ ID NOS: 5

<210> SEQ ID NO 1
<211> LENGTH: 261
<212> TYPE: PRT
<213> ORGANISM: Homo sapiens
<220> FEATURE:
<223> OTHER INFORMATION: Q25-GFP

<400> SEQUENCE: 1

```
Met Gln Gln Gln Gln Gln Gln Gln Gln Gln Gln Gln Gln
1               5                   10                  15

Gln Gln Gln Gln Gln Gln Gln Gln Gln Met Ser Lys Gly Glu Glu
            20                  25                  30

Leu Phe Thr Gly Val Val Pro Ile Leu Val Glu Leu Asp Gly Asp Val
            35                  40                  45

Asn Gly His Lys Phe Ser Val Arg Gly Glu Gly Glu Gly Asp Ala Thr
50                  55                  60

Asn Gly Lys Leu Thr Leu Lys Phe Ile Cys Thr Thr Gly Lys Leu Pro
65                  70                  75                  80

Val Pro Trp Pro Thr Leu Val Thr Thr Leu Thr Tyr Gly Val Gln Cys
                85                  90                  95

Phe Ser Arg Tyr Pro Asp His Met Lys Arg His Asp Phe Phe Lys Ser
                100                 105                 110
```

Ala Met Pro Glu Gly Tyr Val Gln Glu Arg Thr Ile Ser Phe Lys Asp
            115                 120                 125

Asp Gly Thr Tyr Lys Thr Arg Ala Glu Val Lys Phe Glu Gly Asp Thr
        130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Phe Asn Ser His Asn Val
                165                 170                 175

Tyr Ile Thr Ala Asp Lys Gln Lys Asn Gly Ile Lys Ala Asn Phe Lys
            180                 185                 190

Ile Arg His Asn Val Glu Asp Gly Ser Val Gln Leu Ala Asp His Tyr
        195                 200                 205

Gln Gln Asn Thr Pro Ile Gly Asp Gly Pro Val Leu Leu Pro Asp Asn
    210                 215                 220

His Tyr Leu Ser Thr Gln Ser Val Leu Ser Lys Asp Pro Asn Glu Lys
225                 230                 235                 240

Arg Asp His Met Val Leu Leu Glu Phe Val Thr Ala Ala Gly Ile Thr
                245                 250                 255

His Gly Gly Ser Gly
            260

<210> SEQ ID NO 2
<211> LENGTH: 3144
<212> TYPE: PRT
<213> ORGANISM: Homo sapiens
<220> FEATURE:
<223> OTHER INFORMATION: HTT-Q23

<400> SEQUENCE: 2

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

-continued

```
Val Asn Leu Leu Pro Cys Leu Thr Arg Thr Ser Lys Arg Pro Glu Glu
        210             215             220
Ser Val Gln Glu Thr Leu Ala Ala Val Pro Lys Ile Met Ala Ser
225             230             235             240
Phe Gly Asn Phe Ala Asn Asp Asn Glu Ile Lys Val Leu Leu Lys Ala
                245             250             255
Phe Ile Ala Asn Leu Lys Ser Ser Pro Thr Ile Arg Arg Thr Ala
            260             265             270
Ala Gly Ser Ala Val Ser Ile Cys Gln His Ser Arg Arg Thr Gln Tyr
                275             280             285
Phe Tyr Ser Trp Leu Leu Asn Val Leu Leu Gly Leu Leu Val Pro Val
        290             295             300
Glu Asp Glu His Ser Thr Leu Ile Leu Gly Val Leu Leu Thr Leu
305             310             315             320
Arg Tyr Leu Val Pro Leu Leu Gln Gln Gln Val Lys Asp Thr Ser Leu
                325             330             335
Lys Gly Ser Phe Gly Val Thr Arg Lys Glu Met Glu Val Ser Pro Ser
            340             345             350
Ala Glu Gln Leu Val Gln Val Tyr Glu Leu Thr Leu His His Thr Gln
                355             360             365
His Gln Asp His Asn Val Val Thr Gly Ala Leu Glu Leu Leu Gln Gln
        370             375             380
Leu Phe Arg Thr Pro Pro Pro Glu Leu Leu Gln Thr Leu Thr Ala Val
385             390             395             400
Gly Gly Ile Gly Gln Leu Thr Ala Ala Lys Glu Glu Ser Gly Gly Arg
                405             410             415
Ser Arg Ser Gly Ser Ile Val Glu Leu Ile Ala Gly Gly Ser Ser
            420             425             430
Cys Ser Pro Val Leu Ser Arg Lys Gln Lys Gly Lys Val Leu Leu Gly
        435             440             445
Glu Glu Glu Ala Leu Glu Asp Asp Ser Glu Ser Arg Ser Asp Val Ser
            450             455             460
Ser Ser Ala Leu Thr Ala Ser Val Lys Asp Glu Ile Ser Gly Glu Leu
465             470             475             480
Ala Ala Ser Ser Gly Val Ser Thr Pro Gly Ser Ala Gly His Asp Ile
                485             490             495
Ile Thr Glu Gln Pro Arg Ser Gln His Thr Leu Gln Ala Asp Ser Val
            500             505             510
Asp Leu Ala Ser Cys Asp Leu Thr Ser Ala Thr Asp Gly Asp Glu
        515             520             525
Glu Asp Ile Leu Ser His Ser Ser Gln Val Ser Ala Val Pro Ser
530             535             540
Asp Pro Ala Met Asp Leu Asn Asp Gly Thr Gln Ala Ser Ser Pro Ile
545             550             555             560
Ser Asp Ser Ser Gln Thr Thr Thr Glu Gly Pro Asp Ser Ala Val Thr
                565             570             575
Pro Ser Asp Ser Ser Glu Ile Val Leu Asp Gly Thr Asp Asn Gln Tyr
            580             585             590
Leu Gly Leu Gln Ile Gly Gln Pro Gln Asp Glu Asp Glu Ala Thr
        595             600             605
Gly Ile Leu Pro Asp Glu Ala Ser Glu Ala Phe Arg Asn Ser Ser Met
610             615             620
Ala Leu Gln Gln Ala His Leu Leu Lys Asn Met Ser His Cys Arg Gln
```

-continued

```
            625                 630                 635                 640
         Pro Ser Asp Ser Ser Val Asp Lys Phe Val Leu Arg Asp Glu Ala Thr
                             645                 650                 655
         Glu Pro Gly Asp Gln Glu Asn Lys Pro Cys Arg Ile Lys Gly Asp Ile
                 660                 665                 670
         Gly Gln Ser Thr Asp Asp Ser Ala Pro Leu Val His Cys Val Arg
                 675                 680                 685
         Leu Leu Ser Ala Ser Phe Leu Leu Thr Gly Gly Lys Asn Val Leu Val
                 690                 695                 700
         Pro Asp Arg Asp Val Arg Val Ser Val Lys Ala Leu Ala Leu Ser Cys
         705                 710                 715                 720
         Val Gly Ala Ala Val Ala Leu His Pro Glu Ser Phe Phe Ser Lys Leu
                             725                 730                 735
         Tyr Lys Val Pro Leu Asp Thr Thr Glu Tyr Pro Glu Glu Gln Tyr Val
                         740                 745                 750
         Ser Asp Ile Leu Asn Tyr Ile Asp His Gly Asp Pro Gln Val Arg Gly
                     755                 760                 765
         Ala Thr Ala Ile Leu Cys Gly Thr Leu Ile Cys Ser Ile Leu Ser Arg
                 770                 775                 780
         Ser Arg Phe His Val Gly Asp Trp Met Gly Thr Ile Arg Thr Leu Thr
         785                 790                 795                 800
         Gly Asn Thr Phe Ser Leu Ala Asp Cys Ile Pro Leu Leu Arg Lys Thr
                             805                 810                 815
         Leu Lys Asp Glu Ser Ser Val Thr Cys Lys Leu Ala Cys Thr Ala Val
                         820                 825                 830
         Arg Asn Cys Val Met Ser Leu Cys Ser Ser Tyr Ser Glu Leu Gly
                     835                 840                 845
         Leu Gln Leu Ile Ile Asp Val Leu Thr Leu Arg Asn Ser Ser Tyr Trp
                 850                 855                 860
         Leu Val Arg Thr Glu Leu Leu Glu Thr Leu Ala Glu Ile Asp Phe Arg
         865                 870                 875                 880
         Leu Val Ser Phe Leu Glu Ala Lys Ala Glu Asn Leu His Arg Gly Ala
                             885                 890                 895
         His His Tyr Thr Gly Leu Leu Lys Leu Gln Glu Arg Val Leu Asn Asn
                         900                 905                 910
         Val Val Ile His Leu Leu Gly Asp Glu Asp Pro Arg Val Arg His Val
                     915                 920                 925
         Ala Ala Ala Ser Leu Ile Arg Leu Val Pro Lys Leu Phe Tyr Lys Cys
                 930                 935                 940
         Asp Gln Gly Gln Ala Asp Pro Val Val Ala Val Ala Arg Asp Gln Ser
         945                 950                 955                 960
         Ser Val Tyr Leu Lys Leu Leu Met His Glu Thr Gln Pro Pro Ser His
                             965                 970                 975
         Phe Ser Val Ser Thr Ile Thr Arg Ile Tyr Arg Gly Tyr Asn Leu Leu
                         980                 985                 990
         Pro Ser Ile Thr Asp Val Thr Met  Glu Asn Asn Leu Ser  Arg Val Ile
                     995                 1000                1005
         Ala Ala  Val Ser His Glu Leu  Ile Thr Ser Thr  Thr  Arg Ala Leu
                 1010                1015                1020
         Thr Phe  Gly Cys Cys Glu Ala  Leu Cys Leu Leu Ser   Thr Ala Phe
                 1025                1030                1035
         Pro Val  Cys Ile Trp Ser Leu  Gly Trp His Cys Gly   Val Pro Pro
                 1040                1045                1050
```

```
Leu Ser Ala Ser Asp Glu Ser Arg Lys Ser Cys Thr Val Gly Met
    1055            1060            1065

Ala Thr Met Ile Leu Thr Leu Leu Ser Ser Ala Trp Phe Pro Leu
    1070            1075            1080

Asp Leu Ser Ala His Gln Asp Ala Leu Ile Leu Ala Gly Asn Leu
    1085            1090            1095

Leu Ala Ala Ser Ala Pro Lys Ser Leu Arg Ser Ser Trp Ala Ser
    1100            1105            1110

Glu Glu Glu Ala Asn Pro Ala Ala Thr Lys Gln Glu Glu Val Trp
    1115            1120            1125

Pro Ala Leu Gly Asp Arg Ala Leu Val Pro Met Val Glu Gln Leu
    1130            1135            1140

Phe Ser His Leu Leu Lys Val Ile Asn Ile Cys Ala His Val Leu
    1145            1150            1155

Asp Asp Val Ala Pro Gly Pro Ala Ile Lys Ala Ala Leu Pro Ser
    1160            1165            1170

Leu Thr Asn Pro Pro Ser Leu Ser Pro Ile Arg Arg Lys Gly Lys
    1175            1180            1185

Glu Lys Glu Pro Gly Glu Gln Ala Ser Val Pro Leu Ser Pro Lys
    1190            1195            1200

Lys Gly Ser Glu Ala Ser Ala Ala Ser Arg Gln Ser Asp Thr Ser
    1205            1210            1215

Gly Pro Val Thr Thr Ser Lys Ser Ser Ser Leu Gly Ser Phe Tyr
    1220            1225            1230

His Leu Pro Ser Tyr Leu Lys Leu His Asp Val Leu Lys Ala Thr
    1235            1240            1245

His Ala Asn Tyr Lys Val Thr Leu Asp Leu Gln Asn Ser Thr Glu
    1250            1255            1260

Lys Phe Gly Gly Phe Leu Arg Ser Ala Leu Asp Val Leu Ser Gln
    1265            1270            1275

Ile Leu Glu Leu Ala Thr Leu Gln Asp Ile Gly Lys Cys Val Glu
    1280            1285            1290

Glu Ile Leu Gly Tyr Leu Lys Ser Cys Phe Ser Arg Glu Pro Met
    1295            1300            1305

Met Ala Thr Val Cys Val Gln Gln Leu Leu Lys Thr Leu Phe Gly
    1310            1315            1320

Thr Asn Leu Ala Ser Gln Phe Asp Gly Leu Ser Ser Asn Pro Ser
    1325            1330            1335

Lys Ser Gln Gly Arg Ala Gln Arg Leu Gly Ser Ser Ser Val Arg
    1340            1345            1350

Pro Gly Leu Tyr His Tyr Cys Phe Met Ala Pro Tyr Thr His Phe
    1355            1360            1365

Thr Gln Ala Leu Ala Asp Ala Ser Leu Arg Asn Met Val Gln Ala
    1370            1375            1380

Glu Gln Glu Asn Asp Thr Ser Gly Trp Phe Asp Val Leu Gln Lys
    1385            1390            1395

Val Ser Thr Gln Leu Lys Thr Asn Leu Thr Ser Val Thr Lys Asn
    1400            1405            1410

Arg Ala Asp Lys Asn Ala Ile His Asn His Ile Arg Leu Phe Glu
    1415            1420            1425

Pro Leu Val Ile Lys Ala Leu Lys Gln Tyr Thr Thr Thr Thr Cys
    1430            1435            1440
```

```
Val Gln Leu Gln Lys Gln Val Leu Asp Leu Leu Ala Gln Leu Val
1445                1450                1455

Gln Leu Arg Val Asn Tyr Cys Leu Leu Asp Ser Asp Gln Val Phe
1460                1465                1470

Ile Gly Phe Val Leu Lys Gln Phe Glu Tyr Ile Glu Val Gly Gln
1475                1480                1485

Phe Arg Glu Ser Glu Ala Ile Ile Pro Asn Ile Phe Phe Phe Leu
1490                1495                1500

Val Leu Leu Ser Tyr Glu Arg Tyr His Ser Lys Gln Ile Ile Gly
1505                1510                1515

Ile Pro Lys Ile Ile Gln Leu Cys Asp Gly Ile Met Ala Ser Gly
1520                1525                1530

Arg Lys Ala Val Thr His Ala Ile Pro Ala Leu Gln Pro Ile Val
1535                1540                1545

His Asp Leu Phe Val Leu Arg Gly Thr Asn Lys Ala Asp Ala Gly
1550                1555                1560

Lys Glu Leu Glu Thr Gln Lys Glu Val Val Ser Met Leu Leu
1565                1570                1575

Arg Leu Ile Gln Tyr His Gln Val Leu Glu Met Phe Ile Leu Val
1580                1585                1590

Leu Gln Gln Cys His Lys Glu Asn Glu Asp Lys Trp Lys Arg Leu
1595                1600                1605

Ser Arg Gln Ile Ala Asp Ile Ile Leu Pro Met Leu Ala Lys Gln
1610                1615                1620

Gln Met His Ile Asp Ser His Glu Ala Leu Gly Val Leu Asn Thr
1625                1630                1635

Leu Phe Glu Ile Leu Ala Pro Ser Ser Leu Arg Pro Val Asp Met
1640                1645                1650

Leu Leu Arg Ser Met Phe Val Thr Pro Asn Thr Met Ala Ser Val
1655                1660                1665

Ser Thr Val Gln Leu Trp Ile Ser Gly Ile Leu Ala Ile Leu Arg
1670                1675                1680

Val Leu Ile Ser Gln Ser Thr Glu Asp Ile Val Leu Ser Arg Ile
1685                1690                1695

Gln Glu Leu Ser Phe Ser Pro Tyr Leu Ile Ser Cys Thr Val Ile
1700                1705                1710

Asn Arg Leu Arg Asp Gly Asp Ser Thr Ser Thr Leu Glu Glu His
1715                1720                1725

Ser Glu Gly Lys Gln Ile Lys Asn Leu Pro Glu Glu Thr Phe Ser
1730                1735                1740

Arg Phe Leu Leu Gln Leu Val Gly Ile Leu Leu Glu Asp Ile Val
1745                1750                1755

Thr Lys Gln Leu Lys Val Glu Met Ser Glu Gln Gln His Thr Phe
1760                1765                1770

Tyr Cys Gln Glu Leu Gly Thr Leu Leu Met Cys Leu Ile His Ile
1775                1780                1785

Phe Lys Ser Gly Met Phe Arg Arg Ile Thr Ala Ala Ala Thr Arg
1790                1795                1800

Leu Phe Arg Ser Asp Gly Cys Gly Gly Ser Phe Tyr Thr Leu Asp
1805                1810                1815

Ser Leu Asn Leu Arg Ala Arg Ser Met Ile Thr Thr His Pro Ala
1820                1825                1830

Leu Val Leu Leu Trp Cys Gln Ile Leu Leu Leu Val Asn His Thr
```

-continued

```
                1835                1840                1845

Asp Tyr Arg Trp Trp Ala Glu Val Gln Gln Thr Pro Lys Arg His
        1850                1855                1860

Ser Leu Ser Ser Thr Lys Leu Leu Ser Pro Gln Met Ser Gly Glu
        1865                1870                1875

Glu Glu Asp Ser Asp Leu Ala Ala Lys Leu Gly Met Cys Asn Arg
        1880                1885                1890

Glu Ile Val Arg Arg Gly Ala Leu Ile Leu Phe Cys Asp Tyr Val
        1895                1900                1905

Cys Gln Asn Leu His Asp Ser Glu His Leu Thr Trp Leu Ile Val
        1910                1915                1920

Asn His Ile Gln Asp Leu Ile Ser Leu Ser His Glu Pro Pro Val
        1925                1930                1935

Gln Asp Phe Ile Ser Ala Val His Arg Asn Ser Ala Ala Ser Gly
        1940                1945                1950

Leu Phe Ile Gln Ala Ile Gln Ser Arg Cys Glu Asn Leu Ser Thr
        1955                1960                1965

Pro Thr Met Leu Lys Lys Thr Leu Gln Cys Leu Glu Gly Ile His
        1970                1975                1980

Leu Ser Gln Ser Gly Ala Val Leu Thr Leu Tyr Val Asp Arg Leu
        1985                1990                1995

Leu Cys Thr Pro Phe Arg Val Leu Ala Arg Met Val Asp Ile Leu
        2000                2005                2010

Ala Cys Arg Arg Val Glu Met Leu Leu Ala Ala Asn Leu Gln Ser
        2015                2020                2025

Ser Met Ala Gln Leu Pro Met Glu Glu Leu Asn Arg Ile Gln Glu
        2030                2035                2040

Tyr Leu Gln Ser Ser Gly Leu Ala Gln Arg His Gln Arg Leu Tyr
        2045                2050                2055

Ser Leu Leu Asp Arg Phe Arg Leu Ser Thr Met Gln Asp Ser Leu
        2060                2065                2070

Ser Pro Ser Pro Pro Val Ser Ser His Pro Leu Asp Gly Asp Gly
        2075                2080                2085

His Val Ser Leu Glu Thr Val Ser Pro Asp Lys Asp Trp Tyr Val
        2090                2095                2100

His Leu Val Lys Ser Gln Cys Trp Thr Arg Ser Asp Ser Ala Leu
        2105                2110                2115

Leu Glu Gly Ala Glu Leu Val Asn Arg Ile Pro Ala Glu Asp Met
        2120                2125                2130

Asn Ala Phe Met Met Asn Ser Glu Phe Asn Leu Ser Leu Leu Ala
        2135                2140                2145

Pro Cys Leu Ser Leu Gly Met Ser Glu Ile Ser Gly Gly Gln Lys
        2150                2155                2160

Ser Ala Leu Phe Glu Ala Ala Arg Glu Val Thr Leu Ala Arg Val
        2165                2170                2175

Ser Gly Thr Val Gln Gln Leu Pro Ala Val His His Val Phe Gln
        2180                2185                2190

Pro Glu Leu Pro Ala Glu Pro Ala Ala Tyr Trp Ser Lys Leu Asn
        2195                2200                2205

Asp Leu Phe Gly Asp Ala Ala Leu Tyr Gln Ser Leu Pro Thr Leu
        2210                2215                2220

Ala Arg Ala Leu Ala Gln Tyr Leu Val Val Val Ser Lys Leu Pro
        2225                2230                2235
```

-continued

Ser His Leu His Leu Pro Pro Glu Lys Glu Lys Asp Ile Val Lys
    2240                2245                2250

Phe Val Val Ala Thr Leu Glu Ala Leu Ser Trp His Leu Ile His
    2255                2260                2265

Glu Gln Ile Pro Leu Ser Leu Asp Leu Gln Ala Gly Leu Asp Cys
    2270                2275                2280

Cys Cys Leu Ala Leu Gln Leu Pro Gly Leu Trp Ser Val Val Ser
    2285                2290                2295

Ser Thr Glu Phe Val Thr His Ala Cys Ser Leu Ile Tyr Cys Val
    2300                2305                2310

His Phe Ile Leu Glu Ala Val Ala Val Gln Pro Gly Glu Gln Leu
    2315                2320                2325

Leu Ser Pro Glu Arg Arg Thr Asn Thr Pro Lys Ala Ile Ser Glu
    2330                2335                2340

Glu Glu Glu Glu Val Asp Pro Asn Thr Gln Asn Pro Lys Tyr Ile
    2345                2350                2355

Thr Ala Ala Cys Glu Met Val Ala Glu Met Val Glu Ser Leu Gln
    2360                2365                2370

Ser Val Leu Ala Leu Gly His Lys Arg Asn Ser Gly Val Pro Ala
    2375                2380                2385

Phe Leu Thr Pro Leu Leu Arg Asn Ile Ile Ile Ser Leu Ala Arg
    2390                2395                2400

Leu Pro Leu Val Asn Ser Tyr Thr Arg Val Pro Pro Leu Val Trp
    2405                2410                2415

Lys Leu Gly Trp Ser Pro Lys Pro Gly Gly Asp Phe Gly Thr Ala
    2420                2425                2430

Phe Pro Glu Ile Pro Val Glu Phe Leu Gln Glu Lys Glu Val Phe
    2435                2440                2445

Lys Glu Phe Ile Tyr Arg Ile Asn Thr Leu Gly Trp Thr Ser Arg
    2450                2455                2460

Thr Gln Phe Glu Glu Thr Trp Ala Thr Leu Leu Gly Val Leu Val
    2465                2470                2475

Thr Gln Pro Leu Val Met Glu Gln Glu Glu Ser Pro Pro Glu Glu
    2480                2485                2490

Asp Thr Glu Arg Thr Gln Ile Asn Val Leu Ala Val Gln Ala Ile
    2495                2500                2505

Thr Ser Leu Val Leu Ser Ala Met Thr Val Pro Val Ala Gly Asn
    2510                2515                2520

Pro Ala Val Ser Cys Leu Glu Gln Gln Pro Arg Asn Lys Pro Leu
    2525                2530                2535

Lys Ala Leu Asp Thr Arg Phe Gly Arg Lys Leu Ser Ile Ile Arg
    2540                2545                2550

Gly Ile Val Glu Gln Glu Ile Gln Ala Met Val Ser Lys Arg Glu
    2555                2560                2565

Asn Ile Ala Thr His His Leu Tyr Gln Ala Trp Asp Pro Val Pro
    2570                2575                2580

Ser Leu Ser Pro Ala Thr Thr Gly Ala Leu Ile Ser His Glu Lys
    2585                2590                2595

Leu Leu Leu Gln Ile Asn Pro Glu Arg Glu Leu Gly Ser Met Ser
    2600                2605                2610

Tyr Lys Leu Gly Gln Val Ser Ile His Ser Val Trp Leu Gly Asn
    2615                2620                2625

```
Ser Ile Thr Pro Leu Arg Glu Glu Trp Asp Glu Glu Glu
2630                2635            2640

Glu Glu Ala Asp Ala Pro Ala Pro Ser Ser Pro Thr Ser Pro
2645                2650            2655

Val Asn Ser Arg Lys His Arg Ala Gly Val Asp Ile His Ser Cys
2660                2665            2670

Ser Gln Phe Leu Leu Glu Leu Tyr Ser Arg Trp Ile Leu Pro Ser
2675                2680            2685

Ser Ser Ala Arg Arg Thr Pro Ala Ile Leu Ile Ser Glu Val Val
2690                2695            2700

Arg Ser Leu Leu Val Val Ser Asp Leu Phe Thr Glu Arg Asn Gln
2705                2710            2715

Phe Glu Leu Met Tyr Val Thr Leu Thr Glu Leu Arg Arg Val His
2720                2725            2730

Pro Ser Glu Asp Glu Ile Leu Ala Gln Tyr Leu Val Pro Ala Thr
2735                2740            2745

Cys Lys Ala Ala Ala Val Leu Gly Met Asp Lys Ala Val Ala Glu
2750                2755            2760

Pro Val Ser Arg Leu Leu Glu Ser Thr Leu Arg Ser Ser His Leu
2765                2770            2775

Pro Ser Arg Val Gly Ala Leu His Gly Val Leu Tyr Val Leu Glu
2780                2785            2790

Cys Asp Leu Leu Asp Asp Thr Ala Lys Gln Leu Ile Pro Val Ile
2795                2800            2805

Ser Asp Tyr Leu Leu Ser Asn Leu Lys Gly Ile Ala His Cys Val
2810                2815            2820

Asn Ile His Ser Gln Gln His Val Leu Val Met Cys Ala Thr Ala
2825                2830            2835

Phe Tyr Leu Ile Glu Asn Tyr Pro Leu Asp Val Gly Pro Glu Phe
2840                2845            2850

Ser Ala Ser Ile Ile Gln Met Cys Gly Val Met Leu Ser Gly Ser
2855                2860            2865

Glu Glu Ser Thr Pro Ser Ile Ile Tyr His Cys Ala Leu Arg Gly
2870                2875            2880

Leu Glu Arg Leu Leu Leu Ser Glu Gln Leu Ser Arg Leu Asp Ala
2885                2890            2895

Glu Ser Leu Val Lys Leu Ser Val Asp Arg Val Asn Val His Ser
2900                2905            2910

Pro His Arg Ala Met Ala Ala Leu Gly Leu Met Leu Thr Cys Met
2915                2920            2925

Tyr Thr Gly Lys Glu Lys Val Ser Pro Gly Arg Thr Ser Asp Pro
2930                2935            2940

Asn Pro Ala Ala Pro Asp Ser Glu Ser Val Ile Val Ala Met Glu
2945                2950            2955

Arg Val Ser Val Leu Phe Asp Arg Ile Arg Lys Gly Phe Pro Cys
2960                2965            2970

Glu Ala Arg Val Val Ala Arg Ile Leu Pro Gln Phe Leu Asp Asp
2975                2980            2985

Phe Phe Pro Pro Gln Asp Ile Met Asn Lys Val Ile Gly Glu Phe
2990                2995            3000

Leu Ser Asn Gln Gln Pro Tyr Pro Gln Phe Met Ala Thr Val Val
3005                3010            3015

Tyr Lys Val Phe Gln Thr Leu His Ser Thr Gly Gln Ser Ser Met
```

```
                    3020                3025                3030

Val Arg Asp Trp Val Met Leu Ser Leu Ser Asn Phe Thr Gln Arg
    3035                3040                3045

Ala Pro Val Ala Met Ala Thr Trp Ser Leu Ser Cys Phe Phe Val
    3050                3055                3060

Ser Ala Ser Thr Ser Pro Trp Val Ala Ala Ile Leu Pro His Val
    3065                3070                3075

Ile Ser Arg Met Gly Lys Leu Glu Gln Val Asp Val Asn Leu Phe
    3080                3085                3090

Cys Leu Val Ala Thr Asp Phe Tyr Arg His Gln Ile Glu Glu Glu
    3095                3100                3105

Leu Asp Arg Arg Ala Phe Gln Ser Val Leu Glu Val Val Ala Ala
    3110                3115                3120

Pro Gly Ser Pro Tyr His Arg Leu Leu Thr Cys Leu Arg Asn Val
    3125                3130                3135

His Lys Val Thr Thr Cys
    3140

<210> SEQ ID NO 3
<211> LENGTH: 412
<212> TYPE: PRT
<213> ORGANISM: Homo sapiens
<220> FEATURE:
<223> OTHER INFORMATION: ATXN3-Q74

<400> SEQUENCE: 3

Met Glu Ser Ile Phe His Glu Lys Gln Glu Gly Ser Leu Cys Ala Gln
1               5                   10                  15

His Cys Leu Asn Asn Leu Leu Gln Gly Glu Tyr Phe Ser Pro Val Glu
            20                  25                  30

Leu Ser Ser Ile Ala His Gln Leu Asp Glu Glu Glu Arg Met Arg Met
        35                  40                  45

Ala Glu Gly Gly Val Thr Ser Glu Asp Tyr Arg Thr Phe Leu Gln Gln
    50                  55                  60

Pro Ser Gly Asn Met Asp Asp Ser Gly Phe Phe Ser Ile Gln Val Ile
65                  70                  75                  80

Ser Asn Ala Leu Lys Val Trp Gly Leu Glu Leu Ile Leu Phe Asn Ser
                85                  90                  95

Pro Glu Tyr Gln Arg Leu Arg Ile Asp Pro Ile Asn Glu Arg Ser Phe
            100                 105                 110

Ile Cys Asn Tyr Lys Glu His Trp Phe Thr Val Arg Lys Leu Gly Lys
        115                 120                 125

Gln Trp Phe Asn Leu Asn Ser Leu Leu Thr Gly Pro Glu Leu Ile Ser
    130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
                165                 170                 175

Leu Leu Gln Met Ile Arg Val Gln Gln Met His Arg Pro Lys Leu Ile
            180                 185                 190

Gly Glu Glu Leu Ala Gln Leu Lys Glu Gln Arg Val His Lys Thr Asp
        195                 200                 205

Leu Glu Arg Met Leu Glu Ala Asn Asp Gly Ser Gly Met Leu Asp Glu
    210                 215                 220

Asp Glu Glu Asp Leu Gln Arg Ala Leu Ala Leu Ser Arg Gln Glu Ile
```

```
                225                 230                 235                 240
Asp Met Glu Asp Glu Ala Asp Leu Arg Arg Ala Ile Gln Leu Ser
                245                 250                 255

Met Gln Gly Ser Ser Arg Asn Ile Ser Gln Asp Met Thr Gln Thr Ser
                260                 265                 270

Gly Thr Asn Leu Thr Ser Glu Leu Arg Lys Arg Glu Ala Tyr
                275                 280                 285

Phe Glu Lys Gln Gln Lys Gln Gln Gln Gln Gln Gln Gln Gln
                290                 295                 300

Gln Gln Gln Gln Gln Gln Gln Gln Gln Gln Gln Gln Gln Gln
305                 310                 315                 320

Gln Gln Gln Gln Gln Gln Gln Gln Gln Gln Gln Gln Gln Gln
                325                 330                 335

Gln Gln Gln Gln Gln Gln Gln Gln Gln Gln Gln Gln Gln Gln
                340                 345                 350

Gln Gln Gln Gln Gln Gln Gln Gln Gln Gln Gln Gln Gln Gln
                355                 360                 365

Gln Arg Asp Leu Ser Gly Gln Ser Ser His Pro Cys Glu Arg Pro Ala
370                 375                 380

Thr Ser Ser Gly Ala Leu Gly Ser Asp Leu Gly Lys Ala Cys Ser Pro
385                 390                 395                 400

Phe Ile Met Phe Ala Thr Phe Thr Leu Tyr Leu Thr
                405                 410

<210> SEQ ID NO 4
<211> LENGTH: 365
<212> TYPE: PRT
<213> ORGANISM: Homo sapiens
<220> FEATURE:
<223> OTHER INFORMATION: ATXN3-Q27

<400> SEQUENCE: 4

Met Glu Ser Ile Phe His Glu Lys Gln Glu Gly Ser Leu Cys Ala Gln
1               5                   10                  15

His Cys Leu Asn Asn Leu Leu Gln Gly Glu Tyr Phe Ser Pro Val Glu
                20                  25                  30

Leu Ser Ser Ile Ala His Gln Leu Asp Glu Glu Arg Met Arg Met
                35                  40                  45

Ala Glu Gly Gly Val Thr Ser Glu Asp Tyr Arg Thr Phe Leu Gln Gln
            50                  55                  60

Pro Ser Gly Asn Met Asp Asp Ser Gly Phe Phe Ser Ile Gln Val Ile
65                  70                  75                  80

Ser Asn Ala Leu Lys Val Trp Gly Leu Glu Leu Ile Leu Phe Asn Ser
                85                  90                  95

Pro Glu Tyr Gln Arg Leu Arg Ile Asp Pro Ile Asn Glu Arg Ser Phe
                100                 105                 110

Ile Cys Asn Tyr Lys Glu His Trp Phe Thr Val Arg Lys Leu Gly Lys
                115                 120                 125

Gln Trp Phe Asn Leu Asn Ser Leu Leu Thr Gly Pro Glu Leu Ile Ser
            130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
                165                 170                 175

Leu Leu Gln Met Ile Arg Val Gln Gln Met His Arg Pro Lys Leu Ile
```

```
                180             185                 190
    Gly Glu Glu Leu Ala Gln Leu Lys Glu Gln Arg Val His Lys Thr Asp
                    195                 200                 205
    Leu Glu Arg Met Leu Glu Ala Asn Asp Gly Ser Gly Met Leu Asp Glu
                    210                 215                 220
    Asp Glu Glu Asp Leu Gln Arg Ala Leu Ala Leu Ser Arg Gln Glu Ile
    225                 230                 235                 240
    Asp Met Glu Asp Glu Glu Ala Asp Leu Arg Arg Ala Ile Gln Leu Ser
                    245                 250                 255
    Met Gln Gly Ser Ser Arg Asn Ile Ser Gln Asp Met Thr Gln Thr Ser
                    260                 265                 270
    Gly Thr Asn Leu Thr Ser Glu Glu Leu Arg Lys Arg Arg Glu Ala Tyr
                    275                 280                 285
    Phe Glu Lys Gln Gln Gln Lys Gln Gln Gln Gln Gln Gln Gln Gln Gln
                    290                 295                 300
    Gln Gln Gln Gln Gln Gln Gln Gln Gln Gln Gln Gln Gln Gln Gln Gln
    305                 310                 315                 320
    Gln Gln Arg Asp Leu Ser Gly Gln Ser Ser His Pro Cys Glu Arg Pro
                    325                 330                 335
    Ala Thr Ser Ser Gly Ala Leu Gly Ser Asp Leu Gly Lys Ala Cys Ser
                    340                 345                 350
    Pro Phe Ile Met Phe Ala Thr Phe Thr Leu Tyr Leu Thr
                    355                 360                 365

<210> SEQ ID NO 5
<211> LENGTH: 895
<212> TYPE: PRT
<213> ORGANISM: Homo sapiens
<220> FEATURE:
<223> OTHER INFORMATION: ATXN1-Q92

<400> SEQUENCE: 5

Met Lys Ser Asn Gln Glu Arg Ser Asn Glu Cys Leu Pro Pro Lys Lys
    1               5                   10                  15
    Arg Glu Ile Pro Ala Thr Ser Arg Ser Ser Glu Glu Lys Ala Pro Thr
                    20                  25                  30
    Leu Pro Ser Asp Asn His Arg Val Glu Gly Thr Ala Trp Leu Pro Gly
                    35                  40                  45
    Asn Pro Gly Gly Arg Gly His Gly Gly Gly Arg His Gly Pro Ala Gly
                    50                  55                  60
    Thr Ser Val Glu Leu Gly Leu Gln Gln Gly Ile Gly Leu His Lys Ala
    65                  70                  75                  80
    Leu Ser Thr Gly Leu Asp Tyr Ser Pro Pro Ser Ala Pro Arg Ser Val
                    85                  90                  95
    Pro Val Ala Thr Thr Leu Pro Ala Ala Tyr Ala Thr Pro Gln Pro Gly
                    100                 105                 110
    Thr Pro Val Ser Pro Val Gln Tyr Ala His Leu Pro His Thr Phe Gln
                    115                 120                 125
    Phe Ile Gly Ser Ser Gln Tyr Ser Gly Thr Tyr Ala Ser Phe Ile Pro
                    130                 135                 140
    Ser Gln Leu Ile Pro Pro Thr Ala Asn Pro Val Thr Ser Ala Val Ala
    145                 150                 155                 160
    Ser Ala Ala Gly Ala Thr Thr Pro Ser Gln Arg Ser Gln Leu Glu Ala
                    165                 170                 175
    Tyr Ser Thr Leu Leu Ala Asn Met Gly Ser Leu Ser Gln Thr Pro Gly
```

His Lys Ala Glu Gln Gln Gln Gln Gln Gln Gln Gln Gln Gln
              195                 200                 205
Gln Gln Gln Gln Gln Gln Gln Gln Gln Gln Gln Gln Gln Gln
    210                 215                 220
Gln Gln Gln Gln Gln Gln Gln Gln Gln Gln Gln Gln Gln Gln
225                 230                 235                 240
Gln Gln Gln Gln Gln Gln Gln Gln Gln Gln Gln Gln Gln Gln
                245                 250                 255
Gln Gln Gln Gln Gln Gln Gln Gln Gln Gln Gln Gln Gln Gln
            260                 265                 270
Gln Gln Gln Gln Gln Gln Gln Gln Gln Gln Gln Gln Gln Gln
        275                 280                 285
His Gln His Gln Gln Gln Gln Gln Gln Gln Gln Gln Gln Gln
            290                 295                 300
Gln His Leu Ser Arg Ala Pro Gly Leu Ile Thr Pro Gly Ser Pro Pro
305                 310                 315                 320
Pro Ala Gln Gln Asn Gln Tyr Val His Ile Ser Ser Pro Gln Asn
                325                 330                 335
Thr Gly Arg Thr Ala Ser Pro Pro Ala Ile Pro Val His Leu His Pro
                340                 345                 350
His Gln Thr Met Ile Pro His Thr Leu Thr Leu Gly Pro Pro Ser Gln
            355                 360                 365
Val Val Met Gln Tyr Ala Asp Ser Gly Ser His Phe Val Pro Arg Glu
        370                 375                 380
Ala Thr Lys Lys Ala Glu Ser Ser Arg Leu Gln Gln Ala Ile Gln Ala
385                 390                 395                 400
Lys Glu Val Leu Asn Gly Glu Met Glu Lys Ser Arg Arg Tyr Gly Ala
                405                 410                 415
Pro Ser Ser Ala Asp Leu Gly Leu Gly Lys Ala Gly Gly Lys Ser Val
                420                 425                 430
Pro His Pro Tyr Glu Ser Arg His Val Val His Pro Ser Pro Ser
        435                 440                 445
Asp Tyr Ser Ser Arg Asp Pro Ser Gly Val Arg Ala Ser Val Met Val
    450                 455                 460
Leu Pro Asn Ser Asn Thr Pro Ala Ala Asp Leu Glu Val Gln Gln Ala
465                 470                 475                 480
Thr His Arg Glu Ala Ser Pro Ser Thr Leu Asn Asp Lys Ser Gly Leu
                485                 490                 495
His Leu Gly Lys Pro Gly His Arg Ser Tyr Ala Leu Ser Pro His Thr
            500                 505                 510
Val Ile Gln Thr Thr His Ser Ala Ser Glu Pro Leu Pro Val Gly Leu
        515                 520                 525
Pro Ala Thr Ala Phe Tyr Ala Gly Thr Gln Pro Pro Val Ile Gly Tyr
    530                 535                 540
Leu Ser Gly Gln Gln Gln Ala Ile Thr Tyr Ala Gly Ser Leu Pro Gln
545                 550                 555                 560
His Leu Val Ile Pro Gly Thr Gln Pro Leu Leu Ile Pro Val Gly Ser
                565                 570                 575
Thr Asp Met Glu Ala Ser Gly Ala Ala Pro Ala Ile Val Thr Ser Ser
            580                 585                 590
Pro Gln Phe Ala Ala Val Pro His Thr Phe Val Thr Thr Ala Leu Pro
        595                 600                 605

```
Lys Ser Glu Asn Phe Asn Pro Glu Ala Leu Val Thr Gln Ala Ala Tyr
        610                 615                 620

Pro Ala Met Val Gln Ala Gln Ile His Leu Pro Val Val Gln Ser Val
625                 630                 635                 640

Ala Ser Pro Ala Ala Pro Pro Thr Leu Pro Pro Tyr Phe Met Lys
            645                 650                 655

Gly Ser Ile Ile Gln Leu Ala Asn Gly Glu Leu Lys Lys Val Glu Asp
        660                 665                 670

Leu Lys Thr Glu Asp Phe Ile Gln Ser Ala Glu Ile Ser Asn Asp Leu
        675                 680                 685

Lys Ile Asp Ser Ser Thr Val Glu Arg Ile Glu Asp Ser His Ser Pro
        690                 695                 700

Gly Val Ala Val Ile Gln Phe Ala Val Gly Glu His Arg Ala Gln Val
705                 710                 715                 720

Ser Val Glu Val Leu Val Glu Tyr Pro Phe Phe Val Phe Gly Gln Gly
            725                 730                 735

Trp Ser Ser Cys Cys Pro Glu Arg Thr Ser Gln Leu Phe Asp Leu Pro
            740                 745                 750

Cys Ser Lys Leu Ser Val Gly Asp Val Cys Ile Ser Leu Thr Leu Lys
        755                 760                 765

Asn Leu Lys Asn Gly Ser Val Lys Lys Gly Gln Pro Val Asp Pro Ala
        770                 775                 780

Ser Val Leu Leu Lys His Ser Lys Ala Asp Gly Leu Ala Gly Ser Arg
785                 790                 795                 800

His Arg Tyr Ala Glu Gln Glu Asn Gly Ile Asn Gln Gly Ser Ala Gln
            805                 810                 815

Met Leu Ser Glu Asn Gly Glu Leu Lys Phe Pro Glu Lys Met Gly Leu
            820                 825                 830

Pro Ala Ala Pro Phe Leu Thr Lys Ile Glu Pro Ser Lys Pro Ala Ala
            835                 840                 845

Thr Arg Lys Arg Arg Trp Ser Ala Pro Glu Ser Arg Lys Leu Glu Lys
        850                 855                 860

Ser Glu Asp Glu Pro Pro Leu Thr Leu Pro Lys Pro Ser Leu Ile Pro
865                 870                 875                 880

Gln Glu Val Lys Ile Cys Ile Glu Gly Arg Ser Asn Val Gly Lys
            885                 890                 895
```

COMPOUND FOR TREATING NEURODEGENERATIVE DISORDERS

CROSS-REFERENCE TO RELATED APPLICATIONS

This application is a U.S. national stage filing, under 35 U.S.C. § 371(c), of International Application No. PCT/CN2020/078779, filed on Mar. 11, 2020, which claims priority to Chinese Patent Application No. 201910180674.7, filed on Mar. 11, 2019 and Chinese Patent Application No. 201911000198.2, filed Oct. 21, 2019, the entire contents of each of which are incorporated herein by reference.

FIELD OF THE INVENTION

The present invention relates to the biopharmaceutical field, and in particular to use of a compound with a substituted bicyclic structure, a pharmaceutically acceptable salt, stereoisomer, solvate, polymorph, tautomer, isotopic compound, metabolite or prodrug thereof in the preparation of a medicament for preventing or treating a polyglutamine (polyQ) related disorder.

BACKGROUND OF THE INVENTION

Neurodegenerative disorder refers to diseases caused by nervous system dysfunction resulted from abnormal death of central neurons. So far, there is no ultimate therapy that can slow down its development. Many neurodegenerative disorders are caused by proteins with unknown activity. Currently, methods that may be used to control protein levels, such as biological tools like RNAi, CRIPSR. etc. are difficult to deliver, especially to the nervous system.

A feasible treatment strategy is to use low molecular weight compounds (compounds for short) to control the level of proteins that affect diseases. An emerging approach is to enhance the ubiquitination of disease-causing proteins and target them to the proteasome degradation pathway using proteolysis-targeting chimera (PROTAC) technology, but this method relies on certain E3 ligases, which may not be present in diseased cells. Moreover, the protein degradation ability of the proteasome is limited, and the degradation efficiency of certain large disease proteins or aggregates that cause neurodegenerative disorder is low. As an important protein degradation pathway, autophagy is ubiquitous in eukaryotic cells, with strong protein degradation ability but low selectivity. Some studies increase protein degradation by enhancing autophagy, but this method lacks specificity.

PolyQ-related neurodegenerative disorder is a type of neurodegenerative disorder caused by mutant proteins, which can be effectively treated by reducing the level of mutant proteins. Taking Huntington's disease (HD), the most common neurodegenerative disorder, as an example, it is a monogenetic disorder wherein the mutation in the CAG repeat region of the exon 1 of the HTT gene located in the patient's chromosome 4 results in the expansion of the polyglutamine (polyQ) of the synthesized mutant protein (mHTT). mHTT is susceptible to shearing and aggregating, and causes toxicity which eventually leads to dysfunction and death of specific neuron. The current methods for controlling mHTT levels through low molecular weight compounds lack specificity, and may cause side effects. Furthermore, these methods are nonallele-selective and unable to distinguish between mHTT and wild-type HTT protein (wtHTT), which will lead to a decrease in the level of wtHTT which has important biological functions.

Similarly, take spinocerebellar ataxia type 3 (SCA3; also known as Machado-Joseph disease, MJD) as an example, which is the most common autosomal dominant spinocerebellar ataxia and is second only to HD as a common polyQ-related disorder in the world. SCA3 is caused by the abnormally expanded polyQ at the C-terminus of the coded protein ATXN3 resulting from the increase in the number of CAG repeats of the Ataxin-3 gene (ATXN3; also known as the MJD1 gene). Some studies have used siRNA, antisense oligonucleotides and other means to act on ATXN3 to reduce the expression of mutant ATXN3 protein and it is confirmed that the reduction in the level of mutant ATXN3 protein can produce therapeutic effects (Wang, Neuroscience, 371, 2018, 138-154). Some studies have focused on controlling the level of mutant ATXN3 protein through low molecular weight compounds. Studies on enhancing autophagy by compounds such as Menzies et al. Brain 2010, 133:93-104; studies on reducing the level of mutant ATXN3 protein by regulating other targets such as Costa M D, Brain, 2016, 139(11)2891-2908. But these studies have not satisfactorily solved the problem of specificity.

DISCLOSURE OF THE INVENTION

In one aspect, the present invention provides use of a compound of formula (I), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder

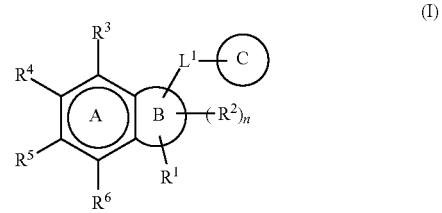

(I)

wherein:
ring A is a benzene ring;
ring B is a saturated or unsaturated 5- or 6-membered heterocycle, the heterocycle contains 1, 2 or 3 heteroatoms each independently selected from N, O and S;
ring C is selected from $C_{6-10}$ aryl and 5- to 10-membered heteroaryl, wherein the aryl or heteroaryl is optionally substituted with one or more substituents each independently selected from $R^{X1}$;
$L^1$ is a bond, or $C_{1-6}$ a hydrocarbon chain;
or ring C is absent, and $L^1$ is absent;
$R^1$ is =Y, wherein Y is O or S, or $OR^7$;
at each occurrence, $R^2$ is each independently selected from hydrogen, halogen, —$NO_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl-$C_{1-4}$ alkyl, 5- to 10-membered heteroaryl-$C_{1-4}$ alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)(O$R^{a1}$)O$R^{b1}$, —C(=$NR^{a1}$)$NR^{b1}R^{c1}$, —OCN, —SCN, —N=C=O and —NCS, wherein the alkyl, alkenyl, alkynyl, cyclohydrocarbyl, heterocyclyl, aryl or heteroaryl is optionally substituted with one or more substituents selected from halogen, —NO$_2$, —CN, C$_{1-8}$ alkyl, C$_{2-8}$ alkenyl, C$_{2-8}$ alkynyl, =O, =S, —OR$^{a2}$, —SR$^{a2}$, —NR$^{a2}$R$^{b2}$, —C(=O)OR$^{a2}$, —C(=O)NR$^{a2}$R$^{b2}$, —C(=O)R$^{a2}$, —S(=O)$_2$OR$^{a2}$, —S(=O)$_2$R$^{a2}$, —S(=O)$_2$NR$^{a2}$R$^{b2}$, —S(=O)R$^{a2}$ and —C(=NR$^{a2}$)NR$^{b2}$R$^{c2}$;

R$^3$, R$^4$, R$^5$, R$^6$ are each independently selected from H and R$^{X2}$;

at each occurrence, R$^{X1}$ and R$^{X2}$ are each independently selected from halogen, —NO$_2$, —CN, C$_{1-6}$ alkyl, C$_{2-6}$ alkenyl, C$_{2-6}$ alkynyl, —OR$^7$, —SR$^7$, —NR$^7$R$^8$, —C(=O)OR$^7$, —C(=O)NR$^7$R$^8$, —OC(=O)R$^7$, —NC(=O)R$^7$R$^8$, —C(=O)R$^7$, —S(=O)$_2$OR$^7$, —S(=O)$_2$R$^7$, —S(=O)$_2$NR$^7$R$^8$, —OS(=O)$_2$R$^7$, —NS(=O)$_2$R$^7$R$^8$ and —S(=O)R$^7$, wherein the alkyl, alkenyl or alkynyl are optionally substituted with one or more substituents selected from halogen, —NO$_2$, —CN, —OH, —O(C$_{1-6}$ alkyl), —O(C$_{3-6}$ cyclohydrocarbyl), —O(C$_{1-4}$ alkylene-C$_{3-6}$ cyclohydrocarbyl), —O(3- to 7-membered heterocyclyl), —O(C$_{1-4}$ alkylene)-(3- to 7-membered heterocyclyl), —SH, —S(C$_{1-6}$ alkyl), —S(C$_{3-6}$ cyclohydrocarbyl), —S(C$_{1-4}$ alkylene-C$_{3-6}$ cyclohydrocarbyl), —S(3- to 7-membered heterocyclyl), —S(C$_{1-4}$ alkylene)-(3- to 7-membered heterocyclyl), —NH$_2$, —NH(C$_{1-6}$ alkyl), —N(C$_{1-6}$ alkyl)$_2$, —NH(C$_{3-6}$ cyclohydrocarbyl), —N(C$_{3-6}$ cyclohydrocarbyl)$_2$, —NH(C$_{1-4}$ alkylene-C$_{3-6}$ cyclohydrocarbyl), —N(C$_{1-4}$ alkylene-C$_{3-6}$ cyclohydrocarbyl)$_2$, —NH(3- to 7-membered heterocyclyl), —N(3- to 7-membered heterocyclyl)$_2$, —NH(C$_{1-4}$ alkylene-3- to 7-membered heterocyclyl), —N(C$_{1-4}$ alkylene-3- to 7-membered heterocyclyl)$_2$, =O, —COOH and C$_{1-6}$ alkyl;

at each occurrence, R$^7$, R$^8$ are each independently selected from H, C$_{1-6}$ alkyl, C$_{2-6}$ alkenyl, C$_{2-6}$ alkynyl, C$_{3-6}$ cyclohydrocarbyl, C$_{3-6}$ cyclohydrocarbyl-C$_{1-4}$ alkyl, 3- to 7-membered heterocyclyl, 3- to 7-membered heterocyclyl-C$_{1-4}$ alkyl and C$_{6-10}$ aryl-C$_{1-4}$ alkyl, wherein the alkyl, alkenyl, alkynyl, cyclohydrocarbyl, heterocyclyl or aryl are optionally substituted with one or more substituents selected from halogen, —NO$_2$, —CN, C$_{1-6}$ alkyl, —OH, —O(C$_{1-6}$ alkyl), —NH$_2$, —NH(C$_{1-6}$ alkyl), —N(C$_{1-6}$ alkyl)$_2$, —COOH, —C(=O)O(C$_{1-6}$ alkyl), —C(=O)NH(C$_{1-6}$ alkyl), —C(=O)N(C$_{1-6}$ alkyl)$_2$, —OC(=O)(C$_{1-6}$ alkyl), —NHC(=O)(C$_{1-6}$ alkyl) and —C(=O)(C$_{1-6}$ alkyl);

at each occurrence, R$^{a1}$, R$^{b1}$, R$^{c1}$, R$^{a2}$, R$^{b2}$, R$^{c2}$ are each independently selected from H, C$_{1-6}$ alkyl, C$_{2-6}$ alkenyl, C$_{2-6}$ alkynyl, C$_{3-6}$ cyclohydrocarbyl, C$_{3-6}$ cyclohydrocarbyl-C$_{1-4}$ alkyl, 3 to 7-membered heterocyclyl, 3- to 7-membered heterocyclyl-C$_{1-4}$ alkyl, C$_{6-10}$ aryl, C$_{6-10}$ aryl-C$_{1-4}$ alkyl, 5- to 10-membered heteroaryl, 5- to 10-membered heteroaryl-C$_{1-4}$ alkyl, —OR$^{Y1}$, —SR$^{Y1}$, —NR$^{Y1}$R$^{Y2}$, —C(=O)OR$^{Y1}$, —C(=O)NR$^{Y1}$R$^{Y2}$, —C(=O)R$^{Y1}$, —S(=O)$_2$OR$^{Y1}$, —S(=O)$_2$R$^{Y1}$, —S(=O)$_2$NR$^{Y1}$R$^{Y2}$ and —S(=O)R$^{Y1}$, wherein the alkyl, alkenyl, alkynyl, cyclohydrocarbyl, heterocyclyl, aryl or heteroaryl are optionally substituted with one or more substituents selected from halogen, =O, =S, —OR$^{Y3}$, —SR$^{Y3}$, —NR$^{Y3}$R$^{Y4}$, —C(=O)R$^{Y3}$, —C(=O)OR$^{Y3}$ and —C(=O)NR$^{Y3}$R$^{Y4}$;

at each occurrence, R$^{Y1}$, R$^{Y2}$, R$^{Y3}$, R$^{Y4}$ are each independently selected from H, C$_{1-8}$ alkyl, C$_{3-10}$ cyclohydrocarbyl, C$_{3-10}$ cyclohydrocarbyl-C$_{1-4}$ alkyl, 3- to 10-membered heterocyclyl, 3 to 10-membered heterocyclyl-C$_{1-4}$ alkyl, C$_{6-10}$ aryl, C$_{6-10}$ aryl-C$_{1-4}$ alkyl, 5- to 10-membered heteroaryl, and 5- to 10-membered heteroaryl-C$_{1-4}$ alkyl, wherein the alkyl, alkenyl, alkynyl, cyclohydrocarbyl, heterocyclyl, aryl or heteroaryl are optionally substituted with one or more substituents independently selected from halogen, —NO$_2$, —CN, C$_{1-8}$ alkyl, C$_{2-8}$ alkenyl, C$_{2-8}$ alkynyl, —OH, —SH, —NH$_2$, =O and —COOH;

n is 1 or 2;

provided that the compound of formula (I) does not include the following structure:

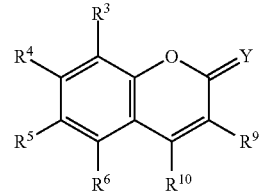

wherein R$^3$ is selected from —O(C$_{1-6}$ alkyl) and —O(C$_{1-4}$ alkylene-C$_{6-10}$ aryl); R$^{10}$ is H;

and the compound of formula (I) does not include the following structure:

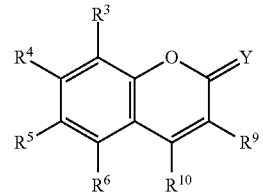

wherein R$^4$ is —O(C$_{1-6}$ alkyl); R$^5$ is halogen; R$^{10}$ is CF$_3$;

and the compound of formula (I) does not include the following structure:

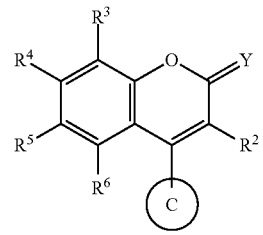

wherein R$^4$ is selected from —O(C$_{1-6}$ alkyl) and —O(C$_{1-4}$ alkylene-C$_{6-10}$ aryl);

ring C is C$_{6-10}$ aryl, which is optionally substituted with one or more substituents each independently selected from R$^{X1}$;

and the compound of formula (I) does not include the following structure:

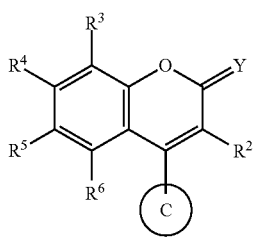

wherein $R^4$ is selected from —OH and —O($C_{1-6}$ alkyl); $R^5$ is halogen; Ring C is 5- to 10-membered heteroaryl, which is optionally substituted with one or more substituents each independently selected from $R^{X1}$.

In one embodiment, the neurodegenerative disorder is spinocerebellar ataxia (such as type 1, 2, 3, 6, 7, 12, 17), dentatorubral-pallidoluysian atrophy, Huntington's disease, Huntington's disease-like syndrome-2 or spinal-bulbar muscular atrophy, especially Huntington's disease.

DETAILED DESCRIPTION

Figure 1:
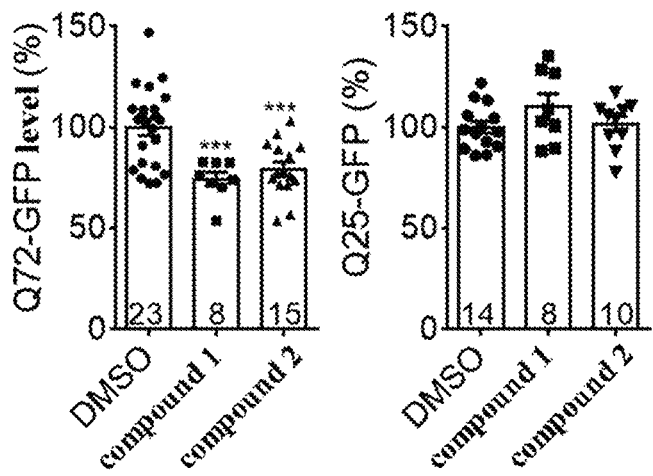
FIG. 1. Effects of compounds on the level of proteins containing polyglutamine in HEK293T cells.

Unless defined otherwise, all technical and scientific terms used herein have the same meaning as is commonly understood by one of skill in the art. If there is a contradiction, the definition provided in this application shall prevail. When a trade name is present herein, it refers to the corresponding commodity or the active ingredient thereof. All patents, published patent applications and publications cited herein are incorporated herein by reference.

General Terminology and Definitions

Unless defined otherwise, all technical and scientific terms used herein have the same meaning as is commonly understood by one of skill in the art. If there is a contradiction, the definition provided in this application shall prevail. When a trade name is present herein, it refers to the corresponding commodity or the active ingredient thereof. All patents, published patent applications and publications cited herein are incorporated herein by reference.

The terms "including", "comprising", "having", "containing", or "relating to" and other variants thereof, as used herein, are inclusive or open-ended, and not exclusive of other elements or steps of methods that are not enumerated. Those skilled in the art should understand that the above terms such as "include" also cover the meaning of "consist of".

The term "one or more" or the similar expression "at least one" can mean, for example, 1, 2, 3, 4, 5, 6, 7, 8, 9, 10 or more.

When the lower limit and the upper limit of a numerical range are disclosed, any numerical value and any included range falling within the range are specifically disclosed. In particular, each value range of the values disclosed herein should be understood to mean each value and range covered in a wider range. For example, the expression "ATXN1 with polyQ length ≥40" can cover the case where the polyQ length ≥41. For example, "ATXN2 with polyQ length ≥33" can cover the case where the polyQ length ≥34. For example, "ATXN3 with polyQ length ≥41" can cover the case where the polyQ length ≥62 and can cover the case where the polyQ length is 74, for example. For example, "ATXN3 with polyQ length ≤41" can cover the case where the polyQ length is 27. For example, "ATXN7 with polyQ length ≥19" can cover the case where the polyQ length ≥38. For example, "TBP with polyQ length ≥44" can cover the case where the polyQ length ≥45. For example, "ATN1 with polyQ length ≥39" can cover the case where the polyQ length ≥49. For example, "HTT with a polyQ length ≥36" can cover the case where the polyQ length is 47, 49, 55, 68, 72, 73, 111, 128, or 140. For another example, "HTT with polyQ length <36" can cover the case where the polyQ length is 7, 16, 19, 23, or 25. For example, "AR with polyQ length ≥37" can cover the case where the polyQ length ≥38.

The expression m-n used as used herein refers to the range from m to n and the subrange composed of each point value and each point value. For example, the expression "$C_1$-$C_8$" or "$C_{1-8}$" covers the range of 1-8 carbon atoms and should be understood to also cover any subrange and each point value, such as $C_2$-$C_5$, $C_3$-$C_4$, $C_1$-$C_2$, $C_1$-$C_3$, $C_1$-$C_4$, $C_1$-$C_5$, $C_1$-$C_6$, $C_1$-$C_7$, etc., and $C_1$, $C_2$, $C_3$, $C_4$, $C_5$, $C_6$, $C_7$, $C_8$, etc. For example, the expression "$C_3$-$C_{10}$" or "$C_{3-10}$" should also be understood in a similar manner, for example, it can cover any subrange and point value contained therein, such as $C_3$-$C_9$, $C_6$-$C_9$, $C_6$-$C_8$, $C_6$-$C_7$, $C_7$-$C_{10}$, $C_7$-$C_9$, $C_7$-$C_8$, $C_8$-$C_9$, etc., and $C_3$, $C_4$, $C_5$, $C_6$, $C_7$, $C_8$, $C_9$, $C_{10}$, etc. For another example, the expression "3- to 10-membered" should be understood as covering any subrange and each point value, such as 3- to 5-membered, 3- to 6-membered, 3- to 7-membered, 3- to 8-membered, 4- to 5-membered, 4- to 6-membered, 4- to 7-membered, 4- to 8-membered, 5- to 7-membered, 5- to 8-membered, 6- to 7-membered, 6- to 8-membered, 9- to 10-membered, etc., and 3-, 4-, 5-, 6-, 7-, 8-, 9-, 10-membered, etc. Other similar expressions as used herein should also be understood in a similar way.

The term "optional" or "optionally" means that the event or situation described later may or may not occur, and the description includes occurrence of said event or situation and non-occurrence of said event or situation.

The terms "substitute" and "substituted" mean that one or more (e.g. one, two, three, or four) hydrogens are replaced by a selection from the indicated group, provided that not exceeding the normal valence of the designated atom under the circumstance and the substitution forms a stable compound. Combinations of substituents and/or variables are only allowed when the combination forms a stable compound. When describing that a substituent is absent, it should be understood that the substituent can be one or more hydrogen atoms, provided that the structure can result in a stable state of the compound.

If a substituent is described as "optionally substituted", the substituent may be unsubstituted or may be substituted. If an atom or group is described as being optionally substituted by one or more substituents on a list, one or more hydrogens on the atom or group can be optionally replaced by substituents which are selected independently. When the substituent is oxo (i.e., =O), it means that two hydrogen atoms are replaced.

Unless otherwise specified, as used herein, the point of attachment of a substituent can be from any suitable position of the substituent. When a bond of a substituent is shown to pass through a bond connecting two atoms in a ring, such substituent can bond to any of the ring-forming atoms in the substitutable ring.

When any variable (such as R), as well as variables with superscripts or subscripts (such as $R^{X1}$, $R^{X2}$, $R^7$, $R^8$, $R^{a1}$, $R^{b1}$, $R^{c1}$, $R^{a1}$, $R^{b1}$, $R^{c2}$, etc.) appear more than once in the composition or structure of the compound, its definition in each case is independent at each occurrence. For example, if a group is substituted with 0, 1, 2, 3, or 4 R substituents, the group may optionally be substituted with up to four R substituents, and all the options of R substituent are all independent of each other.

The term "halo" or "halogen" or "halogenated" should be understood to mean fluorine (F), chlorine (Cl), bromine (Br) or iodine (I) atoms, preferably fluorine, chlorine, bromine atoms.

The term "alkyl" refers to a straight or branched saturated aliphatic hydrocarbon group composed of carbon atoms and hydrogen atoms, which is connected to the rest of the molecule by a single bond. "Alkyl" may have 1-8 atoms, referring to "$C_1$-$C_8$ alkyl", for example, $C_{1-4}$ alkyl, $C_{1-3}$ alkyl, $C_{1-2}$ alkyl, $C_3$ alkyl, $C_4$ alkyl, $C_{1-6}$ alkyl, $C_{3-6}$ alkyl. Non-limiting examples of alkyl groups include, but are not limited to methyl, ethyl, propyl, butyl, pentyl, hexyl, isopropyl, isobutyl, sec-butyl, tert-butyl, isopentyl, 2-methylbutyl, 1-methylbutyl 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or their isomers.

The term "alkylene", when used alone or in combination with other groups herein, refers to a straight or branched saturated divalent hydrocarbon group. For example, the term "$C_{1-6}$ alkylene" refers to an alkylene having 1-6 carbon atoms, for example, methylene, ethylene, propylene, butylene, pentylene, hexylidene, 1-methylethylene, 2-methylethylene, methylpropylene or ethylpropylene, etc.

The term "alkenyl" refers to a straight or branched unsaturated aliphatic hydrocarbon group consisting of carbon atoms and hydrogen atoms with at least one double bond. The alkenyl group may have 2-8 carbon atoms, referring to, "$C_{2-8}$ alkenyl", for example, $C_2$ alkenyl, $C_{3-4}$ alkenyl. Non-limiting examples of alkenyl groups include, but are not limited to ethenyl, allyl, (E)-2-methylethenyl, (Z)-2-methylethenyl, (E)-but-2-enyl, (Z)-but-2-enyl, (E)-but-1-enyl, (Z)-but-1-enyl, etc.

The term "alkynyl" refers to a straight or branched unsaturated aliphatic hydrocarbon group with at least one triple bond consisting of carbon atoms and hydrogen atoms. The alkynyl group may have 2-8 carbon atoms, referring to "$C_{2-8}$ alkynyl", for example, $C_{2-4}$ alkynyl, $C_{3-4}$ alkynyl. Non-limiting examples of alkynyl groups include, but are not limited to ethynyl, prop-1-ynyl, prop-2-ynyl, but-1-ynyl, but-2-ynyl, but-3-ynyl, etc.

The term "cyclohydrocarbyl" refers to a saturated or unsaturated non-aromatic cyclic hydrocarbon group composed of carbon atoms and hydrogen atoms, preferably containing 1 or 2 rings. The said cyclohydrocarbyl may be a monocyclic ring, a fused polycyclic ring, a bridged ring or a spiro ring structure. The cyclohydrocarbyl group may have 3-10 carbon atoms, i.e. "$C_{3-10}$ cyclohydrocarbyl", for example, $C_{3-8}$ cyclohydrocarbyl, $C_5$ cyclohydrocarbyl, $C_6$ cyclohydrocarbyl, $C_7$ cyclohydrocarbyl. Non-limiting examples of cyclohydrocarbyl include, but are not limited to, cyclopropyl, cyclobutyl, cyclopentyl, cyclohexyl, cycloheptyl, bicyclo[2.2.1]heptyl and spiro[3.3]heptyl, etc. The term also covers situations where the C atom can be substituted by oxo (=O).

The term "heterocyclyl" or "heterocyclic hydrocarbon group" refers to a monocyclic or bicyclic ring system having, for example, 3-10 (suitably 3-8, more suitably 3-7, especially 4-6) ring atoms (3- to 10-membered, 3- to 8-membered, 3- to 7-membered, 3- to 6-membered), in which at least one ring atoms (for example, 1, 2 or 3) are heteroatoms selected from N, O and S, and the remaining ring atoms are C. The ring system can be saturated (also can be understood as the corresponding "heterocycloalkyl") or unsaturated (i.e., having one or more double bonds and/or triple bonds in the ring). "Heterocyclyl" or "heterocyclic hydrocarbon group" does not possess aromaticity. The term also covers situations where the C atom can be substituted with oxo (=O) and/or the S atom on the ring can be substituted with 1 or 2 oxo (=O).

The heterocyclyl may be, for example, a 4-membered ring, such as azetidinyl, oxetanyl, or a 5-membered ring, such as tetrahydrofuranyl, dioxolinyl, pyrrolidinyl, imidazolidinyl, pyrazolidinyl, pyrrolinyl, oxopyrrolidinyl, 2-oxo-imidazolidin-1-yl; or 6-membered ring, such as tetrahydropyranyl, piperidinyl, morpholinyl, dithianyl, thiomorpholinyl, piperazinyl, 1,1-dioxo-1,2-thiazinan-2-yl or trithianyl; or a 7-membered ring, such as a diazepine ring. Optionally, the heterocyclyl can be benzo-fused.

The heterocyclyl may be bicyclic without limitation, for example, a 5-membered fused 5-membered ring, such as hexahydrocyclopentane[c]pyrrole-2(1H)-yl; or a 5-membered fused 6-membered bicyclic ring, such as hexahydropyrrolo[1,2-a]pyrazine-2(1H)-yl.

As mentioned above, the heterocycle may be unsaturated; that is to say, it may contain one or more double bonds without limitation. For example, an unsaturated heterocycle containing a nitrogen atom may be 1,6-dihydropyrimidine, 1,2-dihydropyrimidine, 1,4-dihydropyrimidine, 1,6-dihydropyridine, 1,2-dihydropyridine, 1,4-dihydropyridine, 2,3-dihydro-1H-pyrrole, 3,4-dihydro-1H-pyrrole, 2,5-dihydro-1H-pyrrolyl, 4H-[1,3,4]thiadiazinyl, 4,5-dihydrooxazolyl or 4H-[1,4] thiazinyl ring. An unsaturated heterocycle containing an oxygen atom may be 2H-pyran, 4H-pyran, or 2,3-dihydrofuran, and the unsaturated heterocycle containing a sulfur atom may be 2H-thiopyran or 4H-thiopyran. The heterocycle can be benzo-fused, but not limited thereto, such as dihydroisoquinolinyl ring.

The term "aryl" refers to an all-carbon monocyclic or fused polycyclic (such as bicyclic) aromatic ring group with a conjugated π-electron system. For example, aryl may have 6-14 carbon atoms, suitably 6-10, more suitably 6 or 10. Examples of aryl include, but are not limited to, phenyl, naphthyl, anthracenyl, etc.

The term "heteroaryl" should be understood to preferably mean a monovalent monocyclic, bicyclic, or tricyclic aromatic ring system having 5, 6, 7, 8, 9 or 10 ring atoms ("5- to 10-membered heteroaryl"), especially 5 or 6 or 9 or 10 ring atoms, and at least one (suitably 1-4, more suitably 1, 2 or 3) of the ring atoms are heteroatoms such as oxygen, nitrogen, or sulfur. The heteroatoms may be the same with or different from each other. In addition, the heteroaryl can be benzo-fused in each case. In particular, the heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl, etc., and their benzo derivatives, such as benzofuranyl, benzothienyl, benzoxazolyl, benzisoxazolyl, benzimidazolyl, benzotriazolyl, indazole, indolyl, isoindolyl, etc.; or pyridyl, pyridazinyl, pyrimidinyl, pyrazinyl, triazinyl, etc., and their benzo-fused derivatives, such as quinolinyl, quinazolinyl, isoquinolinyl, etc., or azocinyl, indolizinyl, purinyl, etc., and their benzo derivatives; or cinnolinyl, phthalazinyl, quinazolinyl, quinoxalinyl, naphthyridinyl, carbazolyl, acridinyl, etc.

The term "$C_1$-$C_6$ hydrocarbon chain" refers to a chain-like group composed of carbon atoms and hydrogen atoms, which may be straight or branched, and contains 1-8 (especially 1-5, such as 1, 2, 3, 4 or 5) carbon atoms. The hydrocarbon chain can be saturated (i.e., $C_1$-$C_6$ alkylene) or unsaturated; that is to say, it may contain one or more (preferably one) carbon-carbon double bond or triple bond.

The alkylene may have 1-8 carbon atoms, referring to "$C_{1-6}$ alkylene", such as $C_{1-5}$ alkylene, $C_{1-4}$ alkylene, $C_{1-3}$ alkylene, $C_{1-2}$ alkylene, $C_3$ alkylene, and $C_1$ alkylene, i.e., methylene. Non-limiting examples of alkylene include but are not limited to methylene (—$CH_2$—), 1,1-ethylene (—CH($CH_3$)—), 1,2-ethylene (—$CH_2CH_2$—), 1,1-propylene (—CH($CH_2CH_3$)—), 1,2-propylene (—$CH_2$CH($CH_3$)—), 1,3-propylene (—$CH_2CH_2CH_2$—), 1,4-butylene (—$CH_2CH_2CH_2CH_2$—) etc.

The term "neurodegenerative disorder" refers to a disease caused by the loss or pathological change of neurons and/or their myelin sheaths. Characteristic pathological structures, such as insoluble aggregates of protein, can be observed in the brain neurons of patients with neurodegenerative disorders. Insoluble aggregates may produce cytotoxicity, further leading to neuron loss and disease.

The term "polyQ" or "polyglutamine" refers to the polyglutamine tract contained by the protein. Glutamine is encoded by cytosine-adenine-guanine (CAG) in the gene. The length of the polyglutamine is related to the number of CAG repeats in gene exons. Therefore, the increase in the number of CAG repeats in gene exons result in polyglutamine expansions in the synthesized protein. Proteins with abnormally expanded polyQ are known to be associated with some neurodegenerative disorder. As used herein, the gene name can use the form of "Q+number" to indicate the number of CAG repeats in exons, such as Q25 or Q72, which respectively indicate 25 repeats or 72 repeats of CAG in exons. In the protein name, the length of the polyglutamine can be expressed in the form of "Q+number" as above, such as Q27 or Q73, which means that the length of the polyglutamine is 27 Q (glutamine) or 73 Q, respectively. The CAG repetitions or glutamine repetitions indicated in the form of "Q+number" herein are all continuous repetitions. Unless otherwise specified, the length of polyQ as used herein refers to the length of the continuous polyglutamine.

The term "polyQ-related neurodegenerative disorder" refers to a neurodegenerative disorder associated with abnormal expansion of polyQ, or a neurodegenerative disorder that responds to levels of proteins containing expanded polyQ. Neurodegenerative disorders are a group of disorders with clinical and genetic heterogeneity.

"Normal polyQ" refers to the polyQ of a protein in a normal physiological state that has a length less than a specific number. Correspondingly, "abnormally expanded" means that the polyQ of the protein has a length longer than the normal length. For diseases or pathological conditions, the length of polyQ is longer. As an example, polyQ-related neurodegenerative disorders include but are not limited to spinocerebellar ataxia (SCA) type 1 (polyQ length ≥41), type 2 (polyQ length ≥34), type 3 (polyQ length ≥62), type 7 (polyQ length ≥38), type 12 (polyQ length ≥46), type 17 (polyQ length ≥45); and dentatorubral-pallidoluysian atrophy (DRPLA, polyQ length ≥49), Huntington's disease (HD, polyQ length ≥36) and spinal-bulbar muscular atrophy (SBMA, polyQ length ≥38). These diseases are caused by the expansion of CAG repeat regions on ATXN1, ATXN2, ATXN3, ATXN7, ATXN12, TBP, ATN1, HTT and AR genes, respectively (Lesley Jones et al., DNA repair in the trinucleotide repeat disorders, Lancet Neurol. 2017; 16: 88-96). Among them, spinocerebellar ataxia type 3 (SCA3, also known as Machado-Joseph disease, MJD) is the most common autosomal dominant spinocerebellar ataxia and is second only to HD as a common polyQ-related disorder in the world. SCA3 is caused by the abnormally expanded polyQ at the C-terminus of the coded protein ATXN3 resulting from the increase in the number of CAG repeats of the Ataxin-3 gene (ATXN3; also known as the MJD1 gene). Examples of normal polyQ proteins described herein include, but are not limited to, ATXN1 with polyQ length <40, ATXN2 with polyQ length <33, ATXN3 with polyQ length <41, ATXN7 with polyQ length <19, ATXN12 with polyQ length <46, TBP with polyQ length <44, ATN1 with polyQ length <39, HTT with polyQ length <36, and AR with polyQ length <37. Correspondingly, examples of the proteins with abnormally expanded polyQ described herein include, but are not limited to, ATXN1 with polyQ length ≥40, ATXN2 with polyQ length ≥33, ATXN3 with polyQ length ≥41, ATXN7 with polyQ length ≥19, and ATXN12 with polyQ length ≥46, TBP with polyQ length ≥44, ATN1 with polyQ length ≥39, HTT with polyQ length ≥36, and AR with polyQ length ≥37.

The term "pharmaceutically acceptable" refers to that when contacted with the patient's tissue within the scope of normal medical judgment, no undue toxicity, irritation, allergic reactions, etc. shall arise, having reasonable advantage-disadvantage ratios and effective for the intended use.

The pharmaceutically acceptable salts of the compound of the present invention include acid addition salts and base addition salts thereof. Suitable acid addition salts are formed from acids that form pharmaceutically acceptable salts. Examples include hydrochloride, acetate, aspartate, benzoate, bicarbonate/carbonate, glucoheptonate, gluconate, nitrate, orotate, palmitic acid salt and other similar salt. Suitable base addition salts are formed from bases that form pharmaceutically acceptable salts. Examples include aluminum salts, arginine salts, choline salts, magnesium salts, and other similar salts. The method for preparing the pharmaceutically acceptable salt of the compound of the present invention is known to those skilled in the art.

The compound of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and their racemic mixtures and other mixtures, for example, mixtures enriched in enantiomers or diastereomers, all of which are within the scope of the present invention. There may be other asymmetric carbon atoms in substituents such as alkyl. All these isomers and their mixtures are included in the scope of the present invention. In some embodiments, the preferred compounds are those isomeric compounds that show better biological activity. Purified or partially purified isomers and stereoisomers, or racemic mixtures or diastereomeric mixtures of the compound of the present invention are also included in the scope of the present invention. The purification and separation of such substances can be achieved by standard techniques known in the art.

Optically pure enantiomers can be obtained by resolving racemic mixtures according to conventional methods, for example, by using optically active acids or bases to form diastereomeric salts, or by forming covalent diastereomers. A mixture of diastereomers can be separated into single diastereomers based on their physical and/or chemical differences by methods known in the art (for example, by chromatography or fractional crystallization). Then, release the optically active enantiomeric base or acid from the separated diastereomeric salt. Another method for separating racemic enantiomers can use chiral chromatography (such as a chiral HPLC column). The separated chiral isomers can be subjected to conventional derivatization or non-derivatization before separation, depending on what method can achieve more effective separation of chiral isomers. Enzymatic methods can also be used to separate derivatized or underivatized chiral isomers. Similarly, optically active raw materials can be used to obtain the optically pure compound of the present invention through chiral synthesis.

In addition, the compound of the present invention may exist in the form of tautomers. The present invention includes all possible tautomers of the compound of the present invention, and also includes single tautomers or the form of any mixtures of said tautomers in any ratio.

The compound of the present invention may exist in the form of solvates (preferably hydrates), wherein the compound of the present invention contains a polar solvent as a structural element of the compound crystal lattice, especially for example water, methanol, or ethanol. The amount of polar solvents, especially water, can be present in stoichiometric or non-stoichiometric ratios.

The present invention also covers all possible crystalline forms or polymorphs of the compound of the present invention, which can be a single polymorph or a mixture of more than one polymorph in any ratio.

The present invention also contemplates all pharmaceutically acceptable isotopically-labeled compounds, which are identical to the compounds of the invention except that one or more atoms are replaced by the atom(s) of the same atomic number but having atomic mass or mass number different from the atomic mass or mass number prevailing in nature.

The metabolites of the compound of the present invention are also included within the scope of the present invention, namely the substances formed in the body when the compound of the present invention is administered. The metabolites of compounds can be identified by techniques known in the art, and their activity can be characterized by experimental methods. Such products can be produced, for example, by oxidation, reduction, hydrolysis, amidation, deamidation, esterification, enzymatic hydrolysis, etc. of the administered compound. Therefore, the present invention includes metabolites of the compound of the present invention, including compounds prepared by contacting the compound of the present invention with a mammal for a time sufficient to produce its metabolites.

The present invention further includes within its scope the prodrugs of the compound of the present invention, which are certain derivatives of the compound of the present invention that have less or no pharmacological activity themselves but when administered to or on the body, can be converted into the compound of the present invention with the desired activity by, for example, hydrolytic cleavage. Usually, such prodrugs will be functional group derivatives of the compound, which are easily converted into the desired therapeutically active compound in vivo. For a review of prodrugs and their preparation methods, see, for example, J. Rautio et al. Nature Reviews Drug Discovery (2008) 7, 255-270 and Prodrugs: Challenges and Rewards (V. Stella et al. ed. Springer, 2007). The prodrugs of the present invention can be prepared, for example, by replacing an appropriate functional group in the compound of the present invention with a certain moiety known to those skilled in the art as "pro-moiety".

The term "polymorphism" or "polymorph" refers to a single polymorph or a mixture of more than one polymorph in any ratio.

The term "crystal form" or "crystal" refers to any solid substance exhibiting a three-dimensional order, as opposed to an amorphous solid substance, which produces a characteristic X-ray powder diffraction pattern with sharp and defined peaks.

The term "amorphous" refers to any solid substance which lacks order in three dimensions.

The term "hydrate" describes a solvate containing a drug and a stoichiometric or non-stoichiometric amount of water.

The term "pharmaceutically acceptable carrier" refers to those substances that have no obvious stimulating effect on the organism and will not damage the biological activity and performance of the active compound. "Pharmaceutically acceptable carriers" include but are not limited to glidants, sweeteners, diluents, preservatives, dyes/colorants, flavors, surfactants, wetting agents, dispersants, disintegrants, stabilizer, solvent or emulsifier. Non-limiting examples of the carrier include calcium carbonate, calcium phosphate, various sugars and various starches, cellulose derivatives, gelatin, vegetable oils and polyethylene glycols, etc.

The term "administration" or "administrating" or the like refers to a method that enables a compound or composition to be delivered to a desired site of biological action. Such methods comprise but not limited to oral or parenteral (including intracerebroventricular, intravenous, subcutaneous, intraperitoneal, intramuscular, intravascular injection or infusion), local, rectal administration or the like. Especially injection or oral.

As used herein, The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "active ingredient", "therapeutic agent", "active substance" or "active agent" refer to a chemical entity that can effectively treat or prevent the target disorder, disease, or symptom.

For drugs, drug units or active ingredients, the terms "effective amount", "therapeutically effective amount" or "prophylactically effective amount" refer to an amount of a drug or agent that has acceptable side effects but is sufficient to achieve the desired effect. The effective amount may be determined individually and depends on the age and general condition of the receptor as well as specific active substance. The effective amount in specific case can be determined by a person skilled in the art through conventional test.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

The following detailed description of the invention is intended to illustrate non-limiting embodiments, so that others skilled in the art can more fully understand the technical solution of the present invention, its principles and practical applications, so that others skilled in the art can modify and implement the present invention in various manners so that it can be optimally adapted to the requirements of specific applications.

The Compound of the Present Invention and Use Thereof

In one aspect, the present invention provides use of a compound of formula (I), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder

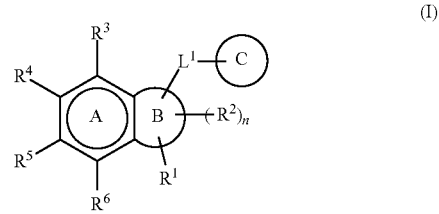

(I)

wherein:
ring A is a benzene ring;
ring B is a saturated or unsaturated 5- or 6-membered heterocycle, wherein the heterocycle contains 1, 2 or 3 heteroatoms each independently selected from N, O and S.
ring C is selected from $C_{6-10}$ aryl and 5- to 10-membered heteroaryl, wherein the aryl or heteroaryl is optionally substituted with one or more substituents each independently selected from $R^{X1}$.
$L^1$ is a bond, or a $C_{1-6}$ hydrocarbon chain;
or ring C is absent, and $L^1$ is absent;
$R^1$ is =Y, wherein Y is O or S, or $OR^7$;
at each occurrence, $R^2$ is each independently selected from hydrogen, halogen, —$NO_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl-$C_{1-4}$ alkyl, 5- to 10-membered heteroaryl-$C_{1-4}$ alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, C(=S)$R^{a1}$, P(=O)($OR^{a1}$)$OR^{b1}$, —C(=$NR^{a1}$)$NR^{b1}R^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, =O, =S, —$OR^{a2}$, —$SR^{a2}$, —$NR^{a2}R^{b2}$, —C(=O)$OR^{a2}$, —C(=O)$NR^{a2}R^{b2}$, C(=O)$R^{a2}$, S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;
$R^3$, $R^4$, $R^5$, $R^6$ are each independently selected from H and $R^{X2}$;
at each occurrence, $R^{X1}$ and $R^{X2}$ are each independently selected from halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl, alkenyl or alkynyl are optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O(C$_{1-4}$ alkylene)-(3- to 7-membered heterocyclyl), —SH, —S(C$_{1-6}$ alkyl), —S(C$_{3-6}$ cyclohydrocarbyl), —S(C$_{1-4}$ alkylene-C$_{3-6}$ cyclohydrocarbyl), —S(3- to 7-membered heterocyclyl), —S(C$_{1-4}$ alkylene)-(3- to 7-membered heterocyclyl), —NH$_2$, —NH(C$_{1-6}$ alkyl), —N(C$_{1-6}$ alkyl)$_2$, —NH(C$_{3-6}$ cyclohydrocarbyl), —N(C$_{3-6}$ cyclohydrocarbyl)$_2$, —NH(C$_{1-4}$ alkylene-C$_{3-6}$ cyclohydrocarbyl), —N(C$_{1-4}$ alkylene-C$_{3-6}$ cyclohydrocarbyl)$_2$, —NH(3- to 7-membered heterocyclyl), —N(3- to 7-membered heterocyclyl)$_2$, —NH(C$_{1-4}$ alkylene-3- to 7-membered heterocyclyl), —N(C$_{1-4}$ alkylene-3- to 7-membered heterocyclyl)$_2$, =O, —COOH and C$_{1-6}$ alkyl;

at each occurrence, R$^7$, R$^8$ are each independently selected from H, C$_{1-6}$ alkyl, C$_{2-6}$ alkenyl, C$_{2-6}$ alkynyl, C$_{3-6}$ cyclohydrocarbyl, C$_{3-6}$ cyclohydrocarbyl-C$_{1-4}$ alkyl, 3- to 7-membered heterocyclyl, 3- to 7-membered heterocyclyl-C$_{14}$ alkyl and C$_{6-10}$ aryl-C$_{1-4}$ alkyl, wherein the alkyl, alkenyl, alkynyl, cyclohydrocarbyl, heterocyclyl or aryl are optionally substituted with one or more substituents selected from halogen, —NO$_2$, —CN, C$_{1-6}$ alkyl, —OH, —O(C$_{1-6}$ alkyl), —NH$_2$, —NH(C$_{1-6}$ alkyl), —N(C$_{1-6}$ alkyl)$_2$, —COOH, —C(=O)O(C$_{1-6}$ alkyl), —C(=O)NH(C$_{1-6}$ alkyl), —C(=O)N(C$_{1-6}$ alkyl)$_2$, —OC(=O)(C$_{1-6}$ alkyl), —NHC(=O)(C$_{1-6}$ alkyl) and —C(=O)(C$_{1-6}$ alkyl);

at each occurrence, R$^{a1}$, R$^{b1}$, R$^{c1}$, R$^{a2}$, R$^{b2}$, R$^{c2}$ are each independently selected from H, C$_{1-6}$-alkyl, C$_{2-6}$ alkenyl, C$_{2-6}$ alkynyl, C$_{3-6}$ cyclohydrocarbyl, C$_{3-6}$ cyclohydrocarbyl-C$_{1-4}$ alkyl, 3- to 7-membered heterocyclyl, 3- to 7-membered heterocyclyl-C$_{14}$ alkyl, C$_{6-10}$ aryl, C$_{6-10}$ aryl-C$_{1-4}$ alkyl, 5- to 10-membered heteroaryl, 5- to 10-membered heteroaryl-C$_{1-4}$ alkyl, —OR$^{y1}$, —SR$^{y1}$, —NR$^{y1}$R$^{y2}$, —C(=O)OR$^{y1}$, —C(=O)NR$^{y1}$R$^{y2}$, —C(=O)R$^{y1}$, —S(=O)$_2$OR$^{y1}$, —S(=O)$_2$R$^{y1}$, —S(=O)$_2$NR$^{y1}$R$^{y2}$ and —S(=O)R$^{y1}$, wherein the alkyl, alkenyl, alkynyl, cyclohydrocarbyl, heterocyclyl, aryl or heteroaryl are optionally substituted with one or more substituents independently selected from halogen, =O, =S, —OR$^{y3}$, —SR$^{y3}$, —NR$^{y3}$R$^{y4}$, —C(=O)R$^{y3}$, —C(=O)OR$^{y3}$ and —C(=O)NR$^{y3}$R$^{y4}$;

at each occurrence, R$^{y1}$, R$^{y2}$, R$^{y3}$, R$^{y4}$ are each independently selected from H, C$_{1-8}$ alkyl, C$_{3-10}$ cyclohydrocarbyl, C$_{3-10}$ cyclohydrocarbyl-C$_{1-4}$ alkyl, 3- to 10-membered heterocyclyl, 3- to 10-membered heterocyclyl-C$_{1-4}$ alkyl, C$_{6-10}$ aryl, C$_{6-10}$ aryl-C$_{1-4}$ alkyl, 5- to 10-membered heteroaryl, and 5- to 10-membered heteroaryl-C$_{1-4}$ alkyl, wherein the alkyl, alkenyl, alkynyl, cyclohydrocarbyl, heterocyclyl, aryl or heteroaryl are optionally substituted with one or more substituents selected from halogen, —NO$_2$, —CN, C$_{1-8}$ alkyl, C$_{2-8}$ alkenyl, C$_{2-8}$ alkynyl, —OH, —SH, —NH$_2$, =O and —COOH;

n is 1 or 2;

provided that the compound of formula (I) does not include the following structure:

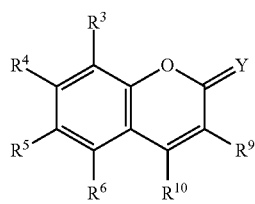

wherein R$^3$ is selected from —O(C$_{1-6}$ alkyl) and —O(C$_{1-4}$ alkylene-C$_{6-10}$ aryl); R$^{10}$ is H;

and the compound of formula (I) does not include the following structure:

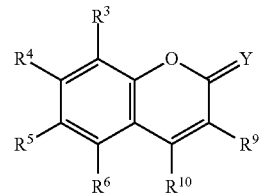

wherein R$^4$ is —O(C$_{1-6}$ alkyl); R$^5$ is halogen; R$^{10}$ is CF$_3$;

and the compound of formula (I) does not include the following structure:

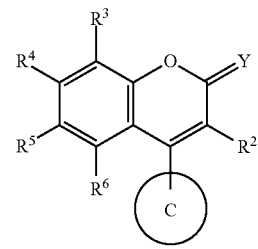

wherein R$^4$ is selected from —O(C$_{1-6}$ alkyl) and —O(C$_{1-4}$ alkylene-C$_{6-10}$ aryl);

ring C is C$_{6-10}$ aryl, which is optionally substituted with one or more substituents each independently selected from R$^{X1}$;

and the compound of formula (I) does not include the following structure:

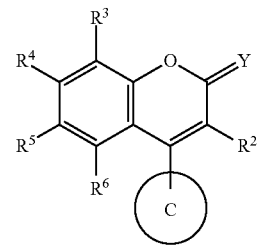

wherein R$^4$ is selected from —OH and —O(C$_{1-6}$ alkyl); R$^5$ is halogen; ring C is 5- to 10-membered heteroaryl, which is optionally substituted with one or more substituents each independently selected from R$^{X1}$.

In one embodiment, R$^1$ is =O. In another embodiment, R$^1$ is =S. In another embodiment, R$^1$ is OR$^7$.

In one embodiment, ring B is a saturated or unsaturated 5-membered or 6-membered heterocycle, wherein the heterocycle contains 1, 2 or 3 heteroatoms each independently selected from N, O and S. In one embodiment, ring B is a saturated or unsaturated 5-membered heterocycle, wherein the heterocycle contains 1 or 2 heteroatoms each independently selected from N and O. In another embodiment, ring B is dihydropyrrole. In another embodiment, ring B is selected from 2,3-dihydro-1H-pyrrole and 3,4-dihydro-1H-pyrrole, preferably 2,3-dihydro-1H-pyrrole. In yet another embodiment, ring B is pyrrolidine.

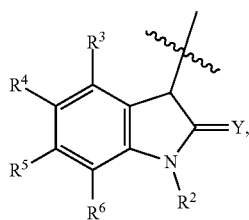

In a more preferred embodiment, the A-B ring system is wherein Y is O or S; and ring C is a 5- to 7-membered heteroaryl, preferably a 5- to 6-membered heteroaryl, especially a 5-membered heteroaryl, wherein the heteroaryl is optionally substituted with 1, 2, 3, 4 or 5 substituents each independently selected from $R^{X1}$. In a particular embodiment, the A-B ring system is

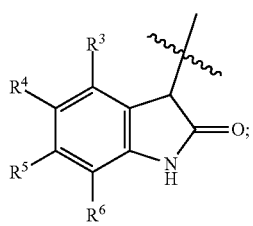

and ring C is a 5- to 7-membered heteroaryl, preferably a 5- to 6-membered heteroaryl, especially a 5-membered heteroaryl, the heteroaryl is optionally substituted by 1, 2, 3, 4 or 5 substituents each independently selected from $R^{X1}$. In another embodiment, ring C contains 1, 2, 3 or 4 heteroatoms, each of which is independently selected from N, O and S, preferably selected from N and O. In yet another embodiment, ring C contains at least one N atom. In one embodiment, ring C is a 5-membered heteroaryl group containing 1 or 2 N atoms, optionally substituted with 1, 2, 3, 4, or 5 substituents each independently selected from $R^{X1}$. In another embodiment, ring C is selected from pyrrole and imidazole.

In one embodiment, ring B is a saturated or unsaturated 6-membered heterocycle wherein the heterocycle contains 1 or 2 heteroatoms each independently selected from N and O. In another embodiment, ring B is dihydropyrimidine. In a preferred embodiment, ring B is selected from 1,6-dihydropyrimidine, 1,2-dihydropyrimidine and 1,4-dihydropyrimidine.

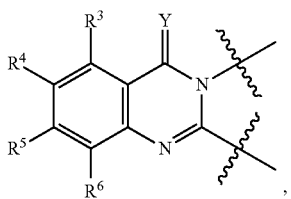

In a more preferred embodiment, the A-B ring system is wherein Y is O or S. In a particular embodiment, the A-B ring system is

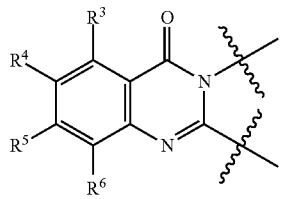

In yet another embodiment, ring B is 2H-pyran or 4H-pyran. In a preferred embodiment, the A-B ring system is

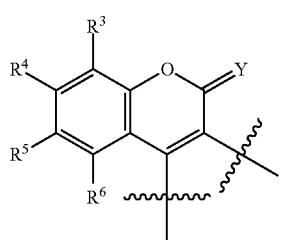

wherein Y is O or S. In a particular embodiment, the A-B ring system is

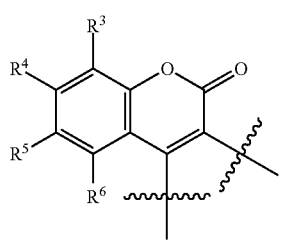

In yet another embodiment, ring C is phenyl, optionally substituted with 1, 2, 3, 4, or 5 substituents each independently selected from $R^{X1}$.

In one embodiment, $L^1$ is a bond. In another embodiment, $L^1$ is a $C_1$-$C_6$ hydrocarbon chain.

In a preferred embodiment, $L^1$ is a $C_1$-$C_2$ hydrocarbon chain.

In one embodiment, the A-B ring system is

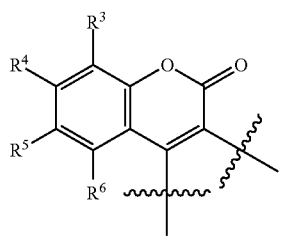

ring C is absent, and $L^1$ is absent.
In another embodiment:
ring A is a benzene ring;
ring B is a saturated or unsaturated 5-membered or 6-membered heterocycle, wherein heterocycle contains 1, 2 or 3 heteroatoms each independently selected from N, O and S;

ring C is selected from $C_{6-10}$ aryl and 5- to 10-membered heteroaryl, wherein aryl or heteroaryl is optionally substituted with one or more substituents each independently selected from $R^{X1}$;

$L^1$ is a bond, or a $C_{1-6}$ hydrocarbon chain;

$R^1$ is =Y, wherein Y is O or S, or $OR^7$;

at each occurrence, $R^2$ is each independently selected from hydrogen, halogen, —$NO_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl-$C_{1-4}$ alkyl, 5- to 10-membered heteroaryl-$C_{1-4}$ alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents independently selected from halogen, —$NO_2$, —CN, $C_{1-8}$ alkyl, $C_{2-8}$ alkenyl, $C_{2-8}$ alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;

$R^3$, $R^4$, $R^5$, $R^6$ are each independently selected from H and $R^{X2}$;

at each occurrence, $R^{X1}$ and $R^{X2}$ are each independently selected from halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl, alkenyl or alkynyl are optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), alkylene-3- to 7-membered heterocyclyl)$_2$, =O, —COOH and $C_{1-6}$ alkyl;

at each occurrence, $R^7$, $R^8$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl and $C_{6-10}$ aryl-$C_{1-4}$ alkyl, wherein the alkyl, alkenyl, alkynyl, cyclohydrocarbyl, heterocyclyl or aryl are optionally substituted with one or more substituents selected from halogen, —$NO_2$, —CN, $C_{1-6}$ alkyl, —OH, —O($C_{1-6}$ alkyl), —$NH_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl);

at each occurrence, $R^{a1}$, $R^{b1}$, $R^{a2}$, $R^{b2}$, $R^{c2}$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$ and —S(=O)$R^{Y1}$, wherein the alkyl, alkenyl, alkynyl, cyclohydrocarbyl, heterocyclyl, aryl or heteroaryl are optionally substituted with one or more substituents selected from halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

at each occurrence, $R^{Y1}$, $R^{Y2}$, $R^{Y3}$, $R^{Y4}$ are each independently selected from H, $C_{1-8}$ alkyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, —OH, —SH, —$NH_2$, =O and —COOH;

n is 1;

and provided that the compound of formula (I) does not include the following structure:

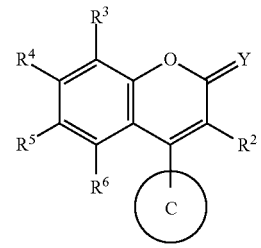

wherein $R^4$ is selected from —O($C_{1-6}$ alkyl) and —O($C_{1-4}$ alkylene-$C_{6-10}$ aryl);

ring C is $C_{6-10}$ aryl, which is optionally substituted with one or more substituents each independently selected from $R^{X1}$;

and the compound of formula (I) does not include the following structure:

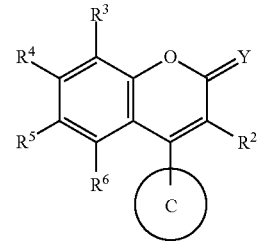

wherein $R^4$ is selected from —OH and —O($C_{1-6}$ alkyl); $R^5$ is halogen; ring C is 5- to 10-membered heteroaryl, which is optionally substituted with one or more substituents each independently selected from $R^{X1}$.

The structure described in the following formula (II) falls within the scope of the structure described in formula (I). In another aspect of the present invention, provided is use of a compound of formula (II), or a pharmaceutically acceptable salt, stereoisomer, solvate, polymorph, tautomer, isotopic compound, metabolite or prodrug thereof, in the preparation of a medicament for preventing or treating a polyQ-related neurodegenerative disorder

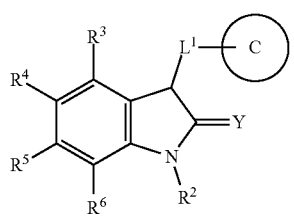

(II)

wherein:

Y is O or S;

ring C is 5- to 7-membered heteroaryl, the heteroaryl is optionally substituted with one or more substituents each independently selected from $R^{X1}$;

$R^2$ is selected from H and $C_{1-8}$ alkyl;

$L^1$ is a bond, or a $C_1$-$C_6$ hydrocarbon chain;

$R^3$, $R^4$, $R^5$, $R^6$ are each independently selected from H and $R^{X2}$;

wherein $R^{X1}$, $R^{X2}$ are as defined in formula (I).

In one embodiment, Y is O. When Y is O, the formula (II) is

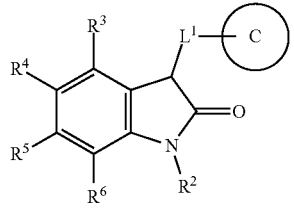

In one embodiment, ring C is a 5- to 6-membered heteroaryl, wherein the heteroaryl is optionally substituted with 1, 2, 3, 4 or 5 substituents each independently selected from $R^{X1}$. In a preferred embodiment, ring C is a 5-membered heteroaryl, which is optionally substituted with 1, 2, 3, 4 or 5 substituents each independently selected from $R^{X1}$. In another embodiment, ring C contains 1, 2, 3 or 4 heteroatoms, each of which is independently selected from N, O and S, preferably selected from N and O. In another embodiment, ring C contains at least one N atom. In one embodiment, ring C is a 5-membered heteroaryl containing 1 or 2 N atoms, optionally substituted with 1, 2, 3, 4, or 5 substituents each independently selected from $R^{X1}$. In another embodiment, ring C is selected from pyrrole and imidazole.

In one embodiment, $L^1$ is a bond. In another embodiment, $L^1$ is a $C_1$-$C_6$ hydrocarbon chain. In a preferred embodiment, $L^1$ is a $C_1$-$C_2$ hydrocarbon chain. In one embodiment, $L^1$ is methylene or methenyl. In a special embodiment, $L^1$ is methenyl. In another particular embodiment, $L^1$ is

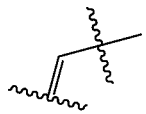

In another particular embodiment, the compound of formula (II) is selected from:

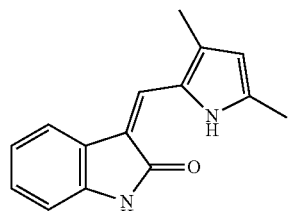

(compound 3)

and

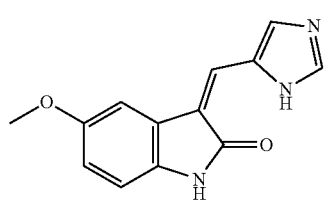

(compound 4)

The structure described in the following formula (III) falls within the scope of the structure described in formula (I). In another aspect of the present invention, provided is use of a compound of formula (III), or a pharmaceutically acceptable salt, stereoisomer, solvate, polymorph, tautomer, isotopic compound, metabolite or prodrug thereof, in the preparation of a medicament for preventing or treating a polyQ-related neurodegenerative disorder wherein:

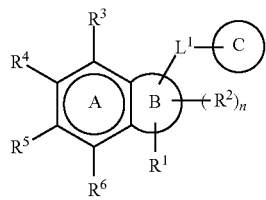

(III)

ring B is a saturated or unsaturated 6-membered heterocycle, wherein the heterocycle contains 1, 2, or 3 heteroatoms each independently selected from N, O and S;

Ring C is a $C_{6-10}$ aryl, optionally substituted with one or more substituents each independently selected from $R^{X1}$;

or ring C is absent, and $L^1$ is absent;

ring A, $L^1$, $R^1$, $R^2$, $R^3$, $R^4$, $R^5$, $R^6$, $R^{X1}$, n are as defined in formula (I);

provided that the compound of formula (III) does not include the following structure:

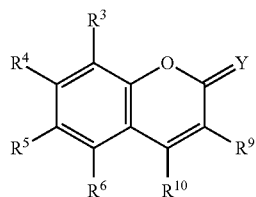

wherein $R^3$ is selected from —O($C_{1-6}$ alkyl) and —O($C_{1-4}$ alkylene-$C_{6-10}$ aryl); $R^{10}$ is H;
and the compound of formula (III) does not include the following structure:

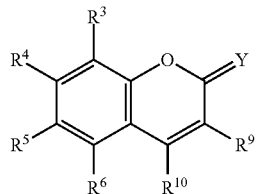

wherein $R^4$ is —O($C_{1-6}$ alkyl); $R^5$ is halogen; $R^{10}$ is $CF_3$;
and the compound of formula (III) does not include the following structure:

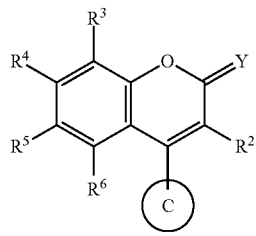

wherein $R^4$ is selected from —O($C_{1-6}$ alkyl) and —O($C_{1-4}$ alkylene-$C_{6-10}$ aryl);
ring C is a $C_{6-10}$ aryl, which is optionally substituted with one or more substituents each independently selected from $R^{X1}$;
and the compound of formula (III) does not include the following structure:

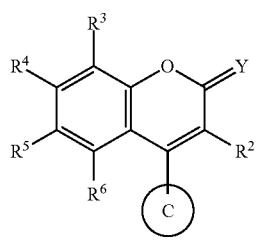

wherein $R^4$ is selected from —OH and —O($C_{1-6}$ alkyl); $R^5$ is halogen; ring C is a 5- to 10-membered heteroaryl, wherein heteroaryl is substituted with one or more substituents each independently selected from $R^{X1}$.

In one embodiment, ring B is a saturated or unsaturated 6-membered heterocycle, wherein heterocycle contains 1, 2 or 3 heteroatoms each independently selected from N, O and S. In one embodiment, ring B is a saturated or unsaturated 6-membered heterocycle, wherein heterocycle contains 1 or 2 heteroatoms each independently selected from N and O. In another embodiment, ring B is dihydropyrimidine. In a preferred embodiment, ring B is selected from 1,6-dihydropyrimidine, 1,2-dihydropyrimidine and 1,4-dihydropyrimidine.

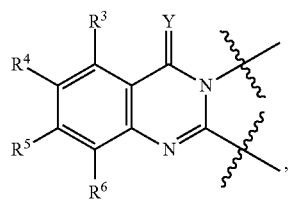

In a more preferred embodiment, the A-B ring system is wherein Y is O or S. In a particular embodiment, the A-B ring system is

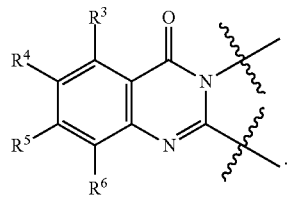

In yet another embodiment, ring B is 2H-pyran or 4H-pyran. In a preferred embodiment, the A-B ring system is

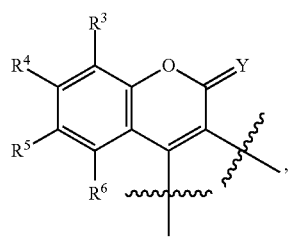

wherein Y is O or S. In a particular embodiment, the A-B ring system is

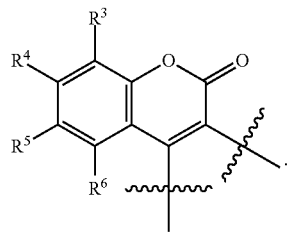

In yet another embodiment, ring C is phenyl, optionally substituted with 1, 2, 3, 4, or 5 substituents each independently selected from $R^{X1}$.

In one embodiment, $L^1$ is a bond. In another embodiment, $L^1$ is a $C_1$-$C_6$ hydrocarbon chain.

In a preferred embodiment, $L^1$ is a $C_1$-$C_2$ hydrocarbon chain.

In one embodiment, the A-B ring system is

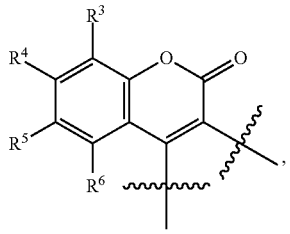

ring C is absent, and $L^1$ is absent.

In an alternative embodiment, ring B and ring C of the compound of formula (III) are further connected through $L^2$ to obtain a variant of the compound of formula (III), which has the following structure of formula (III')

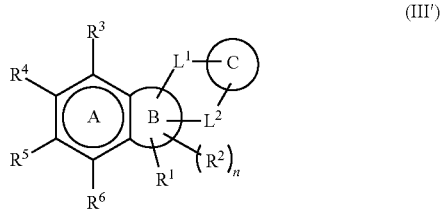

(III')

wherein:
ring C is $C_{6-10}$ aryl, which is optionally substituted with one or more substituents each independently selected from $R^{X1}$;
$R^1$ is H, =O, or is $OR^7$;
$L^1$ is a bond, or is a $C_1$-$C_2$ hydrocarbon chain;
$L^2$ is a bond, or is a $C_1$-$C_2$ hydrocarbon chain;
provided that $L^1$ and $L^2$ are not bonds at the same time;
$R^3, R^4, R^5, R^6$ are each independently selected from H and $R^{X2}$;
ring A, ring B, $R^2$, n, $R^{X1}$ are as defined in formula (III).

In one embodiment, $R^1$ is H.

In another embodiment, $R^2$ is —OH.

In one embodiment, at each occurrence, $R^{X2}$ is each independently selected from halogen, —$NO_2$, —CN, $C_{1-6}$ alkyl, —OH and —O($C_{1-6}$ alkyl).

The structure described in the following formula (IV) falls within the scope of the structure described in formula (I) and formula (III). In another aspect of the present invention, provided is use of a compound of formula (IV), or a pharmaceutically acceptable salt, stereoisomer, solvate, polymorph, tautomer, isotopic compound, metabolite or prodrug thereof, in the preparation of a medicament for preventing or treating a polyQ-related neurodegenerative disorder

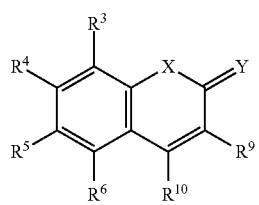

(IV)

wherein:

Y is O or S;

X is O;

$R^9$ is selected from H, halogen, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$ and —S(=O)$R^{a1}$, wherein the alkyl, cyclohydrocarbyl or heterocyclyl are optionally substituted with one or more substituents selected from halogen, —$NO_2$, —CN, $C_{1-6}$ alkyl, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$; wherein $R^{a1}, R^{b1}, R^{a2}, R^{b2}$ are as defined in formula (III);

$R^{10}$ is selected from H, halogen, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, and 3- to 7-membered heterocyclyl-$C_{1-4}$ alkyl;

$R^3$ is selected from H, halogen, $C_{1-6}$ alkyl, —OH, —$NH_2$, —NH($C_{1-6}$ alkyl) and —N($C_{1-6}$ alkyl)$_2$, wherein the alkyl is optionally substituted with one or more substituents selected from halogen, —OH, —O($C_{1-6}$ alkyl), —$NH_2$, —NH($C_{1-6}$ alkyl) and —N($C_{1-6}$ alkyl)$_2$;

$R^4$ is selected from H, halogen, —$NO_2$, —CN, $C_{1-6}$ alkyl, —$OR^7$, —$SR^7$ and —$NR^7R^8$; at each occurrence, $R^7$, $R^8$ are each independently selected from H and $C_{1-6}$ alkyl, wherein the alkyl is optionally substituted with one or more substituents selected from halogen, —$NO_2$, —CN, —OH, —O($C_{1-6}$ alkyl), —$NH_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl); wherein $R^7, R^8$ are as defined in formula (III);

$R^5$ is selected from H, halogen, —$NO_2$, —CN, $C_{1-6}$ alkyl, —OH, —O($C_{1-6}$ alkyl), —$NH_2$, —NH($C_{1-6}$ alkyl), —N($C_{1-6}$ alkyl)$_2$, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl), wherein the alkyl is optionally substituted with one or more substituents selected from halogen, —OH, —O($C_{1-6}$ alkyl), —$NH_2$, —NH($C_{1-6}$ alkyl), —N($C_{1-6}$ alkyl)$_2$, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl);

$R^6$ is selected from H, halogen, —$NO_2$, —CN, $C_{1-6}$ alkyl, —OH, —O($C_{1-6}$ alkyl), —O(benzyl), —SH, —S($C_{1-6}$ alkyl), —S(benzyl), —$NH_2$, —NH($C_{1-6}$ alkyl), —N($C_{1-6}$ alkyl)$_2$ and —NH(benzyl), wherein the alkyl or benzyl is optionally substituted with one or more substituents selected from halogen, —OH, —O($C_{1-6}$ alkyl), —$NH_2$, —NH($C_{1-6}$ alkyl) and —N($C_{1-6}$ alkyl)$_2$;

provided that when $R^4$ is —O($C_{1-6}$ alkyl) and $R^5$ is halogen, $R^{10}$ is not $CF_3$.

In one embodiment, Y is O. When Y is O, formula (IV) is

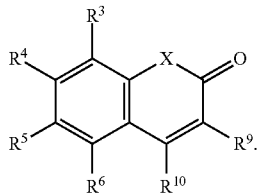

In one embodiment, $R^9$ is selected from H, halogen, $C_{1-6}$ alkyl, —$OR^{a1}$, —$NR^{a1}R^{b1}$, —$C(=O)OR^{a1}$, $C(=O)NR^{a1}R^{b1}$ and —$S(=O)_2NR^{a1}R^{b1}$, wherein the alkyl is optionally substituted with one or more substituents selected from halogen, —$NO_2$, —CN, $C_{1-6}$ alkyl, —$OR^{a2}$, —$SR^{a2}$, —$NR^{a2}R^{b2}$, —$C(=O)OR^{a2}$, —$C(=O)NR^{a2}R^{b2}$ and —$C(=O)R^{a2}$. In one embodiment, $R^9$ is selected from H, halogen, —$OR^{a1}$, —$NR^{a1}R^{b1}$, —$C(=O)OR^{a1}$ and —$C(=O)NR^{a1}R^{b1}$. In one embodiment, $R^9$ is —$OR^{a1}$ or —$NR^{a1}R^{b1}$. In another embodiment, $R^9$ is —$C(=O)OR^{a2}$ or —$C(=O)NR^{a2}R^{b2}$. In a particular embodiment, $R^9$ is —NHC(=O)($C_{1-6}$ alkyl). In a particular embodiment, $R^9$ is —$NHC(=O)CH_3$.

In one embodiment, $R^{10}$ is selected from H, halogen and methyl. In another embodiment, $R^{10}$ is H.

In one embodiment, at each occurrence, $R^{a1}$, $R^{b1}$ are each independently selected from H, $C_{1-6}$ alkyl and —C(=O)$R^{Y1}$, wherein the alkyl is optionally substituted with one or more substituents selected from halogen, —$OR^{Y3}$, —$SR^{Y3}$, —$NR^{Y3}R^{Y4}$, —$C(=O)R^{Y3}$, —$C(=O)OR^{Y3}$ and —$C(=O)NR^{Y3}R^{Y4}$. Wherein $R^{Y1}$, $R^{Y3}$, $R^{Y4}$ are as defined in formula (III). In one embodiment, at each occurrence, $R^{a1}R^{b1}$ are independently selected from H, $C_{1-6}$ alkyl and —C(=O)($C_{1-6}$ alkyl), wherein the alkyl is optionally substituted with one or more substituents selected from halogen, —OH, —O($C_{1-6}$ alkyl), —O($C_{3-6}$ cyclohydrocarbyl), —$NH_2$, —NH($C_{1-6}$alkyl), —N($C_{1-6}$ alkyl)$_2$, —NH($C_{3-6}$ cyclohydrocarbyl), —N($C_{3-6}$ cyclohydrocarbyl)$_2$, —C(=O)($C_{1-6}$ alkyl), —C(=O)O($C_{1-6}$ alkyl), —C(=O)O($C_{3-6}$ cyclohydrocarbyl), —C(=O)NH($C_{1-6}$ alkyl) and —C(=O)N($C_{1-6}$ alkyl)$_2$. In one embodiment, at each occurrence, $R^{a1}$, $R^{b1}$ are independently selected from H and $C_{1-6}$ alkyl.

In one embodiment, at each occurrence, $R^{a2}$, $R^{b2}$ are each independently selected from H and $C_{1-6}$ alkyl.

In one embodiment, $R^3$ is selected from H, —OH and $C_{1-6}$ alkyl, wherein the alkyl is optionally substituted with one or more substituents selected from halogen, —$NO_2$, —CN, —OH, —SH, —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$ and —COOH. In one embodiment, $R^3$ is selected from H, halogen, methyl, —OH, —$NH_2$ and —$NHCH_3$, wherein the methyl is optionally substituted with substituents selected from halogen, —OH, —$NH_2$ and —NH($C_{1-2}$ alkyl). In one embodiment, $R^3$ is selected from H, halogen, methyl, —OH, —$NH_2$ and —$NHCH_3$, wherein the methyl is optionally substituted with substituents selected from halogen, —OH, —$OCH_3$, —$NH_2$ and —$NHCH_3$. In one embodiment, $R^3$ is selected from H, halogen, methyl, —OH and —$NH_2$. In one embodiment, $R^3$ is selected from H, F, Cl, methyl, —OH and —$NH_2$. In another embodiment, $R^3$ is selected from H, F, methyl, —OH and —$NH_2$. In a particular embodiment, $R^3$ is selected from H, methyl and —OH. In another particular embodiment, $R^3$ is H. In another particular embodiment, $R^3$ is —OH. In another embodiment, $R^3$ is dimethylaminomethyl.

In one embodiment, $R^4$ is selected from H, —$OR^7$, —$SR^7$ and —$NR^7R^8$; at each occurrence, $R^7$, $R^8$ are each independently selected from H and $C_{1-6}$ alkyl, wherein the alkyl is optionally substituted with one or more substituents selected from halogen, $C_{1-6}$ alkyl, —OH, —O($C_{1-6}$ alkyl), —$NH_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl) and —C(=O)N($C_{1-6}$ alkyl)$_2$. In one embodiment, $R^4$ is $C_{1-6}$ alkyl, wherein the alkyl is optionally substituted with one or more substituents selected from halogen, —COOH, —C(=O)O($C_{1-6}$ alkyl), —C(=O)NH($C_{1-6}$ alkyl) and —C(=O)N($C_{1-6}$ alkyl)$_2$. In a particular embodiment, $R^4$ is —$CH_2COOH$. In another embodiment, $R^4$ is selected from H, halogen, —$NO_2$, —CN, $C_{1-6}$ alkyl, —OH, —O($C_{1-6}$ alkyl), —$NH_2$, —NH($C_{1-6}$ alkyl) and —N($C_{1-6}$ alkyl)$_2$, wherein the alkyl is optionally substituted with one or more substituents selected from halogen, —OH, —O($C_{1-6}$ alkyl), —$NH_2$, —NH($C_{1-6}$ alkyl) and —N($C_{1-6}$ alkyl)$_2$. In one embodiment, $R^4$ is selected from H, halogen, $C_{1-3}$ alkyl, —OH, —O($C_{1-3}$ alkyl), —$NH_2$, —NH($C_{1-3}$ alkyl), —N($C_{1-3}$ alkyl)$_2$ and —COOH, wherein the alkyl is optionally substituted with one or more substituents selected from halogen, —OH, —O($C_{1-2}$ alkyl), —$NH_2$, —NH($C_{1-2}$ alkyl), —N($C_{1-2}$ alkyl)$_2$ and —COOH.

In one embodiment, $R^5$ is selected from H and $C_{1-6}$ alkyl, wherein the alkyl is optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$ and —COOH. In another embodiment, $R^5$ is selected from H, halogen, $C_{1-3}$ alkyl, —OH, —O($C_{1-3}$ alkyl), —$NH_2$, —NH($C_{1-3}$ alkyl), —N($C_{1-3}$ alkyl)$_2$ and —COOH, wherein the alkyl is optionally substituted with one or more substituents selected from halogen, —OH, —O($C_{1-2}$ alkyl), —$NH_2$, —NH($C_{1-2}$ alkyl), —N($C_{1-2}$ alkyl)$_2$ and —COOH. In one embodiment, $R^5$ is selected from H, halogen, $C_{1-3}$ alkyl, —OH, —O($C_{1-3}$ alkyl), —$NH_2$, —NH($C_{1-3}$ alkyl) and —N($C_{1-3}$ alkyl)$_2$, wherein the alkyl is optionally substituted with one or more substituents selected from halogen, —OH, —O($C_{1-2}$ alkyl), —$NH_2$, —NH($C_{1-2}$ alkyl), —N($C_{1-2}$ alkyl)$_2$. In one embodiment, $R^5$ is dimethylaminomethyl.

In one embodiment, $R^6$ is selected from H, halogen, $C_{1-6}$ alkyl, —OH and —$NH_2$, wherein the alkyl is optionally substituted with one or more substituents selected from halogen, —OH and —$NH_2$. In one embodiment, $R^6$ is selected from H, F, Cl, Br, $C_{1-6}$ alkyl, —OH and —$NH_2$, wherein the alkyl is optionally substituted with one or more substituents selected from halogen, —OH and —$NH_2$. In one embodiment, $R^6$ is selected from H, F, Cl, Br, methyl, —OH and —$NH_2$. In one embodiment, $R^6$ is H or —OH.

In one embodiment, R³ is methyl, and R⁴ is selected from —OH, —NH₂, —NH(C₁₋₃ alkyl), —N(C₁₋₃ alkyl)₂, and, C₁₋₃ alkyl substituted with —COOH, wherein the substituted C₁₋₃ alkyl is substituted with one or more substituents selected from —OH, —NH₂, —NH(C₁₋₂ alkyl), —N(C₁₋₂ alkyl)₂ and —COOH. In one embodiment, R³ is methyl, and R⁴ is selected from —NH₂, —NH(C₁₋₃ alkyl), —N(C₁₋₃ alkyl)₂, and, C₁₋₃ alkyl substituted with —COOH, wherein substituted C₁₋₃ alkyl is substituted with one or more substituents selected from —OH, —NH₂, —NH(C₁₋₂ alkyl), —N(C₁₋₂ alkyl)₂ and —COOH.

In another embodiment, R³ is methyl, and R⁵ is selected from —OH, —NH₂, —NH(C₁₋₃ alkyl), —N(C₁₋₃ alkyl)₂, and, C₁₋₃ alkyl substituted with —COOH, wherein the substituted C₁₋₃ alkyl is substituted with one or more substituents selected from —OH, —NH₂, —NH(C₁₋₂ alkyl), —N(C₁₋₂ alkyl)₂ and —COOH. In another embodiment, R³ is methyl, and R⁵ is selected from —NH₂, —NH(C₁₋₃ alkyl), —N(C₁₋₃ alkyl)₂, and, C₁₋₃ alkyl substituted with —COOH, wherein the substituted C₁₋₃ alkyl is substituted with one or more substituents selected from —OH, —NH₂, —NH(C₁₋₂ alkyl), —N(C₁₋₂ alkyl)₂ and —COOH.

The structure described in the following formula (V) falls within the scope of the structure described in formula (I), formula (III) and formula (IV). In another aspect of the present invention, provided is use of a compound of formula (V), or a pharmaceutically acceptable salt, stereoisomer, solvate, polymorph, tautomer, isotopic compound, metabolite or prodrug thereof, in the preparation of a medicament for preventing or treating a polyQ-related neurodegenerative disorder,

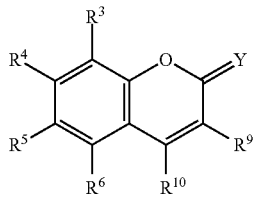

(V)

wherein:

Y, R⁹, R¹⁰, R³, R⁴, R⁵, R⁶ are as defined in formula (IV); in one embodiment, Y is O. When Y is O, formula (V) is

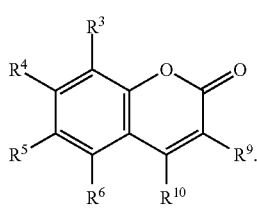

In a particular embodiment, compound of formula (V) is

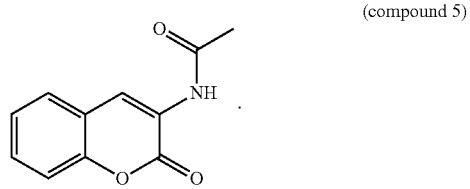

(compound 5)

The structure described in the following formula (VI) falls within the scope of the structure described in formula (I) and formula (III). In another aspect of the present invention, there is provided use of a compound of formula (VI), or a pharmaceutically acceptable salt, stereoisomer, solvate, polymorph, tautomer, isotopic compound, metabolite or prodrug thereof, in the preparation of a medicament for preventing or treating a polyQ-related neurodegenerative disorder

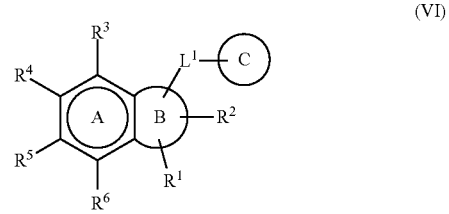

(VI)

wherein:

ring B is a saturated or unsaturated 6-membered heterocycle, wherein the heterocycle contains 1, 2 or 3 heteroatoms each independently selected from N, O and S ring C is a C₆₋₁₀ aryl, wherein the aryl optionally substituted with one or more substituents each independently selected from $R^{X1}$;

L¹ is a bond, or a C₁-C₆ hydrocarbon chain; R² is selected from H, halogen, —NO₂, —CN, C₁₋₈ alkyl, C₂₋₈ alkenyl, C₂₋₈ alkynyl, C₃₋₁₀ cyclohydrocarbyl, C₃₋₁₀ cyclohydrocarbyl-C₁₋₄ alkyl, 3- to 10-membered heterocyclyl, 3- to 10-membered heterocyclyl-C₁₋₄ alkyl, C₆₋₁₀ aryl-C₁₋₄ alkyl, 5- to 10-membered heteroaryl-C₁₋₄ alkyl, =O, =S, =NR$^{a1}$, —OR$^{a1}$, —SR$^{a1}$, —NR$^{a1}$R$^{b1}$, —C(=O)OR$^{a1}$, —C(=O)NR$^{a1}$R$^{b1}$, —C(=O)R$^{a1}$, —S(=O)₂OR$^{a1}$, —S(=O)₂R$^{a1}$, —S(=O)₂NR$^{a1}$R$^{b1}$, —S(=O)R$^{a1}$, —C(=S)OR$^{a1}$, —C(=S)NR$^{a1}$R$^{b1}$, —C(=S)R$^{a1}$, —P(=O)(OR$^{a1}$)OR$^{b1}$, —C(=NR$^{a1}$)NR$^{b1}$R$^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —NO₂, —CN, C₁₋₈ alkyl, C₂₋₈ alkenyl, C₂₋₈ alkynyl, =O, =S, —OR$^{a2}$, —SR$^{a2}$, —NR$^{a2}$R$^{b2}$, —C(=O)OR$^{a2}$, —C(=O)NR$^{a2}$R$^{b2}$, —C(=O)R$^{a2}$, —S(=O)₂OR$^{a2}$, —S(=O)₂R$^{a2}$, —S(=O)₂NR$^{a2}$R$^{b2}$, —S(=O)R$^{a2}$ and —C(=NR$^{a2}$)NR$^{b2}$R$^{c2}$;

R³, R⁴, R⁵, R⁶ are each independently selected from H and $R^{X2}$;

at each occurrence, $R^{X1}$ and R are each independently selected from halogen, —NO₂, —CN, C₁₋₆ alkyl, C₂₋₆ alkenyl, C₂₋₆ alkynyl, —OR⁷, —SR⁷, —NR⁷R⁸, —C(=O)OR⁷, —C(=O)NR⁷R⁸, —OC(=O)R⁷, —NC(=O)R⁷R⁸, —C(=O)R⁷, —S(=O)₂OR⁷, —S(=O)₂R⁷, —S(=O)₂NR⁷R⁸, —OS(=O)₂R⁷, —NS(=O)₂R⁷R⁸ and —S(=O)R⁷, wherein the alkyl, alkenyl or alkynyl are optionally substituted with one or more substituents selected from halogen, —NO₂, —CN, —OH, —O(C₁₋₆ alkyl), —O(C₃₋₆ cyclohydrocarbyl), —O(C₁₋₄ alkylene-C₃₋₆ cyclohydrocarbyl), —O(3- to 7-membered heterocyclyl), —O(C₁₋₄ alkylene)-(3- to 7-membered heterocyclyl), —SH, —S(C₁₋₆ alkyl), —S(C₃₋₆ cyclohydrocarbyl), —S(C₁₋₄ alkylene-C₃₋₆ cyclohydrocarbyl), —S(3- to 7-membered heterocyclyl), —S(C₁₋₄ alkylene)-(3- to 7-membered heterocyclyl), —NH₂, —NH(C₁₋₆ alkyl), —N(C₁₋₆ alkyl)₂, —NH(C₃₋₆ cyclohydrocarbyl), —N(C₃₋₆ cyclohydrocarbyl)₂, —NH(C₁₋₄ alkylene-C₃₋₆ cyclohydrocarbyl), —N(C₁₋₄ alkylene-C₃₋₆ cyclohydrocarbyl)₂, —NH(3- to 7-membered heterocyclyl), —N(3- to 7-membered heterocyclyl)₂, —NH(C₁₋₄ alkylene-3- to 7-membered heterocyclyl), —N(C₁₋₄ alkylene-3- to 7-membered heterocyclyl)₂, =O, —COOH and C₁₋₆ alkyl;

at each occurrence, R⁷, R⁸ are each independently selected from H, C₁₋₆ alkyl, C₂₋₆ alkenyl, C₂₋₆ alkynyl, C₃₋₆ cyclohydrocarbyl, C₃₋₆ cyclohydrocarbyl-C₁₋₄ alkyl, 3- to 7-membered heterocyclyl, and 3- to 7-membered heterocyclyl-C₁₋₄ alkyl, wherein the alkyl, alkenyl, alkynyl, cyclohydrocarbyl or heterocyclyl are optionally substituted with one or more substituents selected from halogen, —NO₂, —CN, C₁₋₆ alkyl, —OH, —O(C₁₋₆ alkyl), —NH₂, —NH(C₁₋₆ alkyl), —N(C₁₋₆ alkyl)₂, —COOH, —C(=O)O(C₁₋₆ alkyl), —C(=O)NH(C₁₋₆ alkyl), —C(=O)N(C₁₋₆ alkyl)₂, —OC(=O)(C₁₋₆ alkyl), —NHC(=O)(C₁₋₆ alkyl) and —C(=O)(C₁₋₆ alkyl);

at each occurrence, $R^{a1}$, $R^{b1}$, $R^{c1}$, $R^{a2}$, $R^{b2}$, $R^{c2}$ are each independently selected from H, C₁₋₆-alkyl, C₂₋₆ alkenyl, C₂₋₆ alkynyl, C₃₋₆ cyclohydrocarbyl, C₃₋₆ cyclohydrocarbyl-C₁₋₄ alkyl, 3- to 7-membered heterocyclyl, 3- to 7-membered heterocyclyl-C₁₋₄ alkyl, C₆₋₁₀ aryl, C₆₋₁₀ aryl-C₁₋₄ alkyl, 5- to 10-membered heteroaryl, 5- to 10-membered heteroaryl-C₁₋₄ alkyl, —OR$^{y1}$, —SR$^{y1}$, —NR$^{y1}$R$^{y2}$, —C(=O)OR$^{y1}$, —C(=O)NR$^{y1}$R$^{y2}$, —C(=O)R$^{y1}$, —S(=O)₂OR$^{y1}$, —S(=O)₂R$^{y1}$, —S(=O)₂NR$^{y1}$R$^{y2}$ and —S(=O)R$^{y1}$, wherein the alkyl, alkenyl, alkynyl, cyclohydrocarbyl, heterocyclyl, aryl or heteroaryl are optionally substituted with one or more substituents selected from halogen, =O, =S, —OR$^{y3}$, —SR$^{y3}$, —NR$^{y3}$R$^{y4}$, —C(=O)R$^{y3}$, —C(=O)OR$^{y3}$ and —C(=O)NR$^{y3}$R$^{y4}$;

at each occurrence, $R^{y1}$, $R^{y2}$, $R^{y3}$, $R^{y4}$ are each independently selected from H, C₁₋₈ alkyl, C₃₋₁₀ cyclohydrocarbyl, C₃₋₁₀ cyclohydrocarbyl-C₁₋₄ alkyl, 3- to 10-membered heterocyclyl, 3- to 10-membered heterocyclyl-C₁₋₄ alkyl, C₆₋₁₀ aryl, C₆₋₁₀ aryl-C₁₋₄ alkyl, 5- to 10-membered heteroaryl, and 5- to 10-membered heteroaryl-C₁₋₄ alkyl, wherein the alkyl, alkenyl, alkynyl, cyclohydrocarbyl, heterocyclyl, aryl or heteroaryl are optionally substituted with one or more substituents selected from halogen, —NO₂, —CN, C₁₋₈ alkyl, C₂₋₈ alkenyl, C₂₋₈ alkynyl, —OH, —SH, —NH₂, =O and —COOH;

ring A and R¹ are as defined in formula (III);

provided that the compound of formula (VI) does not include the following structure:

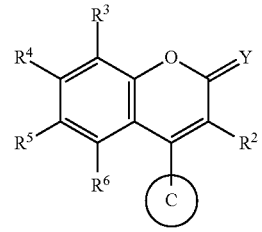

wherein R⁴ is selected from —O(C₁₋₆ alkyl) and —O(C₁₋₄ alkylene-C₆₋₁₀ aryl).

In one embodiment, ring B is a saturated or unsaturated 6-membered heterocycle, wherein heterocycle contains 1 or 2 heteroatoms each independently selected from N and O. In another embodiment, ring B is dihydropyrimidine. In a preferred embodiment, ring B is selected from 1,6-dihydropyrimidine, 1,2-dihydropyrimidine and 1,4-dihydropyrimidine.

In a more preferred embodiment, the A-B ring system is

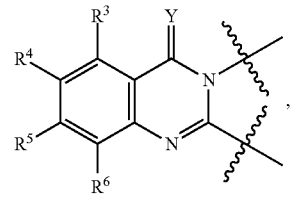

wherein Y is O or S. In a particular embodiment, the A-B ring system is

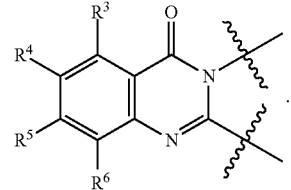

In yet another embodiment, ring B is 2H-pyran or 4H-pyran. In a preferred embodiment, A-B ring system is

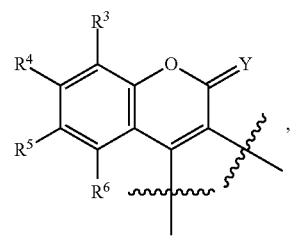

wherein Y is O or S. In a particular embodiment, A-B ring system is

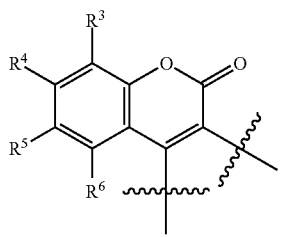

In yet another embodiment, ring C is phenyl, wherein phenyl is optionally substituted with 1, 2, 3, 4 or 5 substituents each independently selected from $R^{X1}$.

In one embodiment, $L^1$ is a bond. In another embodiment, $L^1$ is a $C_1$-$C_6$ hydrocarbon chain. In a preferred embodiment, $L^1$ is $C_1$-$C_2$ hydrocarbon chain.

In yet another embodiment, $R^2$ is selected from H, halogen, —$NO_2$, —CN, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, =O, =S, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$ and —S(=O)$R^{a1}$, wherein the alkyl, alkenyl, alkynyl, cyclohydrocarbyl or heterocyclyl are optionally substituted with one or more substituents selected from halogen, —$NO_2$, —CN, $C_{1-6}$ alkyl, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$. In another embodiment, $R^2$ is selected from H, halogen, —$NO_2$, —CN, =O, =S, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3- to 7-membered heterocyclyl), —O(C=O)($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl), —NH(C=O)(3- to 7-membered heterocyclyl), —C(=O)($C_{1-6}$ alkyl), —COOH, —C(=O)O($C_{1-6}$ alkyl), —C(=O)O($C_{3-6}$ cyclohydrocarbyl), —C(=O)O($C_{1-4}$ alkylene-$C_{3-6}$ cyclohydrocarbyl), —C(=O)O(3- to 7-membered heterocyclyl), —C(=O)O($C_{1-4}$ alkylene)-(3- to 7-membered heterocyclyl), —C(=O)$NH_2$, —C(=O)NH($C_{1-6}$ alkyl), —C(=O)N($C_{1-6}$ alkyl)$_2$, —C(=O)NH($C_{1-4}$ alkylene-$C_{3-6}$ cyclohydrocarbyl), —C(=O)N($C_{1-4}$ alkylene-$C_{3-6}$ cyclohydrocarbyl)$_2$, —C(=O)NH(3- to 7-membered heterocyclyl), —C(=O)N(3- to 7-membered heterocyclyl)$_2$, —C(=O)NH($C_{1-4}$ alkylene-3- to 7-membered heterocyclyl), and —C(=O)N($C_{1-4}$ alkylene-3- to 7-membered heterocyclyl)$_2$, wherein the alkyl, alkylene, alkenyl, alkynyl, cyclohydrocarbyl or heterocyclyl or are optionally substituted with one or more substituents selected from halogen, nitro, cyano, —OH, —SH, —$NH_2$ and —COOH. In yet another embodiment, $R^2$ is selected from H, halogen, —$NO_2$, —CN, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, S(=O)$_2R^{a1}$, —S(=O)$_2NR^{a1}R^{b1}$ and —S(=O)$R^{a1}$, wherein the alkyl, cyclohydrocarbyl or heterocyclyl are optionally substituted with one or more substituents selected from halogen, —$NO_2$, —CN, $C_{1-6}$ alkyl, —$OR^{a2}$, —$SR^{a2}$, —$NR^{a2}R^{b2}$, —C(=O)$OR^{a2}$, —C(=O)$NR^{a2}R^{b2}$ and —C(=O)$R^{a2}$. In a preferred embodiment, $R^2$ is selected from H, halogen, —$NO_2$, —CN, $C_{1-6}$ alkyl and —OH, wherein the alkyl is optionally substituted with one or more substituents selected from halogen, —$NO_2$, —CN, $C_{1-6}$ alkyl and —$NR^{a2}R^{b2}$. In a more preferred embodiment, $R^2$ is selected from H, halogen, $C_{1-6}$ alkyl and —OH, wherein the alkyl is optionally substituted with one or more substituents selected from halogen, $C_{1-6}$ alkyl and —$NR^{a2}R^{b2}$. In a further embodiment, $R^2$ is selected from H, $C_{1-4}$ alkyl and —OH, wherein the alkyl is optionally substituted with one or more substituents selected from —$NR^{a2}R^{b2}$. In a particular embodiment, $R^2$ is selected from H, $C_{1-4}$ alkyl and —OH, wherein the alkyl is —$CH_2[CH(CH_3)_2]$ and is optionally substituted with one or more substituents selected from —$NR^{b2}$. In another embodiment, $R^2$ is an alkyl substituted with —$NR^{a1}R^{b1}$ In a particular embodiment, $R^2$ is

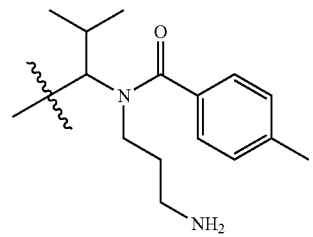

In one embodiment, at each occurrence, $R^{X1}$ and $R^{X2}$ are each independently selected from halogen, —$NO_2$, —CN, $C_{1-6}$ alkyl, —OW, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl is optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —SH, —S($C_{1-6}$ alkyl), —S($C_{3-6}$ cyclohydrocarbyl), —S ($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, =O and —COOH. In a preferred embodiment, at each occurrence, $R^{X1}$ and $R^{X2}$ are each independently selected from halogen, —NO$_2$, —CN, $C_{1-6}$ alkyl, —OR$^7$, —SR$^7$, —NR$^7$R$^8$, —OC(=O)R$^7$, —NC(=O)R$^7$R$^8$, —OS(=O)$_2$R$^7$ and —NS(=O)$_2$R$^7$R$^8$, wherein the alkyl is optionally substituted with one or more substituents selected from halogen, —NO$_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —NH$_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), and —N($C_{1-4}$ alkylene-3- to 7-membered heterocyclyl)$_2$. In a preferred embodiment, at each occurrence, $R^{X1}$ and $R^{X2}$ are each independently selected from halogen, $C_{1-6}$ alkyl, —OR$^7$ and —NR$^7$R$^8$, more preferably each independently selected from halogen and —OR$^7$, wherein the alkyl is optionally substituted with one or more substituents selected from halogen, —NO$_2$, —CN, —OH, —O($C_{1-6}$ alkyl), —NH$_2$, —NH($C_{1-6}$ alkyl) and —N($C_{1-6}$ alkyl)$_2$. In a more preferred embodiment, at each occurrence, $R^{X1}$ and $R^{X2}$ are each independently selected from F, Cl, Br, —OH, —O($C_{1-6}$ alkyl), —NH$_2$, —NH($C_{1-6}$ alkyl), —N($C_{1-6}$ alkyl)$_2$, and, optionally substituted $C_{1-6}$ alkyl, wherein the optionally substituted $C_{1-6}$ alkyl is optionally substituted with one or more substituents selected from halogen, —NO$_2$, —CN, —OH, —O($C_{1-6}$ alkyl), —NH$_2$, —NH($C_{1-6}$ alkyl) and —N($C_{1-6}$ alkyl)$_2$. In a particular embodiment, at each occurrence, $R^{X1}$ and $R^{X2}$ are each independently selected from F, Cl, Br, methyl, —OH and dimethylaminomethyl.

At each occurrence, $R^7$, $R^8$ are each independently selected from H, $C_{1-6}$ alkyl, $C_{2-6}$ alkenyl and $C_{2-6}$ alkynyl, wherein the alkyl, alkenyl, alkynyl are optionally substituted with one or more substituents selected from halogen, —NO$_2$, —CN, $C_{1-6}$ alkyl, —OH, —O($C_{1-6}$ alkyl), —NH$_2$, —NH($C_{1-6}$-alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl). In a preferred embodiment, at each occurrence, $R^7$, $R^8$ are each independently selected from H and $C_{1-6}$ alkyl, wherein the alkyl is optionally substituted with one or more substituents selected from halogen, $C_{1-6}$ alkyl, —OH, —O($C_{1-6}$ alkyl), —NH$_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl), and —C(=O)($C_{1-6}$ alkyl). In a particular embodiment, at each occurrence, $R^7$, $R^8$ are each independently selected from H and $C_{1-6}$ alkyl, wherein the alkyl is optionally substituted with one or more substituents selected from halogen, —N($C_{1-6}$ alkyl)$_2$ and —COOH. In another particular embodiment, at each occurrence, $R^7$, $R^8$ are each independently selected from H and $C_{1-6}$ alkyl, wherein the alkyl is optionally substituted with one or more substituents selected from halogen and —N($C_{1-6}$ alkyl)$_2$.

In one embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl-$C_{1-4}$ alkyl, 5- to 10-membered heteroaryl-$C_{1-4}$ alkyl, —OR$^{Y1}$, —SR$^{Y1}$, —NR$^{Y1}$R$^{Y2}$, —C(=O)OR$^{Y1}$, —C(=O)NR$^{Y1}$R$^{Y2}$ and —C(=O)R$^{Y1}$, wherein the alkyl, alkenyl, alkynyl, cyclohydrocarbyl, heterocyclyl, aryl or heteroaryl are optionally substituted with one or more substituents selected from halogen, —OR$^{Y3}$, —SR$^{Y3}$, —NR$^{Y3}$R$^{Y4}$, —C(=O)R$^{Y3}$, —C(=O)OR$^{Y3}$ and —C(=O)NR$^{Y3}$R$^{Y4}$. In a preferred embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, $C_{6-10}$ aryl-$C_{1-4}$ alkyl, 5- to 10-membered heteroaryl-$C_{1-4}$ alkyl, —OR$^{Y1}$, —SR$^{Y1}$, —NR$^{Y1}$R$^{Y2}$, —C(=O)OR$^{Y1}$, —C(=O)NR$^{Y1}$R$^{Y2}$ and —C(=O)R$^{Y1}$, wherein the alkyl, aryl or heteroaryl are optionally substituted with one or more substituents selected from halogen, —OR$^{Y3}$ and —NR$^{Y3}$R$^{Y4}$. In another preferred embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, —OR$^{Y1}$, —NR$^{Y1}$R$^{Y2}$, —C(=O)OR$^{Y1}$, —C(=O)NR$^{Y1}$R$^{Y2}$ and —C(=O)R$^{Y1}$, wherein the alkyl is optionally substituted with one or more substituents selected from halogen, —OR$^{Y3}$ and —NR$^{Y3}$R$^{Y4}$. In a more preferred embodiment, $R^{a1}$, $R^{b1}$, $R^{c1}$, $R^{a2}$, $R^{b2}$, $R^{c2}$ are each independently selected from H, $C_{1-6}$ alkyl, —OR$^{Y1}$, —NR$^{Y1}$R$^{Y2}$ and —C(=O)R$^{Y1}$, wherein the alkyl is optionally substituted with one or more substituents selected from halogen, —OR$^{Y3}$ and —NR$^{Y3}$R$^{Y4}$. In a further embodiment, at each occurrence, at each occurrence, $R^{a1}$, $R^{b1}$, $R^{c1}$, $R^{a2}$, $R^{b2}$, $R^{c2}$ are each independently selected from H, $C_{1-6}$ alkyl, —OR$^{Y1}$, —NR$^{Y1}$R$^{Y2}$ and —C(=O)R$^{Y1}$, wherein the alkyl is optionally substituted with one or more substituents selected from halogen and —NR$^{Y3}$R$^{Y4}$. In a particular embodiment, at each occurrence, $R^{a1}$, $R^{b1}$, $R^{c1}$, $R^{a2}$, $R^{b2}$, $R^{c2}$ are each independently selected from H, $C_{1-3}$ alkyl, —OH and p-methylbenzoyl; wherein the alkyl is optionally substituted with one or more substituents selected from halogen and —NH$_2$.

In another embodiment, at each occurrence, $R^{Y1}$, $R^{Y2}$, $R^{Y3}$, $R^{Y4}$ are each independently selected from H, $C_{1-8}$ alkyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —NO$_2$, —CN, —OH, —SH, —NH$_2$, —COOH and $C_{1-6}$ alkyl. In a preferred embodiment, at each occurrence, $R^{Y1}$, $R^{Y2}$, $R^{Y3}$, $R^{Y4}$ are each independently selected from H, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, phenyl, phenyl-$C_{1-4}$ alkyl, 5- to 6-membered heteroaryl, and 5- to 6-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —NO$_2$, —CN, —OH, —SH, —NH$_2$, —COOH and $C_{1-6}$ alkyl. In a more preferred embodiment, at each occurrence, $R^{Y1}$, $R^{Y2}$, $R^{Y3}$, $R^{Y4}$ are each independently selected from H, $C_{1-6}$ alkyl, phenyl, phenyl-$C_{1-4}$ alkyl, 5- to 6-membered heteroaryl, and 5- to 6-membered heteroaryl-$C_{1-4}$ alkyl, wherein the alkyl or phenyl is optionally substituted with one or more substituents selected from halogen, —NO$_2$, —CN, —OH, —SH, —NH$_2$, —COOH and $C_{1-6}$ alkyl. In a more preferred embodiment, at each occurrence, $R^{Y1}$, $R^{Y2}$, $R^{Y3}$, $R^{Y4}$ are each independently selected from H, $C_{1-6}$ alkyl, phenyl and phenyl-$C_{1-4}$ alkyl, wherein the alkyl or phenyl is optionally substituted with one or more substituents selected from halogen and $C_{1-6}$ alkyl. In a particular embodiment, at each occurrence, $R^{Y1}$, $R^{Y2}$, $R^{Y3}$, $R^{Y4}$ are each independently selected from H and p-methylphenyl.

In another embodiment, R² is selected from H, halogen, —NO₂, —CN, =O, =S, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3- to 7-membered heterocyclyl), —O(C=O)($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —NH₂, —NH($C_{1-6}$ alkyl), —N($C_{1-6}$ alkyl)₂, —NH($C_{3-6}$ cyclohydrocarbyl), —N($C_{3-6}$ cyclohydrocarbyl)₂, —NH($C_{1-4}$ alkylene-$C_{3-6}$ cyclohydrocarbyl), —N($C_{1-4}$ alkylene-$C_{3-6}$ cyclohydrocarbyl)₂, —NH(3- to 7-membered heterocyclyl), —N(3- to 7-membered heterocyclyl)₂, —NH($C_{1-4}$ alkylene-3- to 7-membered heterocyclyl), —N($C_{1-4}$ alkylene-3- to 7-membered heterocyclyl)₂, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl), —NH(C=O)(3- to 7-membered heterocyclyl), —C(=O)($C_{1-6}$ alkyl), —C(=O)O($C_{1-6}$ alkyl), —C(=O)O($C_{3-6}$ cyclohydrocarbyl), —C(=O)O($C_{1-4}$ alkylene-$C_{3-6}$ cyclohydrocarbyl), —C(=O)O(3- to 7-membered heterocyclyl), —C(=O)O($C_{1-4}$ alkylene)-(3- to 7-membered heterocyclyl), —C(=O)NH($C_{1-6}$ alkyl), —C(=O)N($C_{1-6}$ alkyl)₂, —C(=O)NH($C_{1-4}$ alkylene-$C_{3-6}$ cyclohydrocarbyl), —C(=O)N($C_{1-4}$ alkylene-$C_{3-6}$ cyclohydrocarbyl)₂, —C(=O)NH(3- to 7-membered heterocyclyl), —C(=O)N(3- to 7-membered heterocyclyl)₂, —C(=O)NH($C_{1-4}$ alkylene-3- to 7-membered heterocyclyl), and —C(=O)N($C_{1-4}$ alkylene-3- to 7-membered heterocyclyl)₂, wherein the alkyl, alkylene, alkenyl, alkynyl, cyclohydrocarbyl or heterocyclyl are optionally substituted with one or more substituents selected from halogen, nitro, cyano, —OH, —SH and —NH₂. In yet another embodiment, R² is selected from H, halogen, —NO₂, —CN, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —OR^{a1}, —SR^{a1}, —NR^{a1}R^{b1}, —C(=O)OR^{a1}, —C(=O)NR^{a1}R^{b1}, —C(=O)R^{a1}, —S(=O)₂OR^{a1}, —S(=O)₂R^{a1}, —S(=O)₂NR^{a1}R^{b1} and —S(=O)R^{a1}, wherein the alkyl, cyclohydrocarbyl or heterocyclyl are optionally substituted with one or more substituents selected from halogen, —NO₂, —CN, $C_{1-6}$ alkyl, —OR^{a2}, —SR^{a2}, —NR^{a2}R^{b2}, —C(=O)OR^{a2}, —C(=O)NR^{a2}R^{b2} and —C(=O)R^{a2}. In a preferred embodiment, R² is selected from H, halogen, —NO₂, —CN, $C_{1-6}$ alkyl and —OH, wherein the alkyl is optionally substituted with one or more substituents selected from halogen, —NO₂, —CN, $C_{1-6}$ alkyl and —NR^{a2}R^{b2}. In a more preferred embodiment, R² is selected from H, halogen, $C_{1-6}$ alkyl and —OH, wherein the alkyl is optionally substituted with one or more substituents selected from halogen, $C_{1-6}$ alkyl and —NR^{a2}R^{b2}. In a further embodiment, R² is selected from H, $C_{1-4}$ alkyl and —OH, wherein the alkyl is optionally substituted with one or more substituents selected from —NR^{a2}R^{b2}. In a particular embodiment, R² is selected from H, $C_{1-4}$ alkyl and —OH, wherein the alkyl is —CH₂[CH(CH₃)₂] and is optionally substituted with one or more substituents selected from —NR^{a2}R^{b2}. In another embodiment, R² is an alkyl substituted with —NR^{a1}R^{B1}. In a particular embodiment, R² is

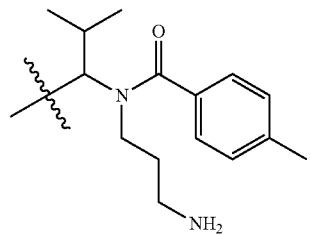

In one embodiment, at each occurrence, $R^{X1}$ and $R^{X2}$ are each independently selected from halogen, —NO₂, —CN, $C_{1-6}$ alkyl, —OW, —SR⁷, —NR⁷R⁸, —C(=O)OR⁷, —C(=O)NR⁷R⁸, —OC(=O)R⁷, —NC(=O)R⁷R⁸, —C(=O)R⁷, —S(=O)₂OR⁷, —S(=O)₂R⁷, —S(=O)₂NR⁷R⁸, —OS(=O)₂R⁷, —NS(=O)₂R⁷R⁸ and —S(=O)R⁷, wherein the alkyl is optionally substituted with one or more substituents selected from halogen, —NO₂, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3 to 7-membered heterocyclyl), —SH, —S($C_{1-6}$ alkyl), —S($C_{3-6}$ cyclohydrocarbyl), —S ($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —NH₂, —NH($C_{1-6}$ alkyl), —N($C_{1-6}$ alkyl)₂, —NH($C_{3-6}$ cyclohydrocarbyl), —N($C_{3-6}$ cyclohydrocarbyl)₂, —NH($C_{1-4}$ alkylene-$C_{3-6}$ cyclohydrocarbyl), —N($C_{1-4}$ alkylene-$C_{3-6}$ cyclohydrocarbyl)₂, —NH(3- to 7-membered heterocyclyl), —N(3- to 7-membered heterocyclyl)₂, —NH($C_{1-4}$ alkylene-3- to 7-membered heterocyclyl), —N($C_{1-4}$ alkylene-3- to 7-membered heterocyclyl)₂, and =O. In a preferred embodiment, at each occurrence, $R^{X1}$ and $R^{X2}$ are each independently selected from halogen, —NO₂, —CN, $C_{1-6}$ alkyl, —OR⁷, —SR⁷, —NR⁷R⁸, —OC(=O)R⁷, —NC(=O)R⁷R⁸, —OS(=O)₂R⁷ and —NS(=O)₂R⁷R⁸, wherein the alkyl is optionally substituted with one or more substituents selected from halogen, —NO₂, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3 to 7-membered heterocyclyl), —O($C_{1-4}$ alkylene)-(3- to 7-membered heterocyclyl), —NH₂, —NH($C_{1-6}$ alkyl), —N($C_{1-6}$ alkyl)₂, —NH($C_{3-6}$ cyclohydrocarbyl), —N($C_{3-6}$ cyclohydrocarbyl)₂, —NH($C_{1-4}$ alkylene-$C_{3-6}$ cyclohydrocarbyl), —N($C_{1-4}$ alkylene-$C_{3-6}$ cyclohydrocarbyl)₂, —NH(3- to 7-membered heterocyclyl), —N(3- to 7-membered heterocyclyl)₂, —NH($C_{1-4}$ alkylene-3- to 7-membered heterocyclyl), and —N($C_{1-4}$ alkylene-3- to 7-membered heterocyclyl)₂. In a preferred embodiment, at each occurrence, $R^{X1}$ and $R^{X2}$ are each independently selected from halogen, $C_{1-6}$ alkyl, —OR⁷ and —NR⁷R⁸, more preferably each independently selected from halogen and —OR⁷, wherein the alkyl is optionally substituted with one or more substituents selected from halogen, —NO₂, —CN, —OH, —O($C_{1-6}$ alkyl), —NH₂, —NH($C_{1-6}$ alkyl) and —N($C_{1-6}$ alkyl)₂. In a more preferred embodiment, at each occurrence, $R^{X1}$ and $R^{X2}$ are each independently selected from F, Cl, Br, —OH, —O($C_{1-6}$ alkyl), —NH₂, —NH($C_{1-6}$ alkyl), —N($C_{1-6}$ alkyl)₂, and optionally substituted $C_{1-6}$ alkyl, wherein the optionally substituted $C_{1-6}$ alkyl is optionally substituted with one or more substituents selected from halogen, —NO₂, —CN, —OH, —O($C_{1-6}$ alkyl), —NH₂, —NH($C_{1-6}$ alkyl) and —N($C_{1-6}$ alkyl)₂. In a particular embodiment, at each occurrence, $R^{X1}$ and $R^{X2}$ are each independently selected from F, Cl, Br, methyl, —OH and dimethylaminomethyl.

At each occurrence, $R^7$, $R^8$ are each independently selected from H, $C_{1-6}$ alkyl, $C_{2-6}$ alkenyl and $C_{2-6}$ alkynyl, wherein the alkyl, alkenyl, alkynyl are optionally substituted with one or more substituents selected from halogen, —$NO_2$, —CN, $C_{1-6}$ alkyl, —OH, —O($C_{1-6}$ alkyl), —$NH_2$, —NH($C_{1-6}$-alkyl), —N($C_{1-6}$ alkyl)$_2$, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl). In a preferred embodiment, at each occurrence, $R^7$, $R^8$ are each independently selected from H and $C_{1-6}$ alkyl, wherein the alkyl is optionally substituted with one or more substituents selected from halogen, $C_{1-6}$ alkyl, —OH, —O($C_{1-6}$ alkyl), —$NH_2$, —NH($C_{1-6}$ alkyl), —N($C_{1-6}$ alkyl)$_2$, —C(=O)O($C_{1-6}$ alkyl), —C(=O)NH ($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl). In a particular embodiment, at each occurrence, $R^7$, $R^8$ are each independently selected from H and $C_{1-6}$ alkyl, wherein the alkyl is optionally substituted with one or more substituents selected from halogen and —N($C_{1-6}$ alkyl)$_2$. In another particular embodiment, at each occurrence, $R^7$, $R^8$ are each independently selected from H and $C_{1-6}$ alkyl, wherein alkyl is optionally substituted with one or more substituents selected from halogen and —N($C_{1-6}$ alkyl)$_2$.

In one embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl-$C_{1-4}$ alkyl, 5- to 10-membered hetero aryl-$C_{1-4}$ alkyl, —$OR^{Y1}$, —$SR^{Y1}$, —$NR^{Y1}R^{Y2}$, —C(=O)$OR^{Y1}$, —C(=O)$NR^{Y1}R^{Y2}$ and —C(=O)$R^{Y1}$, wherein the alkyl, alkenyl, alkynyl, cyclohydrocarbyl, heterocyclyl, aryl or heteroaryl are optionally substituted with one or more substituents selected from halogen, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$. In a preferred embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, $C_{6-10}$ aryl-$C_{1-4}$ alkyl, 5- to 10-membered heteroaryl-$C_{1-4}$ alkyl, —$OR^1$, —$SR^{Y1}$, —$NR^{Y1}R^{Y2}$, —C(=O)$OR^1$, —C(=O)$NR^{Y1}R^{Y2}$ and —C(=O)$R^{Y1}$, wherein the alkyl, aryl or heteroaryl are optionally substituted with one or more substituents selected from halogen, —$OR^3$ and —$NR^{Y3}R^{Y4}$. In another preferred embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, —$OR^1$, —$NR^{Y1}R^{Y2}$, —C(=O)$OR^{Y1}$, —C(=O)$NR^{Y1}R^{Y2}$ and —C(=O)$R^{Y1}$, wherein the alkyl is optionally substituted with one or more substituents selected from halogen, —$OR^3$ and —$NR^{Y3}R^{Y4}$. In a more preferred embodiment, at each occurrence, $R^{a1}$, $R^{b1}$, $R^{c1}$, $R^{a3}$, $R^{b2}$, $R^{c2}$, are each independently selected from H, $C_{1-6}$ alkyl, —$OR^{Y1}$, —$NR^{Y1}R^{Y2}$ and —C(=O)$R^{Y1}$, wherein the alkyl is optionally substituted with one or more substituents selected from halogen, —$OR^3$ and —$NR^{Y3}R^{Y4}$. In a further embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, —$OR^1$, —$NR^{Y1}R^{Y2}$ and —C(=O)$R^{Y1}$, wherein the alkyl is optionally substituted with one or more substituents selected from halogen and —$NR^{Y3}R^{Y4}$. In a particular embodiment, at each occurrence, $R^{a1}$, $R^{b1}$, $R^{c1}$, $R^{a2}$, $R^{b2}$, $R^{c2}$ are each independently selected from H, $C_{1-3}$ alkyl, —OH and p-methylbenzoyl; wherein the alkyl is optionally substituted with one or more substituents selected from halogen and —$NH_2$.

In another embodiment, at each occurrence, $R^{Y1}$, $R^{Y2}$, $R^{Y3}$, $R^{Y4}$ are each independently selected from H, $C_{1-8}$ alkyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, —OH, —SH, —$NH_2$ and $C_{1-6}$ alkyl. In a preferred embodiment, at each occurrence, $R^{Y1}$, $R^{Y2}$, $R^{Y3}$, $R^{Y4}$ are each independently selected from H, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, phenyl, phenyl-$C_{1-4}$ alkyl, 5- to 6-membered heteroaryl, and 5- to 6-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, —OH, —SH, —$NH_2$ and $C_{1-6}$ alkyl. In a more preferred embodiment, at each occurrence, $R^{Y1}$, $R^{Y2}$, $R^{Y3}$, $R^{Y4}$ are each independently selected from H, $C_{1-6}$ alkyl, phenyl, phenyl-$C_{1-4}$ alkyl, 5- to 6-membered heteroaryl, and 5- to 6-membered heteroaryl-$C_{1-4}$ alkyl, wherein the alkyl or phenyl is optionally substituted with one or more substituents selected from halogen, —$NO_2$, —CN, —OH, —SH, —$NH_2$ and $C_{1-6}$ alkyl. In a more preferred embodiment, at each occurrence, $R^{Y1}$, $R^{Y2}$, $R^{Y3}$, $R^{Y4}$ are each independently selected from H, $C_{1-6}$ alkyl, phenyl and phenyl-$C_{1-4}$ alkyl, wherein the alkyl or phenyl is optionally substituted with one or more substituents selected from halogen and $C_{1-6}$ alkyl. In a particular embodiment, at each occurrence, $R^{Y1}$, $R^{Y2}$, $R^{Y3}$, $R^{Y4}$ are each independently selected from H and p-methylphenyl.

In one embodiment, $R^3$, $R^6$ are each independently selected from H, halogen, —$NO_2$, —CN, $C_{1-6}$ alkyl, —OH and —O($C_{1-6}$ alkyl), wherein the alkyl is optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), and —O($C_{1-4}$ alkylene)-(3- to 7-membered heterocyclyl). In a preferred embodiment, $R^3$, $R^6$ are each independently selected from H, halogen and —OH, more preferably is H or —OH.

In one embodiment, $R^4$, $R^5$ are each independently selected from H, halogen, —$NO_2$, —CN, $C_{1-6}$ alkyl, —OH, —O($C_{1-6}$ alkyl), —$NH_2$, —NH($C_{1-6}$ alkyl) and —N($C_{1-6}$ alkyl)$_2$, wherein the alkyl is optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —NH($C_{1-4}$ alkylene-$C_{3-6}$ cyclohydrocarbyl), —NH(3- to 7-membered heterocyclyl), —NH($C_{1-4}$ alkylene-3- to 7-membered heterocyclyl), —COOH, —C(=O)O($C_{1-6}$ alkyl), —C(=O)$NH_2$, —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl), —C(=O)($C_{1-6}$ alkyl) and =O. In another embodiment, $R^4$, $R^5$ are each independently selected from H, halogen, —$NO_2$, —CN, $C_{1-6}$ alkyl, —OH, —O($C_{1-6}$ alkyl), —$NH_2$, —NH($C_{1-6}$ alkyl) and —N($C_{1-6}$ alkyl)$_2$, wherein the alkyl is optionally substituted with one or more substituents selected from halogen, —$NO_2$, —CN, —OH, —O($C_{1-6}$ alkyl), —$NH_2$, —NH($C_{1-6}$ alkyl), —N($C_{1-6}$ alkyl)$_2$, —COOH, —C(=O)O($C_{1-6}$ alkyl), —C(=O)$NH_2$, —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl), —C(=O)($C_{1-6}$ alkyl) and =O. In another embodiment, $R^4$, $R^5$ are each independently selected from H, halogen, —NO₂, —CN, C₁₋₆ alkyl, —OH and —O(C₁₋₆ alkyl), wherein the alkyl is optionally substituted with one or more substituents selected from halogen, —NO₂, —CN, —OH, —O(C₁₋₆ alkyl), —NH₂, —NH(C₁₋₆ alkyl), —N(C₁₋₆ alkyl)₂, —C(=O)O(C₁₋₆ alkyl), —C(=O)NH₂, —C(=O)NH(C₁₋₆ alkyl), —C(=O)N(C₁₋₆ alkyl)₂, —OC(=O)(C₁₋₆ alkyl), —NHC(=O)(C₁₋₆ alkyl), —C(=O)(C₁₋₆ alkyl) and =O. In another embodiment, R⁴, R⁵ are each independently selected from H, halogen, —NO₂, —CN, C₁₋₆ alkyl, —NH₂, —NH(C₁₋₆ alkyl) and —N(C₁₋₆ alkyl)₂, wherein the alkyl is optionally substituted with one or more substituents selected from halogen, —NO₂, —CN, —OH, —O(C₁₋₆ alkyl), —NH₂, —NH(C₁₋₆ alkyl), —N(C₁₋₆ alkyl)₂, —C(=O)O(C₁₋₆ alkyl), —C(=O)NH₂, —C(=O)NH(C₁₋₆ alkyl), —C(=O)N(C₁₋₆ alkyl)₂, —OC(=O)(C₁₋₆ alkyl), —NHC(=O)(C₁₋₆ alkyl), —C(=O)(C₁₋₆ alkyl) and =O.

The structure described in the following formula (VII) falls within the scope of the structure described in formula (I), formula (III) and formula (VI). In another aspect of the present invention, provided is use of a compound of formula (VII), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder.

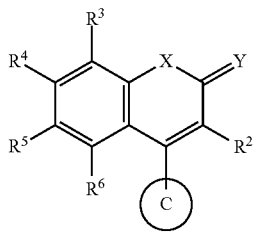
(VII)

wherein
X is O;
Y, R³, R⁴, R⁵, R⁶ are as defined in formula (VI);
ring C is

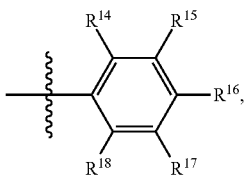

wherein R¹⁴, R¹⁵, R¹⁶, R¹⁷, R¹⁸ are each independently selected from H, halogen, —NO₂, —CN, C₁₋₆ alkyl, C₂₋₆ alkenyl, C₂₋₆ alkynyl, —OR⁷, —SR⁷, —NR⁷R⁸, —C(=O)OR⁷, —C(=O)NR⁷R⁸, —OC(=O)R⁷, —NC(=O)R⁷R⁸, —C(=O)R⁷, —S(=O)₂OR⁷, —S(=O)₂R⁷, —S(=O)₂NR⁷R⁸, —OS(=O)₂R⁷, —NS(=O)₂R⁷R⁸ and —S(=O)R⁷; wherein R⁷, R⁸ are as defined in formula (VI);
R² is selected from H, halogen, C₁₋₆ alkyl, C₃₋₆ cyclohydrocarbyl, C₃₋₆ cyclohydrocarbyl-C₁₋₄ alkyl, 3- to 7-membered heterocyclyl, and 3- to 7-membered heterocyclyl-C₁₋₄ alkyl, wherein the alkyl, cyclohydrocarbyl or heterocyclyl are optionally substituted with one or more substituents selected from halogen, —NO₂, —CN, C₁₋₆ alkyl, —OR^{a2}, —SR^{a2}, —NR^{a2}R^{b2}, —C(=O)OR^{a2}, —C(=O)NR^{a2}R^{b2}, —C(=O)R^{a2}, —S(=O)₂OR^{a2}, —S(=O)₂R^{a2}, —S(=O)₂NR^{a2}R^{b2} and —S(=O)R^{a2}; wherein R^{a2}, R^{b2}, R^{c2} are as defined in formula (VI);

provided that the compound of formula (VII) does not include the following structure:

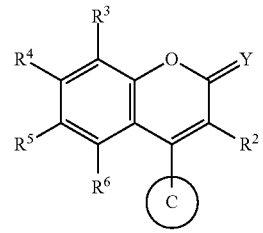

wherein R⁴ is selected from —O(C₁₋₆ alkyl) and —O(C₁₋₄ alkylene-C₆₋₁₀ aryl).

In one embodiment, Y is O. When Y is O, formula (VII) is

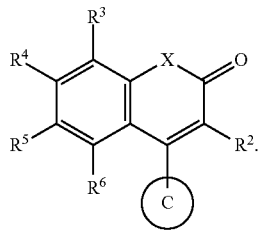

In one embodiment, R² is selected from H, halogen and C₁₋₆ alkyl, wherein the alkyl is optionally substituted with one or more substituents selected from halogen, —NO₂, —CN, C₁₋₆ alkyl, —OR^{a2}, —SR^{a2}, —NR^{a2}R^{b2}, —C(=O)OR^{a2}, —C(=O)NR^{a2}R^{b2}, —C(=O)R^{a2}, —S(=O)₂OR^{a2}, —S(=O)₂R^{a2}, —S(=O)₂NR^{a2}R^{b2} and —S(=O)R^{a2}. In one embodiment, R² is selected from —OR^{a1}, —NR^{a1}R^{b1}, —C(=O)OR^{a1} and —C(=O)NR^{a1}R^{b1}. In another embodiment, R² is selected from H, halogen and C₁₋₆ alkyl, wherein the alkyl is optionally substituted with one or more substituents selected from halogen, —NO₂, —CN, —OH, —NH₂ and —COOH.

In one embodiment, at each occurrence, R^{a2}, R^{b2}, R^{c2} are each independently selected from H, C₁₋₆ alkyl, C₃₋₆ cyclohydrocarbyl, C₃₋₆ cyclohydrocarbyl-C₁₋₄ alkyl, 3- to 7-membered heterocyclyl, and 3- to 7-membered heterocyclyl-C₁₋₄ alkyl, wherein the alkyl, alkenyl, alkynyl, cyclohydrocarbyl or heterocyclyl are optionally substituted with one or more substituents selected from halogen, —OH, —O(C₁₋₆ alkyl), —NH₂, —NH(C₁₋₆ alkyl), —N(C₁₋₆ alkyl)₂, —COOH, —C(=O)O(C₁₋₆ alkyl), —C(=O)NH(C₁₋₆ alkyl) and —C(=O)N(C₁₋₆ alkyl)₂. In a preferred embodiment, at each occurrence, R^{a2}, R^{b2}, R^{c2} are each independently selected from H and C₁₋₆-alkyl, wherein the alkyl is optionally substituted with one or more substituents selected from halogen, —OH, —NH₂, —NH(C₁₋₆ alkyl), —N(C₁₋₆ alkyl)₂, —COOH, —C(=O)O(C₁₋₆ alkyl), —C(=O)NH(C₁₋₆ alkyl) and —C(=O)N(C₁₋₆ alkyl)₂.

In one embodiment, R³ is selected from H, halogen, C₁₋₆ alkyl, —OH, —O(C₁₋₆ alkyl), —NH₂, —NH(C₁₋₆ alkyl) and —N(C₁₋₆ alkyl)₂, wherein the alkyl is optionally substituted with one or more substituents selected from halogen, —OH, —O(C₁₋₆ alkyl), —NH₂, —NH(C₁₋₆ alkyl) and —N(C₁₋₆ alkyl)$_2$. In one embodiment, $R^3$ is selected from H, halogen, C$_{1-3}$ alkyl, —OH, —O(C$_{1-3}$ alkyl), —NH$_2$, —NH(C$_{1-3}$ alkyl) and —N(C$_{1-3}$ alkyl)$_2$, wherein the alkyl is optionally substituted with one or more substituents selected from halogen, —OH, —O(C$_{1-2}$ alkyl), —NH$_2$, —NH(C$_{1-2}$ alkyl) and —N(C$_{1-2}$ alkyl)$_2$. In one embodiment, $R^3$ is selected from H, halogen, methyl, —OH, —OCH$_3$, —NH$_2$, —NHCH$_3$ and —N(CH$_3$)$_2$, wherein the methyl is optionally substituted with substituents selected from halogen, —OH, —O(C$_{1-2}$ alkyl), —NH$_2$, —NH(C$_{1-2}$ alkyl) and —N(C$_{1-2}$ alkyl)$_2$. In one embodiment, $R^3$ is selected from H, halogen, methyl, —OH, —OCH$_3$, —NH$_2$, —NHCH$_3$ and —N(CH$_3$)$_2$, wherein the methyl is optionally substituted with substituents selected from halogen, —OH, —OCH$_3$, —NH$_2$, —NHCH$_3$ and —N(CH$_3$)$_2$. In one embodiment, $R^3$ is selected from H, halogen, methyl, —OH, —NH$_2$ and —N(CH$_3$)$_2$. In yet another embodiment, $R^3$ is selected from H, halogen, C$_{1-4}$ alkyl, —OH, —O(C$_{1-4}$ alkyl), —NH$_2$ and —NH(C$_{1-4}$ alkyl), wherein the alkyl is optionally substituted with one or more substituents selected from halogen, —OH, —O(C$_{1-4}$ alkyl), —NH$_2$ and —NH(C$_{1-4}$ alkyl). In one embodiment, $R^3$ is selected from H, halogen, methyl, —OH, —OCH$_3$, —NH$_2$ and —NHCH$_3$, wherein the methyl is optionally substituted with substituents selected from halogen, —OH, —O(C$_{1-2}$ alkyl), —NH$_2$ and —NH(C$_{1-2}$ alkyl). In one embodiment, $R^3$ is selected from H, halogen, methyl, —OH, —OCH$_3$, —NH$_2$ and —NHCH$_3$, wherein the methyl is optionally substituted with substituents selected from halogen, —OH, —OCH$_3$, —NH$_2$ and —NHCH$_3$. In another embodiment, $R^3$ is selected from H, halogen, C$_{1-4}$ alkyl, —OH, —O(C$_{1-4}$ alkyl) and —NH$_2$, wherein the alkyl is optionally substituted with one or more substituents selected from halogen, —OH, —O(C$_{1-4}$ alkyl) and —NH$_2$. In one embodiment, $R^3$ is selected from H, halogen, methyl, —OH, —OCH$_3$ and —NH$_2$, wherein the methyl is optionally substituted with substituents selected from halogen, —OH, —O(C$_{1-2}$ alkyl) and —NH$_2$. In one embodiment, $R^3$ is selected from H, halogen, methyl, —OH, —OCH$_3$ and —NH$_2$, wherein the methyl is optionally substituted with substituents selected from halogen, —OH, —OCH$_3$ and —NH$_2$. In one embodiment, $R^3$ is selected from H, halogen, methyl, —OH and —NH$_2$. In another embodiment, $R^3$ is selected from H, halogen, C$_{1-4}$ alkyl, —OH and —O(C$_{1-4}$ alkyl), wherein the alkyl is optionally substituted with one or more substituents selected from halogen, —OH and —O(C$_{1-4}$ alkyl). In one embodiment, $R^3$ is selected from H, halogen, methyl, —OH and —OCH$_3$, wherein the methyl is optionally substituted with substituents selected from halogen, —OH and —O(C$_{1-2}$ alkyl). In one embodiment, $R^3$ is selected from H, halogen, methyl, —OH and —OCH$_3$, wherein the methyl is optionally substituted with substituents selected from halogen, —OH and —OCH$_3$. In one embodiment, $R^3$ is selected from H, halogen, methyl and —OH. In yet another embodiment, $R^3$ is selected from H, halogen, —OH, —O(C$_{1-4}$ alkyl), —NH$_2$, —NH(C$_{1-4}$ alkyl), —N(C$_{1-4}$ alkyl)$_2$, and substituted C$_{1-4}$ alkyl, wherein the substituted C$_{1-4}$ alkyl is substituted with one or more substituents selected from halogen, —OH, —O(C$_{1-4}$ alkyl), —NH$_2$, —NH(C$_{1-4}$ alkyl) and —N(C$_{1-4}$ alkyl)$_2$. In one embodiment, $R^3$ is selected from H, halogen, —OH, —OCH$_3$, —NH$_2$, —NHCH$_3$, —N(CH$_3$)$_2$, and substituted methyl, wherein the substituted methyl is substituted with substituent(s) selected from halogen, —OH, —O(C$_{1-2}$ alkyl), —NH(C$_{1-2}$ alkyl) and —N(C$_{1-2}$ alkyl)$_2$. In one embodiment, $R^3$ is selected from H, halogen, —OH, —OCH$_3$, —NH$_2$, —NHCH$_3$, —N(CH$_3$)$_2$, and substituted methyl, wherein the substituted methyl is substituted with substituent(s) selected from halogen, —OH, —OCH$_3$, —NHCH$_3$ and —N(CH$_3$)$_2$. In one embodiment, $R^3$ is selected from H, halogen, —OH, —NH$_2$ and methyl, wherein the methyl is substituted by —N(CH$_3$)$_2$. In yet another embodiment, $R^3$ is selected from H, halogen, —OH, —O(C$_{1-4}$ alkyl), and substituted C$_{1-4}$ alkyl, wherein the substituted C$_{1-4}$ alkyl is substituted with one or more substituents selected from halogen, —OH, —O(C$_{1-4}$ alkyl), —NH$_2$, —NH(C$_{1-4}$ alkyl) and —N(C$_{1-4}$ alkyl)$_2$. In one embodiment, $R^3$ is selected from H, halogen, —OH, —OCH$_3$, and substituted methyl, wherein the substituted methyl is substituted with substituent(s) selected from halogen, —OH, —O(C$_{1-2}$ alkyl), —NH(C$_{1-2}$ alkyl) and —N(C$_{1-2}$ alkyl)$_2$. In one embodiment, $R^3$ is selected from H, halogen, —OH, —OCH$_3$, and substituted methyl, wherein the substituted methyl is substituted with substituent(s) selected from halogen, —OH, —OCH$_3$, —NHCH$_3$ and —N(CH$_3$)$_2$. In one embodiment, $R^3$ is selected from H, halogen, —OH and methyl, wherein the methyl is substituted with —N(CH$_3$)$_2$. In another embodiment, $R^3$ is selected from H, halogen, —OH, —O(C$_{1-4}$ alkyl), and substituted C$_{1-4}$ alkyl, wherein the substituted C$_{1-4}$ alkyl is substituted with one or more substituents selected from halogen, —NH$_2$, —NH(C$_{1-4}$ alkyl) and —N(C$_{1-4}$ alkyl)$_2$. In one embodiment, $R^3$ is selected from H, halogen, —OH and C$_{1-2}$ alkyl, wherein the alkyl is substituted with one or more substituents selected from halogen, —NH(C$_{1-2}$ alkyl) and —N(C$_{1-2}$ alkyl)$_2$. In one embodiment, $R^3$ is selected from H, halogen, —OH and methyl, wherein the methyl is substituted with substituent(s) selected from selected from halogen, —NH(C$_{1-2}$ alkyl) and —N(C$_{1-2}$ alkyl)$_2$. In one embodiment, $R^3$ is selected from H, halogen, —OH and methyl, wherein the methyl is substituted with substituent(s) selected from halogen, —NHCH$_3$ and —N(CH$_3$)$_2$. In one embodiment, $R^3$ is selected from H, halogen, —OH and methyl, wherein the methyl is substituted with —N(CH$_3$)$_2$. In yet another embodiment, $R^3$ is selected from H, halogen, —OH, —O(C$_{1-4}$ alkyl), —NH$_2$, —NH(C$_{1-4}$ alkyl), and substituted C$_{1-4}$ alkyl, wherein the substituted C$_{1-4}$ alkyl is substituted with one or more substituents selected from halogen, —OH, —O(C$_{1-4}$ alkyl), —NH$_2$ and —NH(C$_{1-4}$ alkyl). In one embodiment, $R^3$ is selected from H, halogen, —OH, —OCH$_3$, —NH$_2$, —NHCH$_3$, and substituted methyl, wherein the substituted methyl is substituted with substituent(s) selected from halogen, —OH, —O(C$_{1-2}$ alkyl) and —NH(C$_{1-2}$ alkyl). In one embodiment, $R^3$ is selected from H, halogen, —OH, —OCH$_3$, —NH$_2$, —NHCH$_3$, and substituted methyl, wherein the substituted methyl is substituted with substituent(s) selected from halogen, —OH, —OCH$_3$ and —NHCH$_3$. In one embodiment, $R^3$ is selected from H, halogen, —OH, —NH$_2$ and methyl, wherein the methyl is substituted by —N(CH$_3$)$_2$. In yet another embodiment, $R^3$ is selected from H, halogen, —OH, —O(C$_{1-4}$ alkyl), and substituted C$_{1-4}$ alkyl, wherein the substituted C$_{1-4}$ alkyl is substituted with one or more substituents selected from halogen, —OH, —O(C$_{1-4}$ alkyl), —NH$_2$ and —NH(C$_{1-4}$ alkyl). In one embodiment, $R^3$ is selected from H, halogen, —OH, —OCH$_3$, and substituted methyl, wherein the substituted methyl is substituted with substituent(s) selected from halogen, —OH, —O(C$_{1-2}$ alkyl) and —NH(C$_{1-2}$ alkyl). In one embodiment, $R^3$ is selected from H, halogen, —OH, —OCH$_3$, and substituted methyl, wherein the substituted methyl is substituted with substituent(s) selected from halogen, —OH, —OCH$_3$ and —NHCH$_3$. In one embodiment, $R^3$ is selected from H, halogen, —OH and methyl, wherein the methyl is substituted with —N(CH$_3$)$_2$. In another embodiment, $R^3$ is selected from H, halogen, —OH, —O(C$_{1-4}$ alkyl), and substituted $C_{1-4}$ alkyl, wherein the substituted $C_{1-4}$ alkyl is substituted with one or more substituents selected from halogen, —$NH_2$ and —$NH(C_{1-4}$ alkyl). In one embodiment, $R^3$ is selected from H, halogen, —OH and $C_{1-2}$ alkyl, wherein the alkyl is substituted with one or more substituents selected from halogen and —$NH(C_{1-2}$ alkyl). In one embodiment, $R^3$ is selected from H, halogen, —OH and methyl, wherein the methyl is substituted with substituent(s) selected from halogen and —$NH(C_{1-2}$ alkyl). In one embodiment, $R^3$ is selected from H, halogen, —OH and methyl, wherein the methyl is substituted with substituent(s) selected from halogen and —$NHCH_3$. In one embodiment, $R^3$ is selected from H, F, Cl, methyl, —OH and —$NH_2$. In another embodiment, $R^3$ is selected from H, F, methyl, —OH and —$NH_2$. In one embodiment, $R^3$ is H. In one embodiment, $R^3$ is —OH. In one embodiment, $R^3$ is $CH_3$.

In one embodiment, $R^4$ is selected from H, halogen, —$NO_2$, —CN, $C_{1-6}$ alkyl, —OH, —$O(C_{1-6}$ alkyl), —$NH_2$, —$NH(C_{1-6}$ alkyl) and —$N(C_{1-6}$ alkyl)$_2$, wherein the alkyl is optionally substituted with one or more substituents selected from halogen, —OH, —$O(C_{1-6}$ alkyl), —$NH_2$, —$NH(C_{1-6}$ alkyl) and —$N(C_{1-6}$ alkyl)$_2$. In one embodiment, $R^4$ is selected from H, halogen, —OH, —$O(C_{1-4}$ alkyl), —$NH_2$, —$NH(C_{1-4}$ alkyl), —$N(C_{1-4}$ alkyl)$_2$, and substituted $C_{1-4}$ alkyl, wherein the substituted $C_{1-4}$ alkyl is substituted with one or more substituents selected from halogen, —OH, —$O(C_{1-4}$ alkyl), —$NH_2$, —$NH(C_{1-4}$ alkyl) and —$N(C_{1-4}$ alkyl)$_2$. In one embodiment, $R^4$ is selected from H, halogen, —OH, —$O(C_{1-3}$ alkyl), —$NH_2$, —$NH(C_{1-3}$ alkyl), —$N(C_{1-3}$ alkyl)$_2$, and substituted $C_{1-3}$ alkyl, wherein the substituted $C_{1-3}$ alkyl is optionally substituted with one or more substituents selected from halogen, —OH, —$O(C_{1-2}$ alkyl), —$NH_2$, —$NH(C_{1-2}$ alkyl) and —$N(C_{1-2}$ alkyl)$_2$. In one embodiment, $R^4$ is selected from H, halogen, —OH, —$NH_2$, —$NH(C_{1-4}$ alkyl), substituted $C_{1-4}$ alkyl, substituted —$O(C_{1-4}$ alkyl), and substituted —$N(C_{1-4}$ alkyl)$_2$, wherein the substituted $C_{1-4}$ alkyl, substituted —$O(C_{1-4}$ alkyl) and substituted —$N(C_{1-4}$ alkyl)$_2$ are substituted with one or more substituents selected from halogen, —OH, —$O(C_{1-2}$ alkyl), —$NH_2$ and —$NH(C_{1-4}$ alkyl). In one embodiment, $R^4$ is selected from H, halogen, —OH, —$O(C_{1-2}$ alkyl), —$NH_2$, —$NH(C_{1-2}$ alkyl), substituted $C_{1-2}$ alkyl, and substituted —$O(C_{1-2}$ alkyl), wherein the substituted $C_{1-2}$ alkyl and substituted —$O(C_{1-2}$ alkyl) are substituted with one or more substituents selected from halogen, —OH, —$O(C_{1-2}$ alkyl), —$NH_2$ and —$NH(C_{1-4}$ alkyl). In one embodiment, $R^4$ is selected from H, halogen, —OH, —$OCH_3$, —$NH_2$, —$NHCH_3$, and substituted $C_{1-2}$ alkyl, wherein the substituted $C_{1-2}$ alkyl is substituted with one or more substituents selected from halogen, —OH, —$OCH_3$, —$NH_2$ and —$NHCH_3$. In one embodiment, $R^4$ is selected from H, halogen, —OH, —$NH_2$, —$NH(C_{1-4}$ alkyl), and substituted $C_{1-4}$ alkyl, wherein the substituted $C_{1-4}$ alkyl is substituted with one or more substituents selected from halogen, —OH, —$OCH_3$, —$NH_2$ and —$NH(C_{1-4}$ alkyl). In one embodiment, $R^4$ is selected from H, halogen, —OH, —$NH_2$, —$NH(C_{1-2}$ alkyl), —$N(C_{1-2}$ alkyl)$_2$, and substituted $C_{1-2}$ alkyl, wherein the substituted $C_{1-2}$ alkyl is substituted with one or more substituents selected from halogen, —OH, —$O(C_{1-2}$ alkyl), —$NH_2$ and —$NH(C_{1-2}$ alkyl). In one embodiment, $R^4$ is selected from H, halogen, —OH, —$NH_2$, —$NHCH_3$, and substituted $C_{1-2}$ alkyl, wherein the substituted $C_{1-2}$ alkyl is substituted with one or more substituents selected from halogen, —OH, —$OCH_3$, —$NH_2$ and —$NHCH_3$. In one embodiment, $R^4$ is selected from H, halogen, $C_{1-4}$ alkyl, —OH and —$O(C_{1-4}$ alkyl), wherein the alkyl is optionally substituted with one or more substituents selected from halogen, —OH, —$O(C_{1-4}$ alkyl), —$NH_2$, —$NH(C_{1-4}$ alkyl) and —$N(C_{1-4}$ alkyl)$_2$. In one embodiment, $R^4$ is selected from H, halogen, $C_{1-2}$ alkyl, —OH and —$OCH_3$, wherein the alkyl is optionally substituted with one or more substituents selected from halogen, —OH, —$OCH_3$, —$NH_2$, —$NHCH_3$ and —$N(CH_3)_2$. In one embodiment, $R^4$ is selected from H, halogen, $C_{1-4}$ alkyl, —OH, —$O(C_{1-4}$ alkyl), —$NH_2$, —$NH(C_{1-4}$ alkyl) and —$N(C_{1-4}$ alkyl)$_2$, wherein the alkyl is optionally substituted with one or more substituents selected from halogen, —OH and —$O(C_{1-4}$ alkyl). In one embodiment, $R^4$ is selected from H, halogen, $C_{1-2}$ alkyl, —OH, —$OCH_3$, —$NH_2$, —$NHCH_3$ and —$N(CH_3)_2$, wherein the alkyl is optionally substituted with one or more substituents selected from halogen, —OH and —$OCH_3$. In one embodiment, $R^4$ is selected from H, halogen, $C_{1-4}$ alkyl, —OH and —$O(C_{1-4}$ alkyl), wherein the alkyl is optionally substituted with one or more substituents selected from halogen, —OH and —$O(C_{1-4}$ alkyl). In one embodiment, $R^4$ is selected from H, halogen, $C_{1-2}$ alkyl, —OH and —$OCH_3$, wherein the alkyl is optionally substituted with one or more substituents selected from halogen, —OH and —$OCH_3$. In one embodiment, $R^4$ is selected from H, —OH and —$OCH_3$. In one embodiment, $R^4$ is H. In one embodiment, $R^4$ is —OH.

In one embodiment, $R^5$ is selected from H, halogen, —$NO_2$, —CN, $C_{1-6}$ alkyl, —OH, —$O(C_{1-6}$ alkyl), —$NH_2$, —$NH(C_{1-6}$ alkyl), —$N(C_{1-6}$ alkyl)$_2$, —$C(=O)O(C_{1-6}$ alkyl), —$C(=O)NH(C_{1-6}$ alkyl), —$C(=O)N(C_{1-6}$ alkyl)$_2$, —$OC(=O)(C_{1-6}$ alkyl), —$NHC(=O)(C_{1-6}$ alkyl) and —$C(=O)(C_{1-6}$ alkyl), wherein the alkyl is optionally substituted with one or more substituents selected from halogen, —OH, —$O(C_{1-6}$ alkyl), —$NH_2$, —$NH(C_{1-6}$ alkyl), —$N(C_{1-6}$ alkyl)$_2$, —$C(=O)O(C_{1-6}$ alkyl), —$C(=O)NH(C_{1-6}$ alkyl), —$C(=O)N(C_{1-6}$ alkyl)$_2$, —$OC(=O)(C_{1-6}$ alkyl), —$NHC(=O)(C_{1-6}$ alkyl) and —$C(=O)(C_{1-6}$ alkyl). In one embodiment, $R^5$ is selected from H, halogen, $C_{1-4}$ alkyl, —OH, —$O(C_{1-4}$ alkyl), —$NH_2$, —$NH(C_{1-4}$ alkyl) and —$N(C_{1-4}$ alkyl)$_2$, wherein the alkyl is optionally substituted with one or more substituents selected from halogen, —OH, —$O(C_{1-4}$ alkyl), —$NH_2$, —$NH(C_{1-4}$ alkyl) and —$N(C_{1-4}$ alkyl)$_2$. In one embodiment, $R^5$ is selected from H, halogen, —OH, —$O(C_{1-4}$ alkyl), —$NH_2$, —$NH(C_{1-4}$ alkyl), —$N(C_{1-4}$ alkyl)$_2$, —$C(=O)O(C_{1-4}$ alkyl), —$C(=O)NH_2$, —$C(=O)NH(C_{1-4}$ alkyl), —$C(=O)N(C_{1-4}$ alkyl)$_2$, —$OC(=O)(C_{1-4}$ alkyl), —$NC(=O)(C_{1-4}$ alkyl)$_2$, —$C(=O)(C_{1-4}$ alkyl), and substituted $C_{1-4}$ alkyl, wherein the substituted $C_{1-4}$ alkyl is substituted with one or more substituents selected from halogen, —OH, —$O(C_{1-4}$ alkyl), —$NH_2$, —$NH(C_{1-4}$ alkyl), —$N(C_{1-4}$ alkyl)$_2$, —$C(=O)O(C_{1-4}$ alkyl), —$C(=O)NH_2$, —$C(=O)NH(C_{1-4}$ alkyl), —$C(=O)$ $N(C_{1-4}$ alkyl)$_2$, —$OC(=O)(C_{1-4}$ alkyl), —$NC(=O)(C_{1-4}$ alkyl)$_2$ and —$C(=O)(C_{1-4}$ alkyl). In one embodiment, $R^5$ is selected from H, halogen, —OH, —$O(C_{1-4}$ alkyl), —$NH_2$, —$NH(C_{1-4}$ alkyl), —$N(C_{1-4}$ alkyl)$_2$, and substituted $C_{1-4}$ alkyl, wherein the substituted $C_{1-4}$ alkyl is substituted with one or more substituents selected from halogen, —OH, —$O(C_{1-4}$ alkyl), —$NH_2$, —$NH(C_{1-4}$ alkyl) and —$N(C_{1-4}$ alkyl)$_2$. In one embodiment, $R^5$ is selected from H, halogen, —$O(C_{1-4}$ alkyl), —$NH(C_{1-4}$ alkyl), —$N(C_{1-4}$ alkyl)$_2$, and substituted $C_{1-2}$ alkyl, wherein the substituted $C_{1-2}$ alkyl is substituted with one or more substituents selected from halogen, —$O(C_{1-4}$ alkyl), —$NH(C_{1-4}$ alkyl) and —$N(C_{1-4}$ alkyl)$_2$. In one embodiment, $R^5$ is selected from H, halogen, —$O(C_{1-4}$ alkyl), —$NH(C_{1-4}$ alkyl), —$N(C_{1-4}$ alkyl)$_2$, and substituted $C_{1-2}$ alkyl, wherein the substituted $C_{1-2}$ alkyl is substituted with one or more substituents selected from halogen, —$OCH_3$, —$NHCH_3$ and —$N(CH_3)_2$. In one embodiment, $R^5$ is selected from H, halogen, —O($C_{1-2}$ alkyl), —NH($C_{1-2}$ alkyl), —N($C_{1-2}$ alkyl)$_2$, and substituted $C_{1-2}$ alkyl, wherein the substituted $C_{1-2}$ alkyl is substituted with one or more substituents selected from halogen, —OCH$_3$, —NHCH$_3$ and —N(CH$_3$)$_2$.

In one embodiment, $R^6$ is selected from H, halogen, —NO$_2$, —CN, $C_{1-6}$ alkyl, —OH, —O($C_{1-6}$ alkyl), —NH$_2$, —NH($C_{1-6}$ alkyl) and —N($C_{1-6}$ alkyl)$_2$, wherein the alkyl is optionally substituted with one or more substituents selected from halogen, —OH, —O($C_{1-6}$ alkyl), —NH$_2$, —NH($C_{1-6}$ alkyl) and —N($C_{1-6}$ alkyl)$_2$. In another embodiment, $R^6$ is selected from H, halogen, —NO$_2$, —CN, $C_{1-6}$ alkyl, —OH, —O($C_{1-6}$ alkyl), —NH$_2$, —NH($C_{1-6}$ alkyl) and —N($C_{1-6}$ alkyl)$_2$, wherein the alkyl is optionally substituted with one or more substituents selected from halogen, —OH and —NH$_2$. In one embodiment, $R^6$ is selected from H, halogen, —NO$_2$, —CN, $C_{1-2}$ alkyl, —OH, —O($C_{1-2}$ alkyl), —NH$_2$, —NH($C_{1-2}$ alkyl) and —N($C_{1-2}$ alkyl)$_2$, wherein the alkyl is optionally substituted with one or more substituents selected from halogen, —OH and —NH$_2$. In yet another embodiment, $R^6$ is selected from H, halogen, —NO$_2$, —CN, $C_{1-4}$ alkyl, —OH, —O($C_{1-4}$ alkyl), —NH$_2$, —NH($C_{1-4}$ alkyl) and —N($C_{1-4}$ alkyl)$_2$, wherein the alkyl is optionally substituted with one or more halogen. In another embodiment, $R^6$ is selected from H, halogen, —NO$_2$, —CN, $C_{1-2}$ alkyl, —OH, —O($C_{1-2}$ alkyl), —NH$_2$, —NH($C_{1-4}$ alkyl) and —N($C_{1-4}$ alkyl)$_2$. In one embodiment, $R^6$ is selected from H, F, Cl, Br, $C_{1-6}$ alkyl, —OH and —NH$_2$, wherein the alkyl is optionally substituted with one or more substituents selected from halogen, —OH and —NH$_2$. In another embodiment, $R^6$ is selected from H, F, Cl, Br, methyl, —OH and —NH$_2$. In a particular embodiment, $R^6$ is H or —OH, especially H.

In one embodiment, $R^3$ is methyl, and $R^4$ is selected from —OH, —NH$_2$, —NH($C_{1-3}$ alkyl), —N($C_{1-3}$ alkyl)$_2$, and $C_{1-3}$ alkyl substituted with —COOH, wherein the substituted $C_{1-3}$ alkyl is substituted with one or more substituents selected from —OH, —NH$_2$, —NH($C_{1-2}$ alkyl), —N($C_{1-2}$ alkyl)$_2$ and —COOH. In one embodiment, $R^3$ is methyl, and $R^4$ is selected from —NH$_2$, —NH($C_{1-3}$ alkyl), —N($C_{1-3}$ alkyl)$_2$, and $C_{1-3}$ alkyl substituted with —COOH, wherein the substituted $C_{1-3}$ alkyl is substituted with one or more substituents selected from —OH, —NH$_2$, —NH($C_{1-2}$ alkyl), —N($C_{1-2}$ alkyl)$_2$ and —COOH.

In another embodiment, $R^3$ is methyl and $R^5$ is selected from —OH, —NH$_2$, —NH($C_{1-3}$ alkyl), —N($C_{1-3}$ alkyl)$_2$, and $C_{1-3}$ alkyl substituted with —COOH, wherein the substituted $C_{1-3}$ alkyl is substituted with one or more substituents selected from —OH, —NH$_2$, —NH($C_{1-2}$ alkyl), —N($C_{1-2}$ alkyl)$_2$ and —COOH. In another embodiment, $R^3$ is methyl, and $R^5$ is selected from —NH$_2$, —NH($C_{1-3}$ alkyl), —N($C_{1-3}$ alkyl)$_2$, and $C_{1-3}$ alkyl substituted with —COOH, wherein the substituted $C_{1-3}$ alkyl is substituted with one or more substituents selected from —OH, —NH$_2$, —NH($C_{1-2}$ alkyl), —N($C_{1-2}$ alkyl)$_2$ and —COOH.

In one embodiment, $R^{14}$, $R^{15}$, $R^{16}$, $R^{17}$, $R^{18}$ are each independently selected from H, halogen, —NO$_2$, —CN, $C_{1-6}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3- to 7-membered heterocyclyl), —O(C=O)($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —NH$_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl), —NH(C=O)(3- to 7-membered heterocyclyl), —C(=O)($C_{1-6}$ alkyl), —C(=O)O($C_{1-6}$ alkyl), —C(=O)O($C_{3-6}$ cyclohydrocarbyl), —C(=O)O($C_{1-4}$ alkylene-$C_{3-6}$ cyclohydrocarbyl), —C(=O)O(3- to 7-membered heterocyclyl), —C(=O)O($C_{1-4}$ alkylene)-(3- to 7-membered heterocyclyl), —C(=O)NH$_2$, —C(=O)NH($C_{1-6}$ alkyl), —C(=O)N($C_{1-6}$ alkyl)$_2$, —C(=O)NH($C_{1-4}$ alkylene-$C_{3-6}$ cyclohydrocarbyl), —C(=O)N($C_{1-4}$ alkylene-$C_{3-6}$ cyclohydrocarbyl)$_2$, —C(=O)NH(3- to 7-membered heterocyclyl), —C(=O)N(3- to 7-membered heterocyclyl)$_2$, —C(=O)NH($C_{1-4}$ alkylene-3- to 7-membered heterocyclyl), and —C(=O)N($C_{1-4}$ alkylene-3- to 7-membered heterocyclyl)$_2$, wherein the alkyl, alkylene, alkenyl, alkynyl, cyclohydrocarbyl or heterocyclyl are optionally substituted with one or more substituents selected from H, halogen, nitro, cyano, —SH, —NH$_2$, =O and —COOH. In one embodiment, $R^{14}$, $R^{15}$, $R^{16}$, $R^{17}$, $R^{18}$ are each independently selected from H, halogen, —NO$_2$, —CN, $C_{1-6}$ alkyl, —OR$^7$, —NR$^7$R$^8$, —C(=O)OR$^7$, —C(=O)NR$^7$R$^8$, —OC(=O)R$^7$, —NC(=O)R$^7$R$^8$ and —C(=O)R$^7$. In one embodiment, $R^{14}$, $R^{15}$, $R^{16}$, $R^{17}$, $R^{18}$ are each independently selected from H, halogen, —NO$_2$, —CN, $C_{1-6}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3 to 7-membered heterocyclyl), —O(C=O)($C_{1-4}$ alkylene)-(3- to 7-membered heterocyclyl), —NH$_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl), and —NH(C=O)(3- to 7-membered heterocyclyl). In one embodiment, $R^{14}$, $R^{15}$, $R^{16}$, $R^{17}$, $R^{18}$ are each independently selected from H, halogen, —$NO_2$, —CN, $C_{1-6}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3 to 7-membered heterocyclyl), and —O(C=O)($C_{1-4}$ alkylene)-(3- to 7-membered heterocyclyl). In one embodiment, $R^{14}$, $R^{15}$, $R^{16}$, $R^{17}$, $R^{18}$ are each independently selected from H, halogen, —$NO_2$, —CN, $C_{1-6}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —O(C=O)($C_{1-6}$ alkyl), —O(C=O)($C_{3-6}$ cyclohydrocarbyl), —O(C=O)($C_{1-4}$ alkylene-$C_{3-6}$ cyclohydrocarbyl), —O(C=O)(3- to 7-membered heterocyclyl), and —O(C=O)($C_{1-4}$ alkylene)-(3- to 7-membered heterocyclyl). In one embodiment, $R^{14}$, $R^{15}$, $R^{16}$, $R^{17}$, $R^{18}$ are each independently selected from H, halogen, —$NO_2$, —CN, $C_{1-6}$ alkyl, —OH, —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl), and —NH(C=O)(3- to 7-membered heterocyclyl). In one embodiment, $R^{14}$, $R^{15}$, $R^{16}$, $R^{17}$, $R^{18}$ are each independently selected from H, halogen, —$NO_2$, —CN, $C_{1-6}$ alkyl, —OH, —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —NH(C=O)($C_{1-6}$ alkyl), —NH(C=O)($C_{3-6}$ cyclohydrocarbyl), —NH(C=O)($C_{1-4}$ alkylene-$C_{3-6}$ cyclohydrocarbyl) and —NH(C=O)(3- to 7-membered heterocyclyl). In one embodiment, $R^{14}$, $R^{15}$, $R^{16}$, $R^{17}$, $R^{18}$ are each independently selected from H, halogen, —$NO_2$, —CN, $C_{1-6}$ alkyl, —OH, —$NH_2$, —NH($C_{1-6}$ alkyl), —N($C_{1-6}$ alkyl)$_2$ and —NH(C=O)($C_{1-6}$ alkyl). In one embodiment, $R^{14}$, $R^{15}$, $R^{17}$, $R^{18}$ are each independently selected from H, halogen, —$NO_2$, —CN, $C_{1-6}$ alkyl, —OH, —$NH_2$, —NH($C_{1-6}$ alkyl), —N($C_{1-6}$ alkyl)$_2$ and —NH(C=O)($C_{1-6}$ alkyl). In one embodiment, $R^{16}$ is H. In one embodiment, $R^{16}$ is —$OCH_3$.

The structure described in the following formula (VIII) falls within the scope of the structure described in formula (I), formula (III) and formula (VII). In another aspect of the present invention, provided is a use of a compound of formula (VIII), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder

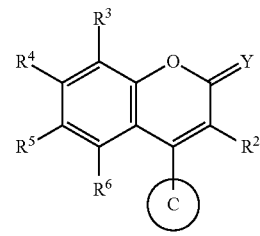

(VIII)

wherein ring C, Y, $R^2$, $R^3$, $R^4$, $R^5$, $R^6$ are as defined in formula (VII).

In one embodiment, ring C, Y, R2, R3, R4, R5, R6 in formula (VIII) are as defined in formula (VII);

provided that the compound of formula (VIII) does not include the following structure:

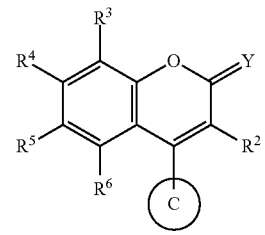

wherein $R^4$ is selected from —O($C_{1-6}$ alkyl) and —O($C_{1-4}$ alkylene-$C_{6-10}$ aryl).

In one embodiment, Y is O. When Y is O, formula (VIII) is

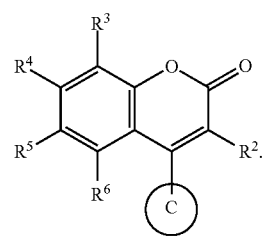

In a particular embodiment, the compound of formula (VIII) is selected from:

(compound 2)

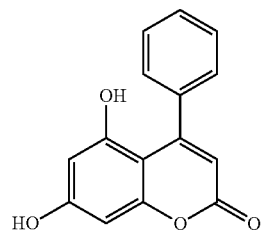

-continued (compound 6)

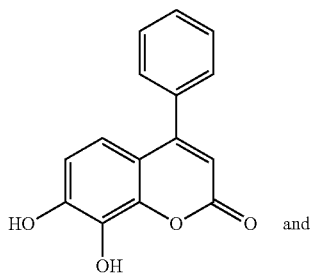 and (compound 7)

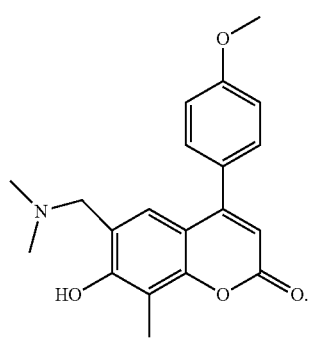

The structure described in the following formula (IX) falls within the scope of the structure described in formula (I), formula (III) and formula (VI). In another aspect of the present invention, there is provided use of a compound of formula (IX), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder,

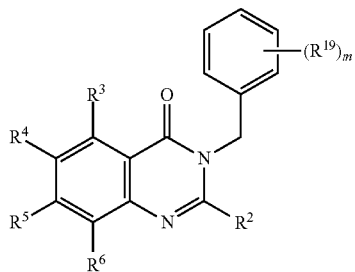

(IX)

wherein:
at each occurrence, $R^{19}$ is each independently selected from halogen, —$NO_2$, —CN, $C_{1-6}$ alkyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl is optionally substituted with one or more substituents selected from halogen, —$NO_2$, —CN, —OH, —O($C_{1-6}$ alkyl), —$NH_2$, —NH($C_{1-6}$ alkyl), —N($C_{1-6}$ alkyl)$_2$ and —COOH;
m is 0, 1, 2, 3, 4 or 5;
$R^2$, $R^3$, $R^4$, $R^5$, $R^6$ are as defined in formula (VI).
In one embodiment, $R^2$ is selected from H, halogen, —$NO_2$, —CN, $C_{1-6}$ alkyl, $C_{3-6}$ cyclohydrocarbyl, $C_{3-6}$ cyclohydrocarbyl-$C_{1-4}$ alkyl, 3- to 7-membered heterocyclyl, 3- to 7-, membered heterocyclyl-$C_{1-4}$ alkyl, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$ and —S(=O)$R^{a1}$, wherein the alkyl, cyclohydrocarbyl or heterocyclyl are optionally substituted with one or more substituents selected from halogen, —$NO_2$, —CN, $C_{1-6}$ alkyl, —$OR^{a2}$, $SR^{a2}$, —$NR^{a2}R^{b2}$, —C(=O)$OR^{a2}$, —C(=O)$NR^{a2}R^{b2}$ and —C(=O)$R^{a2}$. In a preferred embodiment, $R^2$ is selected from H, halogen, —$NO_2$, —CN, $C_{1-6}$ alkyl and —OH, wherein the alkyl is optionally substituted with one or more substituents selected from halogen, —$NO_2$, —CN, $C_{1-6}$ alkyl and —$NR^{a2}R^{b2}$. In a more preferred embodiment, $R^2$ is selected from H, halogen, $C_{1-6}$ alkyl and —OH, wherein the alkyl is optionally substituted with one or more substituents selected from halogen, $C_{1-6}$ alkyl and —$NR^{a2}R^{b2}$. In a further embodiment, $R^2$ is selected from H, $C_{1-4}$ alkyl and —OH, wherein the alkyl is optionally substituted with one or more substituents selected from —$NR^{a2}R^{b2}$. In a particular embodiment, $R^2$ is selected from H, $C_{1-4}$ alkyl and —OH, wherein the alkyl is —$CH_2[CH(CH_3)_2]$, and is optionally substituted with one or more substituents selected from —$NR^{a2}R^{b2}$. In another embodiment, $R^2$ is an alkyl substituted with —$NR^{a1}R^{b1}$. $R^{a1}$, $R^{b1}$, $R^{c1}$, $R^{a2}$, $R^{b2}$, $R^{c2}$ are as defined in formula (VI). In a particular embodiment, $R^2$ is

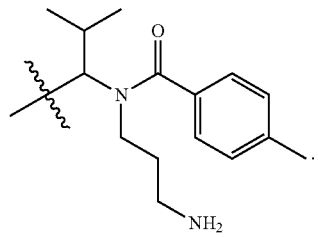

In one embodiment, at each occurrence, $R^{19}$ is each independently selected from halogen, $C_{1-6}$ alkyl, —OH, —O($C_{1-6}$ alkyl), —$NH_2$, —NH($C_{1-6}$ alkyl) and —N($C_{1-6}$ alkyl)$_2$, wherein the alkyl is optionally substituted with one or more substituents selected from halogen, —OH, —O($C_{1-6}$ alkyl), —$NH_2$, —NH($C_{1-6}$ alkyl) and —N($C_{1-6}$ alkyl)$_2$.

In a particular embodiment, the compound of formula (IX) is (compound 1)

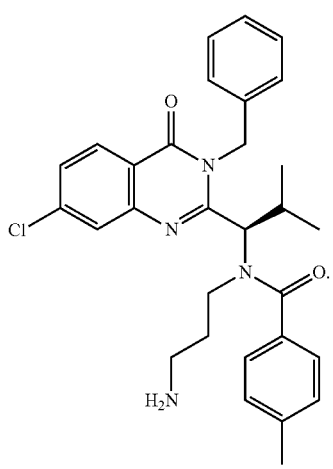

In another aspect of the present invention, provided is use of a compound of formula (I'), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder

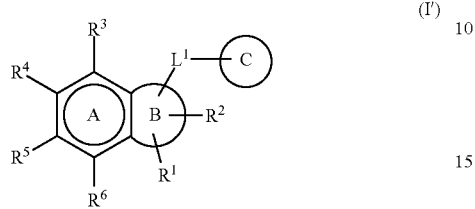

wherein:

ring A is a benzene ring;

ring B is a saturated or unsaturated 6-membered heterocycle, wherein the heterocycle contains 1, 2 or 3 heteroatoms each independently selected from N, O and S;

ring C is $C_{6-10}$ aryl, which is optionally substituted with one or more substituents each independently selected from $R^{X1}$;

$L^1$ is a bond, or is a $C_1$-$C_6$ hydrocarbon chain;

$R^1$ is =Y, wherein Y is O or S;

$R^2$ is selected from H, halogen, —$NO_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{14}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;

$R^3$, $R^4$, $R^5$, $R^6$ are each independently selected from H and $R^{X2}$;

at each occurrence, $R^{X1}$ and $R^{X2}$ are each independently selected from halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl, alkenyl or alkynyl are optionally substituted with one or more substituents selected from halogen, —$NO_2$, —CN, —OH, —SH, —$NH_2$, =O, —COOH and $C_{1-6}$ alkyl;

at each occurrence, $R^7$, $R^8$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, and 3- to 7-membered heterocyclyl-$C_{1-4}$ alkyl;

at each occurrence, $R^{a1}$, $R^{b1}$, $R^{c1}$, $R^{a2}$, $R^{b2}$, $R^{c2}$ each independently selected from H, $C_{1-6}$-alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$ and —S(=O)$R^{Y1}$, wherein the alkyl, alkenyl, alkynyl, cyclohydrocarbyl, heterocyclyl, aryl or heteroaryl are optionally substituted with one or more substituents selected from =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;

at each occurrence, $R^{Y1}$, $R^{Y2}$, $R^{Y3}$, $R^{Y4}$ are each independently selected from H, $C_{1-8}$ alkyl, —$C_{3-10}$ cyclohydrocarbyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, —OH, —SH, —$NH_2$, =O and —COOH.

In one embodiment, $R^1$ is =O. In another embodiment, $R^1$ is =S.

In one embodiment, ring B is a saturated or unsaturated 6-membered heterocycle, wherein the heterocycle contains 1 or 2 heteroatoms each independently selected from N and O. In another embodiment, ring B is dihydropyrimidine. In a preferred embodiment, ring B is selected from 1,6-dihydropyrimidine, 1,2-dihydropyrimidine and 1,4-dihydropyrimidine.

In a more preferred embodiment, A-B ring system is

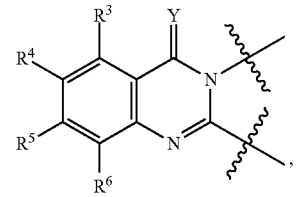

wherein Y is O or S. In a particularly preferred embodiment, A-B ring system is

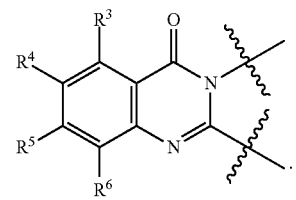

In yet another embodiment, ring B is 2H-pyran or 4H-pyran. In a preferred embodiment, A-B ring system is

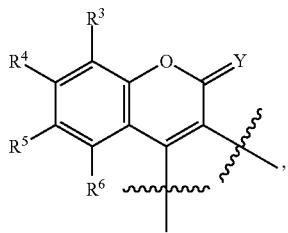

wherein Y is O or S. In a particularly preferred embodiment, A-B ring system is

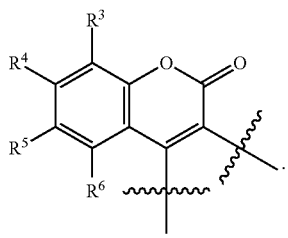

In yet another embodiment, ring C is phenyl, which is optionally substituted with 1, 2, 3, 4 or 5 substituents each independently selected from $R^{X1}$.

In one embodiment, $L^1$ is a bond. In another embodiment, $L^1$ is a $C_1$-$C_6$ hydrocarbon chain. In a preferred embodiment, $L^1$ is a $C_1$-$C_2$ hydrocarbon chain.

In yet another embodiment, $R^2$ is selected from H, halogen, —$NO_2$, —CN, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, =O, =S, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$ and —S(=O)$R^{a1}$, wherein the alkyl, alkenyl, alkynyl, cyclohydrocarbyl or heterocyclyl are optionally substituted with one or more substituents selected from halogen, —$NO_2$, —CN, $C_{1-6}$ alkyl, $C_{2-6}$ alkenyl, $C_{2-6}$ alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$ and —S(=O)$R^{a2}$. In a preferred embodiment, $R^2$ is selected from H, halogen, —$NO_2$, —CN, =O, =S, —COOH, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, —C(=O)($C_{1-6}$ alkyl), —COOH, —C(=O)O($C_{1-6}$ alkyl), —C(=O)O($C_{3-6}$ cyclohydrocarbyl), —C(=O)O($C_{1-4}$ alkylene-$C_{3-6}$ cyclohydrocarbyl), —C(=O)O(3- to 7-membered heterocyclyl), —C(=O)O($C_{1-4}$ alkylene)-(3- to 7-membered heterocyclyl), —C(=O)$NH_2$, —C(=O)NH($C_{1-6}$ alkyl), —C(=O)N($C_{1-6}$ alkyl)$_2$, —C(=O)NH($C_{1-4}$ alkylene-$C_{3-6}$ cyclohydrocarbyl), —C(=O)N($C_{1-4}$ alkylene-$C_{3-6}$ cyclohydrocarbyl)$_2$, —C(=O)NH(3- to 7-membered heterocyclyl), —C(=O)N(3- to 7-membered heterocyclyl)$_2$, —C(=O)NH($C_{1-4}$ alkylene-3- to 7-membered heterocyclyl), and —C(=O)N($C_{1-4}$ alkylene-3- to 7-membered heterocyclyl)$_2$, wherein the alkyl, alkylene, alkenyl, alkynyl, cyclohydrocarbyl or heterocyclyl are optionally substituted with one or more substituents selected from halogen, nitro, cyano, —OH, —SH, —$NH$, =O and —COOH. In another preferred embodiment, $R^2$ is selected from H, halogen, —$NO_2$, —CN and $C_{1-6}$ alkyl, wherein the alkyl is optionally substituted with one or more substituents selected from halogen, —$NO_2$, —CN, $C_{1-6}$ alkyl and —$NR^{a2}R^{b2}$. In a more preferred embodiment, $R^2$ is selected from H, halogen and $C_{1-6}$ alkyl, wherein the alkyl is optionally substituted with one or more substituents selected from halogen, $C_{1-6}$ alkyl and —$NR^{a2}R^{b2}$. In a further preferred embodiment, $R^2$ is H or $C_{1-4}$ alkyl, wherein the alkyl is optionally substituted with one or more substituents selected from —$NR^{a2}R^{b2}$. In a particularly preferred embodiment, $R^2$ is H or $C_{1-4}$ alkyl, wherein the alkyl is —CH[CH($CH_3$)$_2$]— and is optionally substituted with one or more substituents selected from —$NR^{a2}R^{b2}$.

In one embodiment, at each occurrence, $R^{X1}$ and $R^{X2}$ are each independently selected from halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl, alkenyl or alkynyl are optionally substituted with one or more substituents selected from halogen, —$NO_2$, —CN, —OH, —SH, —$NH_2$, =O, —COOH and $C_{1-6}$ alkyl. In a preferred embodiment, at each occurrence, $R^{X1}$ and $R^{X2}$ are each independently selected from halogen, —$NO_2$, —CN, $C_{1-6}$ alkyl, —$OR^7$, —$SR^7$, —$NR^7R^8$, —OC(=O)$R^7$, —NC(=O)$R^7R^8$, —OS(=O)$_2R^7$ and —NS(=O)$_2R^7R^8$. In a preferred embodiment, at each occurrence, $R^{X1}$ and $R^{X2}$ are each independently selected from halogen, $C_{1-6}$ alkyl, —$OR^7$ and —$NR^7R^8$. In a more preferred embodiment, at each occurrence, $R^{X1}$ and $R^{X2}$ are each independently selected from halogen, $C_{1-6}$ alkyl, —$OR^7$ and —$NR^7R^8$. In a further preferred embodiment, at each occurrence, $R^{X1}$ and $R^{X2}$ are each independently selected from halogen and —$OR^7$. In a more preferred embodiment, at each occurrence, $R^{X1}$ and $R^{X2}$ are each independently selected from Cl, Br, —OH and —O($C_{1-6}$ alkyl). In a particularly preferred embodiment, at each occurrence, $R^{X1}$ and $R^{X2}$ are each independently selected from Cl and —OH.

At each occurrence, $R^7$, $R^8$ are each independently selected from H, $C_{1-6}$ alkyl, $C_{2-6}$ alkenyl and $C_{2-6}$ alkynyl. In a preferred embodiment, at each occurrence, $R^7$, $R^8$ are each independently selected from H and $C_{1-6}$ alkyl. In a particularly preferred embodiment, at each occurrence, $R^7$, $R^8$ are each independently selected from H and $C_{1-6}$ alkyl.

In one embodiment, at each occurrence, $R^{a1}$, $R^{b1}$, $R^{c1}$, $R^{a2}$, $R^{b2}$, $R^{c2}$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, $OR^{Y1}$, $SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S (=O)₂NR^{Y1}R^{Y2} and —S(=O)R^{Y1}, wherein the alkyl, alkenyl, alkynyl, cyclohydrocarbyl, heterocyclyl, aryl or heteroaryl are optionally substituted with one or more substituents selected from =O, =S, —OR^{Y3}, —SR^{Y3}, —NR^{Y3}R^{Y4}, —C(=O)R^{Y3}, —C(=O)OR^{Y3} and —C(=O)NR^{Y3}R^{Y4}. In a preferred embodiment, at each occurrence, R^{a1}, R^{b1}, R^{c1}, R^{a2}, R^{b2}, R^{c2} are each independently selected from H, $C_{1-6}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, —OR^{Y1}, —SR^{Y1}, —NR^{Y1}R^{Y2}, —C(=O)OR^{Y1}, —C(=O)NR^{Y1}R^{Y2} and —C(=O)R^{Y1}, wherein the alkyl, aryl or heteroaryl are optionally substituted with one or more substituents selected from —R^{Y3} and —NR^{Y3}R^{Y4}. In another preferred embodiment, at each occurrence, R^{a1}, R^{b1}, R^{c1}, R^{a2}, R^{b2}, R^{c2} are each independently selected from H, $C_{1-6}$ alkyl, —OR^{Y1}, —NR^{Y1}R^{Y2}, —C(=O)OR^{Y1}, —C(=O)NR^{Y1}R^{Y2} and —C(=O)R^{Y1}, wherein the alkyl is optionally substituted with one or more substituents selected from —R^{Y3} and —NR^{Y3}R^{Y4}. In a more preferred embodiment, at each occurrence, R^{a1}, R^{b1}, R^{c1}, R^{a2}, R^{b2}, R^{c2} are each independently selected from H, $C_{1-6}$ alkyl, —OR^{Y1}, —NR^{Y1}R^{Y2} and —C(=O)R^{Y1}, wherein the alkyl is optionally substituted with one or more substituents selected from —NR^{Y3} and —NR^{Y3}R^{Y4}. In a further preferred embodiment, at each occurrence, R^{a1}, R^{b1}, R^{c1}, R^{a2}, R^{b2}, R^{c2} are each independently selected from H, $C_{1-6}$ alkyl, —OR^{Y1}, —NR^{Y1}R^{Y2} and —C(=O)R^{Y1}, wherein the alkyl is optionally substituted with one or more substituents selected from —NR^{Y3}R^{Y4}. In a particularly preferred embodiment, at each occurrence, R^{a1}, R^{b1}, R^{c1}, R^{a2}, R^{b2}, R^{c2} are each independently selected from H, $C_{1-3}$ alkyl, —OH and p-methylbenzoyl; wherein the alkyl is optionally substituted with one or more substituents selected from —NH₂.

In another embodiment, at each occurrence, R^{Y1}, R^{Y2}, R^{Y3}, R^{Y4} are each independently selected from H, $C_{1-8}$ alkyl, —$C_{3-10}$ cyclohydrocarbyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —NO₂, —CN, —OH, —SH, —NH₂, =O, —COOH and $C_{1-6}$ alkyl. In a preferred embodiment, at each occurrence, R^{Y1}, R^{Y2}, R^{Y3}, R^{Y4} are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, phenyl, phenyl-$C_{1-4}$ alkyl, 5- to 6-membered heteroaryl, and 5- to 6-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —NO₂, —CN, —OH, —SH, —NH₂, —COOH and $C_{1-6}$ alkyl. In a more preferred embodiment, at each occurrence, R^{Y1}, R^{Y2}, R^{Y3}, R^{Y4} are each independently selected from H, $C_{1-6}$ alkyl, phenyl, phenyl-$C_{1-4}$ alkyl, 5- to 6-membered heteroaryl, and 5- to 6-membered heteroaryl-$C_{1-4}$ alkyl, wherein the alkyl or phenyl is optionally substituted with one or more substituents selected from halogen, —NO₂, —CN, —OH, —SH, —NH₂, —COOH and $C_{1-6}$ alkyl. In a more preferred embodiment, at each occurrence, R^{Y1}, R^{Y2}, R^{Y3}, R^{Y4} are each independently selected from H, $C_{1-6}$ alkyl, phenyl and phenyl-$C_{1-4}$ alkyl, wherein the alkyl or phenyl is optionally substituted with one or more substituents selected from halogen and $C_{1-6}$ alkyl. In a particularly preferred embodiment, at each occurrence, R^{Y1}, R^{Y2}, R^{Y3}, R^{Y4} are each independently selected from H and p-methylphenyl.

In a particularly preferred embodiment, the compound of formula (I') is selected from:

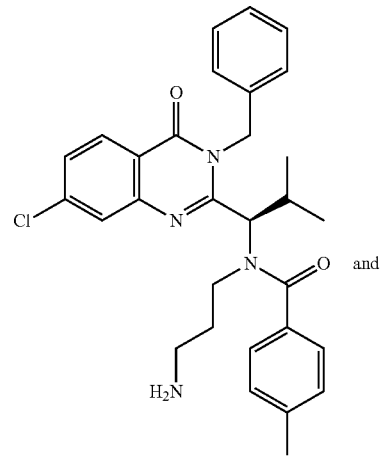

(compound 1)

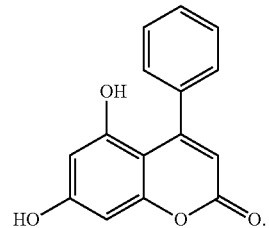

(compound 2)

In yet another aspect, the present invention provides use of pharmaceutical composition comprising a compound of any one of formula (I), formula (II), formula (III), formula (III'), formula (IV), formula (V), formula (VI), formula (VII), formula (VIII), formula (IX) and formula (I') in the preparation of a medicament for the prevention or treatment of a polyQ-related neurodegenerative disorder, wherein the pharmaceutical composition comprises a compound of any one of formula (I), formula (II), formula (III), formula (III'), formula (IV), formula (V), formula (VI), formula (VII), formula (VIII), formula (IX) and formula (I'), or a pharmaceutically acceptable salt, stereoisomer, solvate, polymorph, tautomer, isotopic compound, metabolite or prodrug thereof, and at least one pharmaceutically acceptable carrier.

In another aspect, the present invention provides a compound of any one of formula (I), formula (II), formula (III), formula (III'), formula (IV), formula (V), formula (VI), formula (VII), formula (VIII), formula (IX) and formula (I'), or a pharmaceutically acceptable salt, stereoisomer, solvate, polymorph, tautomer, isotopic compound, metabolite or prodrug thereof, or a pharmaceutical composition thereof, which is used to prevent or treat a polyQ-related neurodegenerative disorder.

In a further aspect, the present invention provides a method for preventing or treating a polyQ-related neurodegenerative disorder, which includes administering a compound of any one of formula (I), formula (II), formula (III), formula (III'), formula (IV), formula (V), formula (VI), formula (VII), formula (VIII), formula (IX) and formula (I'), or a pharmaceutically acceptable salt, stereoisomer, solvate, polymorph, tautomer, isotopic compound, metabolite or prodrug thereof, or a pharmaceutical composition thereof to an individual in need.

The compound of the present invention can be administered to patients orally or parenterally in the form of conventional preparations, for example, capsules, microcapsules, tablets, granules, powders, lozenges, pills, suppositories, injections, suspensions, syrups, patches, creams, lotions, ointments, gels, sprays, solutions, and emulsions. Suitable formulations can use conventional organic or inorganic additives and are prepared by commonly used methods. The organic or inorganic additives are, for example, excipients (for example, sucrose, starch, mannitol, sorbitol, lactose, glucose, cellulose, talc, calcium phosphate or calcium carbonate), binder (for example, cellulose, methylcellulose, hydroxymethylcellulose, polypropylpyrrolidone, polyvinylpyrrolidone, gelatin, gum acacia, polyethylene glycol, sucrose or starch), disintegrants (for example, starch, carboxymethylcellulose, hydroxypropyl starch, low-substituted hydroxypropylcellulose, sodium bicarbonate, calcium phosphate or calcium citrate), lubricants (for example, magnesium stearate, light anhydrous silicic acid, talc or sodium lauryl sulfate), flavoring agents (for example, citric acid, menthol, glycine or tangerine powder), preservatives (for example, sodium benzoate, sodium bisulfite, methyl paraben or propyl paraben), stabilizer (for example, citric acid, sodium citrate or acetic acid), suspending agents (for example, methylcellulose, polyvinylpyrrolidone or aluminum stearate), dispersant (for example, hydroxypropyl methylcellulose), diluent (for example, water) and base wax (for example, cocoa butter, white petrolatum or polyethylene glycol). For example, the effective amount of the compound in the pharmaceutical composition may be an amount that can achieve the desired effect.

Dosage regimens can be adjusted to provide the desired optimal response. For example, when the medicine is administered in the form of injection, it can be administered as a single bolus injection, bolus injection and/or continuous infusion, etc. For example, several divided doses may be administered over time, or the dose may be proportionally reduced or increased as indicated by the urgent need of the treatment situation. It should be noted that the dose value may vary with the type and severity of the condition to be alleviated and may include single or multiple doses. Generally, the dose of treatment varies, depending on the considerations, such as the age, gender, and general health of the patient to be treated; the frequency of treatment and the nature of the desired effect; the degree of tissue damage; the duration of symptoms; and other variables that can be adjusted by individual physicians. It should be further understood that for any particular individual, the specific dosing regimen should be adjusted over time according to the needs of the individual and the professional judgment of the person administering the composition or supervising the administration of the composition. The dosage and regimen of the pharmaceutical composition can be easily determined by a person of ordinary skill in the clinical field. For example, the composition or compound of the present invention may be administered in divided doses from 4 times a day to once every 3 days, and the dosage may be, for example, 0.01 to 1000 mg/time. The required dose can be administered one or more times to obtain the desired result. The pharmaceutical composition according to the present invention can also be provided in unit dosage forms.

In one embodiment, the present invention provides a capsule containing the compound of the present invention without an additional carrier.

The pharmaceutical composition of the present invention may be in the form of tablets, chewable tablets, capsules, solutions, parenteral solutions, lozenges, suppositories, and suspensions, etc. The composition can be formulated to contain a daily dose or an appropriate portion of the daily dose in a dosage unit, which can be a single tablet or capsule or a liquid of a suitable volume.

In one embodiment, the solution is prepared from a water-soluble salt, such as hydrochloride. Generally, all compositions are prepared according to known methods in pharmaceutical chemistry. Capsules can be prepared by mixing the compound with a suitable carrier or diluent and filling an appropriate amount of the mixture into the capsule. Commonly used carriers and diluents include, but are not limited to, inert powdered substances, such as a variety of different starches, powdered cellulose, especially crystalline and microcrystalline cellulose, sugars like fructose, mannitol and sucrose, cereal flour, and similar edible powder.

Tablets can be prepared by direct compression, wet granulation, or dry granulation. The preparation usually adds diluent, binder, lubricant and disintegrant and the compound. Typical diluents include, for example, various types of starch, lactose, mannitol, kaolin, calcium phosphate or sulfate, inorganic salts (such as sodium chloride) and powdered sugar. Powdered cellulose derivatives are also useful. Typical tablet binders are the following substances, such as starch, gelatin, and sugar (such as lactose, fructose, glucose, etc.). Natural and synthetic gums are also suitable, including gum acacia, alginate, methylcellulose, polyvinylpyrrolidone, etc. Polyethylene glycol, ethylcellulose and wax can also act as binders.

Lubricants can be selected from such slippery solids such as talc, magnesium stearate and calcium stearate, stearic acid and hydrogenated vegetable oils. A tablet disintegrant swells when wet to break the tablet and release the compound. They include starch, clay, cellulose, algin and gum. More specifically, for example, corn and potato starch, methylcellulose, agar, bentonite, lignocellulose, powdered natural sponge, anion exchange resin, alginic acid, guar gum, citrus pomace, carboxymethylcellulose and sodium lauryl sulfate can be used. Tablets can be coated with sugar as a flavoring and sealing agent or coated with a film-forming protective agent to optimize the dissolution performance of the tablet. The composition can also be formulated into chewable tablets, for example, by adding some substances to the formulation, such as mannitol.

When it is desired to be administered as a suppository, a typical base can be used. Cocoa butter is a traditional suppository base, which can be changed by adding wax to slightly increase its melting point. Especially water-miscible suppository bases including polyethylene glycols of various molecular weights are widely used.

The effect of the compound can be delayed or prolonged by a suitable formulation. For example, slowly dissolving pellets of the compound can be prepared and added to tablets or capsules or used as a sustained release implantable device. The technology also includes preparing several pellets with different dissolution rates and filling the capsule with a mixture of pellets. Tablets or capsules can be coated with a film that resists dissolution for a predictable period. Even parenteral preparations can be prepared as a long-acting formulation by dissolving or suspending the compound in an oily or emulsified vehicle that allows it to be slowly dispersed in the serum.

In a preferred embodiment, the polyQ-related neurodegenerative disorder is selected from spinocerebellar ataxia type 1, spinocerebellar ataxia type 2, spinocerebellar ataxia type 3, spinocerebellar ataxia type 7, spinocerebellar ataxia type 12, spinocerebellar ataxia type 17, dentatorubral-pallidoluysian atrophy, Huntington's disease and spinal-bulbar muscular atrophy. In another preferred embodiment, the polyQ-related neurodegenerative disorder is selected from the group consisting of spinocerebellar ataxia type 1, spinocerebellar ataxia type 2, spinocerebellar ataxia type 3, spinocerebellar ataxia type 7, spinocerebellar ataxia type 12 and spinocerebellar ataxia type 17. In another preferred embodiment, the polyQ-related neurodegenerative disorders are selected from Huntington's disease, spinocerebellar ataxia, type 1 and spinocerebellar ataxia type 3. In a particular embodiment, the polyQ-related neurodegenerative disorder is Huntington's disease. In another particular embodiment, the polyQ-related neurodegenerative disorder is spinocerebellar ataxia type 1 or spinocerebellar ataxia type 3.

The embodiments of the present invention can be listed as follows:

[1] Use of a compound of formula (I″), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder.

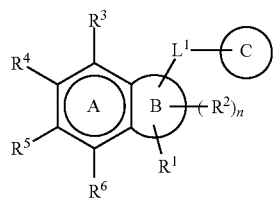

(I″)

wherein
ring A is a benzene ring;
ring B is a saturated or unsaturated 5-membered or 6-membered heterocycle, wherein the heterocycle contains 1, 2 or 3 heteroatoms each independently selected from N, O and S;
ring C is selected from $C_{6-10}$ aryl and 5- to 10-membered heteroaryl, wherein the aryl or heteroaryl are optionally substituted with one or more substituents each independently selected from $R^{X1}$;
$L^1$ is a bond, or is a $C_1$-$C_6$ hydrocarbon chain;
or, ring C is absent, and $L^1$ is absent;
$R^1$ is =Y, wherein Y is O or S, or is $OR^7$;
at each occurrence, $R^2$ is each independently selected from H, halogen, —$NO_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{14}$ alkyl, $C_{6-10}$ aryl-$C_{1-4}$ alkyl, 5- to 10-membered heteroaryl-$C_{1-4}$ alkyl, =O, =S, =$NR^{a1}$, —$OR^{a1}$, —$SR^{a1}$, —$NR^{a1}R^{b1}$, —C(=O)$OR^{a1}$, —C(=O)$NR^{a1}R^{b1}$, —C(=O)$R^{a1}$, —S(=O)$_2OR^{a1}$, —S(=O)$_2R^{a1}$, —S(=O)$_2NR^{a1}R^{b1}$, —S(=O)$R^{a1}$, —C(=S)$OR^{a1}$, —C(=S)$NR^{a1}R^{b1}$, —C(=S)$R^{a1}$, —P(=O)($OR^{a1}$)$OR^{b1}$, —C(=$NR^{a1}$)$NR^{b1}R^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, =O, =S, —$OR^{a2}$, —$SR^{a2}$, —$NR^{a2}R^{b2}$, —C(=O)$OR^{a2}$, —C(=O)$NR^{a2}R^{b2}$, —C(=O)$R^{a2}$, —S(=O)$_2OR^{a2}$, —S(=O)$_2R^{a2}$, —S(=O)$_2NR^{a2}R^{b2}$, —S(=O)$R^{a2}$ and —C(=$NR^{a2}$)$NR^{b2}R^{c2}$;

$R^3$, $R^4$, $R^5$, $R^6$ are each independently selected from H and $R^{X2}$;
at each occurrence, $R^{X1}$ and $R^{X2}$ are each independently selected from halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl, alkenyl or alkynyl are optionally substituted with one or more substituents selected from halogen, —$NO_2$, —CN, —OH, —O($C_{1-6}$ alkyl), —O($C_{3-6}$ cyclohydrocarbyl), —O($C_{1-4}$ alkylene-$C_{3-6}$ cyclohydrocarbyl), —O(3- to 7-membered heterocyclyl), —O($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —$NH_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), —N($C_{1-4}$ alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, =O, —COOH and $C_{1-6}$ alkyl;
at each occurrence, $R^7$, $R^8$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, and $C_{6-10}$ aryl-$C_{1-4}$ alkyl, wherein the alkyl, alkenyl, alkynyl, cyclohydrocarbyl, heterocyclyl or aryl are optionally substituted with one or more substituents selected from halogen, —$NO_2$, —CN, $C_{1-6}$ alkyl, —OH, —O($C_{1-6}$ alkyl), —$NH_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl);
at each occurrence, $R^{a1}$, $R^{b1}$, $R^{c1}$, $R^{a2}$, $R^{b2}$, $R^{c2}$ are each independently selected from H, $C_{1-6}$-alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, —$OR^{Y1}$, —$SR^{Y1}$, —$NR^{Y1}R^{Y2}$, —C(=O)$OR^{Y1}$, —C(=O)$NR^{Y1}R^{Y2}$, —C(=O)$R^{Y1}$, —S(=O)$_2OR^{Y1}$, —S(=O)$_2R^{Y1}$, —S(=O)$_2NR^{Y1}R^{Y2}$ and —S(=O)$R^{Y1}$, wherein the alkyl, alkenyl, alkynyl, cyclohydrocarbyl, heterocyclyl, aryl or heteroaryl are optionally substituted with one or more substituents selected from halogen, =O, =S, —$OR^{Y3}$, —$SR^{Y3}$, —$NR^{Y3}R^{Y4}$, —C(=O)$R^{Y3}$, —C(=O)$OR^{Y3}$ and —C(=O)$NR^{Y3}R^{Y4}$;
at each occurrence, $R^{Y1}$, $R^{Y2}$, $R^{Y3}$, $R^{Y4}$ are each independently selected from H, $C_{1-8}$ alkyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{14}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, —OH, —SH, —$NH_2$, =O and —COOH;

n is 1 or 2;
provided that the compound of formula (I″) does not include the following structure:

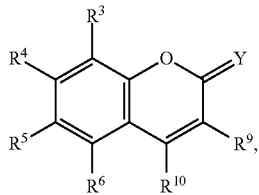

wherein R³ is selected from —O(C$_{1-6}$ alkyl) and —O(C$_{1-4}$ alkylene-C$_{6-10}$ aryl); R¹⁰ is H;
and the compound of formula (I″) does not include the following structure:

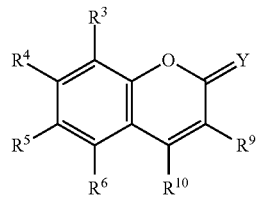

wherein R⁴ is —O(C$_{1-6}$ alkyl); R⁵ is halogen; R¹⁰ is CF$_3$;
and the compound of formula (I″) does not include the following structure:

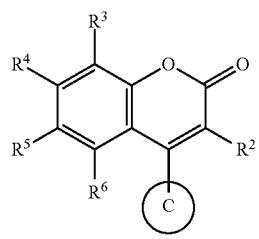

wherein R⁴ is selected from —O(C$_{1-6}$ alkyl) and —O(C$_{1-4}$ alkylene-C$_{6-10}$ aryl);
ring C is C$_{6-10}$ aryl, which is optionally substituted with one or more substituents each independently selected from R$^{X1}$;
and the compound of formula (I″) does not include the following structure:

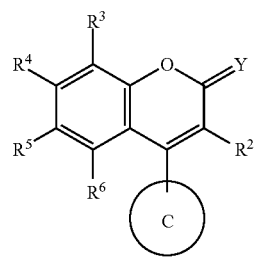

wherein R⁴ is selected from —OH and —O(C$_{1-6}$ alkyl); R⁵ is halogen; ring C is 5- to 10-membered heteroaryl, 5- to 10-membered heteroaryl which is optionally substituted with one or more substituents each independently selected from R$^{X1}$.

[2] Use of [1] above, wherein the compound of formula (I″) has the following structure of formula (II″):

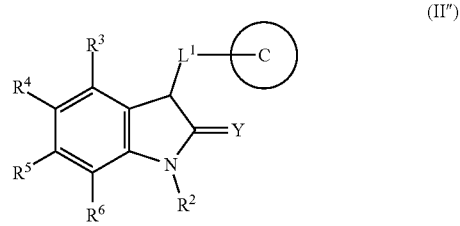

(II″)

wherein
Y is O or S;
ring C is 5- to 7-membered heteroaryl, wherein the 5- to 7-membered heteroaryl is optionally substituted with one or more substituents each independently selected from R$^{X1}$;
R² is selected from H and C$_{1-8}$ alkyl;
L¹ is a bond, or is a C$_1$-C$_6$ hydrocarbon chain;
R³, R⁴, R⁵, R⁶ are each independently selected from H and R$^{X2}$;
wherein R$^{X1}$, R$^{X2}$ are as defined in [1] above.

[3] Use of [1] above, wherein the compound of formula (I″) has the following structure of formula (IV″):

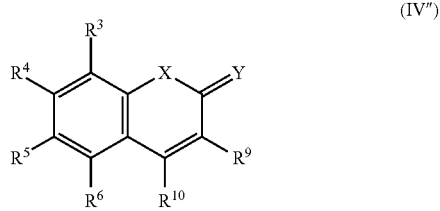

(IV″)

wherein
Y is O or S;
X is O;
R⁹ is selected from H, halogen, C$_{1-6}$ alkyl, C$_{3-6}$ cyclohydrocarbyl, C$_{3-6}$ cyclohydrocarbyl-C$_{1-4}$ alkyl, 3- to 7-membered heterocyclyl, 3- to 7-membered heterocyclyl-C$_{1-4}$ alkyl, —OR$^{a1}$, —SR$^{a1}$, —NR$^{a1}$R$^{b1}$, —C(=O)OR$^{a1}$, —C(=O)NR$^{a1}$R$^{b1}$, —C(=O)R$^{a1}$, —S(=O)$_2$OR$^{a1}$, —S(=O)$_2$R$^{a1}$, —S(=O)$_2$NR$^{a1}$R$^{b1}$ and —S(=O)R$^{a1}$, wherein the alkyl, cyclohydrocarbyl or heterocyclyl are optionally substituted with one or more substituents selected from halogen, —NO$_2$, —CN, C$_{1-6}$ alkyl, —OR$^{a2}$, —SR$^{a2}$, —NR$^{a2}$R$^{b2}$, —C(=O)OR$^{a2}$, —C(=O)NR$^{a2}$R$^{b2}$, —C(=O)R$^{a2}$, —S(=O)$_2$OR$^{a2}$, —S(=O)$_2$R$^{a2}$, —S(=O)$_2$NR$^{a2}$R$^{b2}$ and —S(=O)R$^{a2}$; wherein R$^{a1}$, R$^{b1}$, R$^{a2}$, R$^{b2}$ are as defined in [1] above;
R¹⁰ is selected from H, halogen, C$_{1-6}$ alkyl, C$_{3-6}$ cyclohydrocarbyl, C$_{3-6}$ cyclohydrocarbyl-C$_{1-4}$ alkyl, 3- to 7-membered heterocyclyl, and 3- to 7-membered heterocyclyl-C$_{1-4}$ alkyl;
R³ is selected from H, halogen, C$_{1-6}$ alkyl, —OH, —NH$_2$, —NH(C$_{1-6}$ alkyl) and —N(C$_{1-6}$ alkyl)$_2$, wherein the alkyl is optionally substituted with one or more substituents selected from halogen, —OH, —O($C_{1-6}$ alkyl), —NH$_2$, —NH($C_{1-6}$ alkyl) and —N($C_{1-6}$ alkyl)$_2$;

$R^4$ is selected from H, halogen, —NO$_2$, —CN, $C_{1-6}$ alkyl, —OR$^7$, —SR$^7$ and —NR$^7$R$^8$; at each occurrence, R$^7$, R$^8$ are each independently selected from H and $C_{1-6}$ alkyl, wherein the alkyl is optionally substituted with one or more substituents selected from halogen, —NO$_2$, —CN, —OH, —O($C_{1-6}$ alkyl), —NH$_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl); wherein R$^7$, R$^8$ are as defined in [1] above;

$R^5$ is selected from H, halogen, —NO$_2$, —CN, $C_{1-6}$ alkyl, —OH, —O($C_{1-6}$ alkyl), —NH$_2$, —NH($C_{1-6}$-alkyl), —N($C_{1-6}$ alkyl)$_2$, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl), wherein the alkyl is optionally substituted with one or more substituents selected from halogen, —OH, —O($C_{1-6}$ alkyl), —NH$_2$, —NH($C_{1-6}$ alkyl), —N($C_{1-6}$ alkyl)$_2$, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl);

$R^6$ is selected from H, halogen, —NO$_2$, —CN, $C_{1-6}$ alkyl, —OH, —O($C_{1-6}$ alkyl), —O(benzyl), —SH, —S($C_{1-6}$ alkyl), —S(benzyl), —NH$_2$, —NH($C_{1-6}$ alkyl), —N($C_{1-6}$ alkyl)$_2$ and —NH(benzyl), wherein the alkyl or benzyl is optionally substituted with one or more substituents selected from halogen, —OH, —O($C_{1-6}$ alkyl), —NH$_2$, —NH($C_{1-6}$ alkyl) and —N($C_{1-6}$ alkyl)$_2$;

provided that when $R^4$ is —O($C_{1-6}$ alkyl) and $R^5$ is halogen, $R^{10}$ is not CF$_3$.

[4] Use of [1] above, wherein the compound of formula (I") has the following structure of formula (VI"):

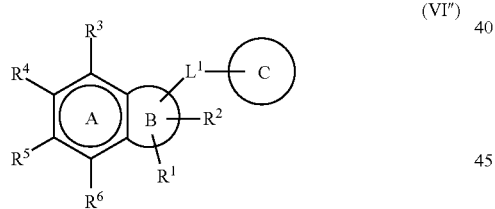

(VI")

wherein:

ring B is a saturated or unsaturated 6-membered heterocycle, wherein the heterocycle contains 1, 2 or 3 heteroatoms each independently selected from N, O and S;

ring C is $C_{6-10}$ aryl, which is substituted with one or more substituents each independently selected from $R^{X1}$;

$L^1$ is a bond, or is a $C_1$-$C_6$ hydrocarbon chain;

$R^2$ is selected from H, halogen, —NO$_2$, —CN, $C_{1-8}$ alkyl, $C_{2-8}$ alkenyl, $C_{2-8}$ alkynyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl-$C_{1-4}$ alkyl, 5- to 10-membered heteroaryl-$C_{1-4}$ alkyl, =O, =S, =NR$^{a1}$, —OR$^{a1}$, —SR$^{a1}$, —NR$^{a1}$R$^{b1}$, —C(=O)OR$^{a1}$, —C(=O)NR$^{a1}$R$^{b1}$, —C(=O)R$^{a1}$, —S(=O)$_2$OR$^{a1}$, —S(=O)$_2$R$^{a1}$, —S(=O)$_2$NR$^{a1}$R$^{b1}$, —S(=O)R$^{a1}$, —C(=S)OR$^{a1}$, —C(=S)NR$^{a1}$R$^{b1}$, —C(=S)R$^{a1}$, —P(=O)(OR$^{a1}$)OR$^{b1}$, —C(=NR$^{a2}$)NR$^{b1}$R$^{c1}$, —OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —NO$_2$, —CN, $C_{1-8}$ alkyl, $C_{2-8}$ alkenyl, $C_{2-8}$ alkynyl, =O, =S, —OR$^{a2}$, —SR$^{a2}$, —NR$^{a2}$R$^{b2}$, —C(=O)OR$^{a2}$, —C(=O)NR$^{a2}$R$^{b2}$, —C(=O)R$^{a2}$, —S(=O)$_2$OR$^{a2}$, —S(=O)$_2$R$^{a2}$, —S(=O)$_2$NR$^{a2}$R$^{b2}$, —S(=O)R$^{a2}$ and —C(=NR$^{a2}$)NR$^{b2}$R$^{c2}$;

$R^3$, $R^4$, $R^5$, $R^6$ are each independently selected from H and $R^{X2}$;

at each occurrence, $R^{X1}$ and $R^{X2}$ are each independently selected from halogen, —NO$_2$, —CN, $C_{1-6}$ alkyl, $C_{2-6}$ alkenyl, $C_{2-6}$ alkynyl, —NR$^7$R$^8$, —C(=O)OR$^7$, —C(=O)NR$^7$R$^8$, —OC(=O)R$^7$, —NC(=O)R$^7$R$^8$, —C(=O)R$^7$, —S(=O)$_2$OR$^7$, —S(=O)$_2$R$^7$, —S(=O)$_2$NR$^7$R$^8$, —OS(=O)$_2$R$^7$, —NS(=O)$_2$R$^7$R$^8$ and —S(=O)R$^7$, wherein the alkyl, alkenyl or alkynyl are optionally substituted with one or more substituents selected from halogen, —NO$_2$, —CN, —OH, —O($C_{1-6}$ alkyl), —O($C_{3-6}$ cyclohydrocarbyl), alkylene-$C_{3-6}$ cyclohydrocarbyl), —O(3- to 7-membered heterocyclyl), —O($C_{1-4}$ alkylene)-(3- to 7-membered heterocyclyl), —SH, —S($C_{1-6}$ alkyl), —S($C_{3-6}$ cyclohydrocarbyl), —S($C_{1-4}$ alkylene-$C_{3-6}$ cyclohydrocarbyl), —S(3- to 7-membered heterocyclyl), —S($C_{1-4}$ alkylene)-(3- to 7-membered heterocyclyl), —NH$_2$, —NH($C_{1-6}$ alkyl), —N($C_{1-6}$ alkyl)$_2$, —NH($C_{3-6}$ cyclohydrocarbyl), —N($C_{3-6}$ cyclohydrocarbyl)$_2$, —NH($C_{1-4}$ alkylene-$C_{3-6}$ cyclohydrocarbyl), alkylene-$C_{3-6}$ cyclohydrocarbyl)$_2$, —NH(3- to 7-membered heterocyclyl), —N(3- to 7-membered heterocyclyl)$_2$, —NH($C_{1-4}$ alkylene-3- to 7-membered heterocyclyl), —N($C_{1-4}$ alkylene-3- to 7-membered heterocyclyl)$_2$, =O, —COOH and $C_{1-6}$ alkyl;

at each occurrence, R$^7$, R$^8$ are each independently selected from H, $C_{1-6}$ alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, and 3- to 7-membered heterocyclyl-$C_{1-4}$ alkyl, wherein the alkyl, alkenyl, alkynyl, cyclohydrocarbyl or heterocyclyl are optionally substituted with one or more substituents selected from halogen, —NO$_2$, —CN, $C_{1-6}$ alkyl, —OH, —O($C_{1-6}$ alkyl), —NH$_2$, —NH($C_{1-6}$ alkyl), —N($C_{1-6}$ alkyl)$_2$, —COOH, —C(=O)O($C_{1-6}$ alkyl), —C(=O)NH($C_{1-6}$ alkyl), —C(=O)N($C_{1-6}$ alkyl)$_2$, —OC(=O)($C_{1-6}$ alkyl), —NHC(=O)($C_{1-6}$ alkyl) and —C(=O)($C_{1-6}$ alkyl);

at each occurrence, R$^{a1}$, R$^{b1}$, R$^{c1}$, R$^{a2}$, R$^{b2}$, R$^{c2}$ are each independently selected from H, $C_{1-6}$-alkyl, $C_{2-6}$ alkenyl, $C_{2-6}$ alkynyl, $C_{3-6}$ cyclohydrocarbyl, $C_{3-6}$ cyclohydrocarbyl-$C_{1-4}$ alkyl, 3- to 7-membered heterocyclyl, 3- to 7-membered heterocyclyl-$C_{1-4}$ alkyl, $C_{6-10}$ aryl, $C_{6-10}$ aryl-$C_{1-4}$ alkyl, 5- to 10-membered heteroaryl, 5- to 10-membered heteroaryl-$C_{1-4}$ alkyl, —OR$^{Y1}$, —SR$^{Y1}$, —NR$^{Y1}$R$^{Y2}$, —C(=O)OR$^{Y1}$, —C(=O)NR$^{Y1}$R$^{Y2}$, —C(=O)R$^{Y1}$, —S(=O)$_2$OR$^{Y1}$, —S(=O)$_2$R$^{Y1}$, —S(=O)$_2$NR$^{Y1}$R$^{Y2}$ and —S(=O)R$^{Y1}$, wherein the alkyl, alkenyl, alkynyl, cyclohydrocarbyl, heterocyclyl, aryl or heteroaryl are optionally substituted with one or more substituents selected from halogen, =O, =S, —OR$^{Y3}$, —SR$^{Y3}$, —NR$^{Y3}$R$^{Y4}$, —C(=O)R$^{Y3}$, —C(=O)OR$^{Y3}$ and —C(=O)NR$^{Y3}$R$^{Y4}$;

at each occurrence, R$^{Y1}$, R$^{Y2}$, R$^{Y3}$, R$^{Y4}$ are each independently selected from H, $C_{1-8}$ alkyl, $C_{3-10}$ cyclohydrocarbyl, $C_{3-10}$ cyclohydrocarbyl-$C_{1-4}$ alkyl, 3- to 10-membered heterocyclyl, 3- to 10-membered heterocyclyl-$C_{1-4}$ alkyl, $C_{6-10}$ aryl, $C_{6-10}$ aryl-$C_{1-4}$ alkyl, 5- to 10-membered heteroaryl, and 5- to 10-membered heteroaryl-$C_{1-4}$ alkyl, wherein the alkyl, alkenyl, alkynyl, cyclohydrocarbyl, heterocyclyl, aryl or heteroaryl are optionally substituted with one or more substituents selected from halogen, —$NO_2$, —CN, $C_{1-8}$ alkyl, $C_{2-8}$ alkenyl, $C_{2-8}$ alkynyl, —OH, —SH, —$NH_2$, =O and —COOH;

ring A, $R^1$ is as defined in [1] above;

provided that the compound of formula (VI″) does not include the following structure:

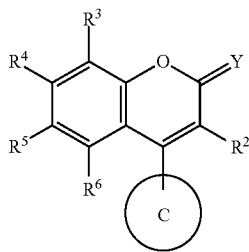

wherein $R^4$ is selected from —O($C_{1-6}$ alkyl) and —O($C_{1-4}$ alkylene-$C_{6-10}$ aryl).

[5] Use of [1] above, wherein ring B is dihydropyrimidine.

[6] Use of [1] above, wherein ring B is 2H-pyran or 4H-pyran; preferably is 2H-pyran.

[7] Use of any of [1]-[6] above, wherein $R^1$ is =O.

[8] Use of [5] above, wherein A-B ring system is

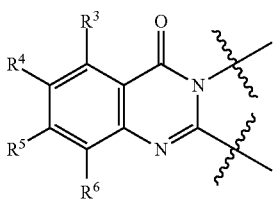

[9] Use of [6] above, wherein A-B ring system is

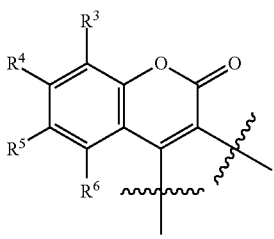

[10] Use of any of [4]-[9] above, wherein $L^1$ is a bond, or is a $C_1$-$C_2$ hydrocarbon chain.

[11] Use of any of [4]-[10] above, wherein ring C is phenyl, wherein the phenyl is optionally substituted with 1, 2, 3, 4 or 5 substituents each independently selected from $R^{X1}$; preferably ring C is

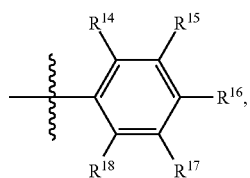

wherein $R^{14}$, $R^{15}$, $R^{16}$, $R^{17}$, $R^{18}$ are each independently selected from H, halogen, —$NO_2$, —CN, $C_{1-6}$ alkyl, $C_{2-6}$ alkenyl, $C_{2-6}$ alkynyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$;

preferably, $R^{14}$, $R^{15}$, $R^{16}$, $R^{17}$, $R^{18}$ are each independently selected from H, halogen, —$NO_2$, —CN, $C_{1-6}$ alkyl, —$OR^7$, —$NR^7R^8$, —C(=O)$OR^7$, —C(=O)$NR^7R^8$, —OC(=O)$R^7$, —NC(=O)$R^7R^8$ and —C(=O)$R^7$;

more preferably, $R^{14}$, $R^{15}$, $R^{17}$, $R^{18}$ are each independently selected from H, halogen, —$NO_2$, —CN, $C_{1-6}$ alkyl, —OH, —$NH_2$, —NH($C_{1-6}$ alkyl), —N($C_{1-6}$ alkyl)$_2$ and —NH(C=O)($C_{1-6}$ alkyl); $R^{16}$ is H or —$OCH_3$.

[12] Use of [4] above, wherein the compound of formula (VI″) has the structure of the following formula (IX″):

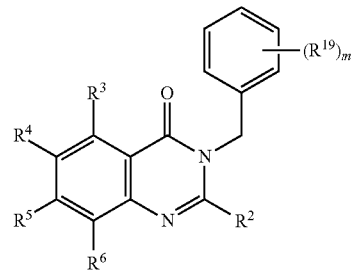

wherein:

at each occurrence, $R^{19}$ are each independently selected from halogen, —$NO_2$, —CN, $C_{1-6}$ alkyl, —$OR^7$, —$SR^7$, —$NR^7R^8$, —C(=O)$OR^7$, —C(=O)$NR^7R^8$, —OC(=O)$R^7$, —NC(=O)$R^7R^8$, —C(=O)$R^7$, —S(=O)$_2OR^7$, —S(=O)$_2R^7$, —S(=O)$_2NR^7R^8$, —OS(=O)$_2R^7$, —NS(=O)$_2R^7R^8$ and —S(=O)$R^7$, wherein the alkyl is optionally substituted with one or more substituents selected from halogen, —$NO_2$, —CN, —OH, —O($C_{1-6}$ alkyl), —$NH_2$, —NH($C_{1-6}$ alkyl), —N($C_{1-6}$ alkyl)$_2$ and —COOH;

m is 0, 1, 2, 3, 4 or 5;

$R^2$, $R^3$, $R^4$, $R^5$, $R^6$ are as defined in [4] above.

[13] Use of any of [1]-[12] above, wherein the compounds are selected from

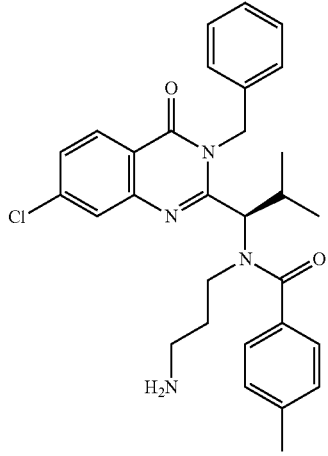
(compound 3)

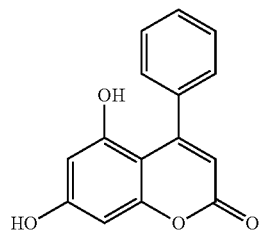
(compound 4)

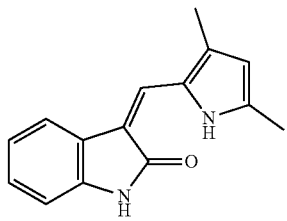
(compound 6)

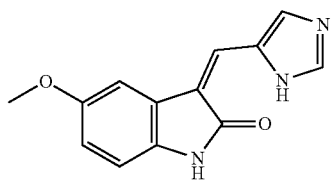

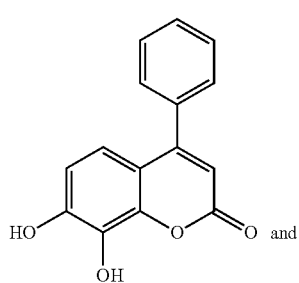
and

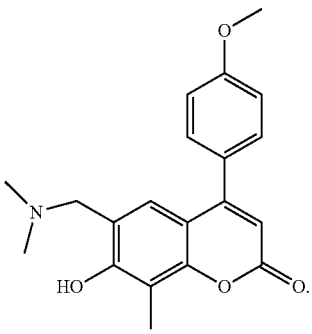
(compound 7)

[14] Use of a pharmaceutical composition in the preparation of a medicament for preventing or treating a polyQ-related neurodegenerative disorders; wherein the pharmaceutical composition comprises a compound of formula (I″), formula (II″), formula (III″), formula (III″), formula (IV″), formula (V″), formula (VI″), formula (VII″), formula (VIII″), formula (IX″), formula (X″) or formula (XI″) in any one of [1]-[13] above, or a pharmaceutically acceptable salt, stereoisomer, solvate, polymorph, tautomer, isotopic compound, metabolite or prodrug thereof, and at least one pharmaceutically acceptable carrier.

[15] Use of any of [1]-[14] above, wherein the polyQ-related neurodegenerative disorder is selected from the group consisting of spinocerebellar ataxia type 1, spinocerebellar ataxia type 2, spinocerebellar ataxia type 3, spinocerebellar ataxia type 7, spinocerebellar ataxia type 12, spinocerebellar ataxia type 17, dentatorubral-pallidoluysian atrophy, Huntington's disease, and spinal-bulbar muscular atrophy, especially Huntington's disease and spinocerebellar ataxia type 3.

The embodiments of the present invention can also be listed as follows:

<1> Use of a compound of formula (I'), or a pharmaceutically acceptable salt, stereoisomer, solvate, polymorph, tautomer, isotopic compound, metabolite or prodrug thereof in the preparation of a medicament for preventing or treating a polyQ-related neurodegenerative disorder

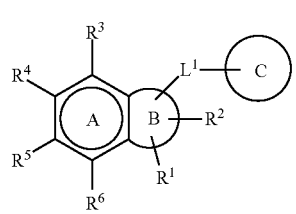
(I')

wherein:
ring A is a benzene ring;
ring B is a saturated or unsaturated 6-membered heterocycle, wherein the heterocycle contains 1, 2 or 3 heteroatoms each independently selected from N, O and S;
ring C is $C_{6-10}$ aryl, which is optionally substituted with one or more substituents each independently selected from $R^{X1}$;
$L^1$ is a bond, or is a $C_1$-$C_6$ hydrocarbon chain;
$R^1$ is =Y, wherein Y is O or S;

R² is selected from H, halogen, —NO₂, —CN, C₁₋₈ alkyl, C₂₋₈ alkenyl, C₂₋₈ alkynyl, C₃₋₁₀ cyclohydrocarbyl, C₃₋₁₀ cyclohydrocarbyl-C₁₋₄ alkyl, 3- to 10-membered heterocyclyl, 3- to 10-membered heterocyclyl-C₁₄ alkyl, C₆₋₁₀ aryl, C₆₋₁₀ aryl-C₁₋₄ alkyl, 5- to 10-membered heteroaryl, 5- to 10-membered heteroaryl-C₁₋₄ alkyl, =O, =S, =NR$^{a1}$, —OR$^{a1}$, —SR$^{a1}$, —NR$^{a1}$R$^{b1}$, —C(=O)OR$^{a1}$, —C(=O)NR$^{a1}$R$^{b1}$, C(=O)R$^{a1}$, —S(=O)₂OR$^{a1}$, —S(=O)₂R$^{a1}$, —S(=O)₂NR$^{a1}$R$^{b1}$, —S(=O)R$^{a1}$, —C(=S)OR$^{a1}$, —C(=S)NR$^{a1}$R$^{b1}$, —C(=S)R$^{a1}$, —P(=O)(OR$^{a1}$)OR$^{b1}$, —C(=NR$^{a1}$)NR$^{b1}$R$^{c1}$, OCN, —SCN, —N=C=O and —NCS, wherein the alkyl, alkenyl, alkynyl, cyclohydrocarbyl, heterocyclyl, aryl or heteroaryl are optionally substituted with one or more substituents selected from halogen, —NO₂, —CN, C₁₋₈ alkyl, C₂₋₈ alkenyl, C₂₋₈ alkynyl, =O, =S, —OR$^{a2}$, —SR$^{a2}$, —NR$^{a2}$R$^{b2}$, —C(=O)OR$^{a2}$, —C(=O)NR$^{a2}$R$^{b2}$, —C(=O)R$^{a2}$, —S(=O)₂OR$^{a2}$, —S(=O)₂R$^{a2}$, —S(=O)₂NR$^{a2}$R$^{b2}$, —S(=O)R$^{a2}$ and —C(=NR$^{a2}$)NR$^{b2}$R$^{c2}$;

R³, R⁴, R⁵, R⁶ are each independently selected from H and R$^{X2}$;

at each occurrence, R$^{X1}$ and R$^{X2}$ are each independently selected from halogen, —NO₂, —CN, C₁₋₆ alkyl, C₂₋₆ alkenyl, C₂₋₆ alkynyl, —OR⁷, —NR⁷R⁸, —C(=O)OR⁷, —C(=O)NR⁷R⁸, —OC(=O)R⁷, —NC(=O)R⁷R⁸, —C(=O)R⁷, —S(=O)₂OR⁷, —S(=O)₂R⁷, —S(=O)₂NR⁷R⁸, —OS(=O)₂R⁷, —NS(=O)₂R⁷R⁸ and —S(=O)R⁷, wherein the alkyl, alkenyl or alkynyl are optionally substituted with one or more substituents selected from halogen, —NO₂, —CN, —OH, —SH, —NH₂, =O, —COOH and C₁₋₆ alkyl;

at each occurrence, R⁷, R⁸ are each independently selected from H, C₁₋₆ alkyl, C₂₋₆ alkenyl, C₂₋₆ alkynyl, C₃₋₆ cyclohydrocarbyl, C₃₋₆ cyclohydrocarbyl-C₁₋₄ alkyl, 3- to 7-membered heterocyclyl, and 3- to 7-membered heterocyclyl-C₁₋₄ alkyl;

at each occurrence, R$^{a1}$, R$^{b1}$, R$^{c1}$, R$^{a2}$, R$^{b2}$, R$^{c2}$ are each independently selected from H, C₁₋₆-alkyl, C₂₋₆ alkenyl, C₂₋₆ alkynyl, C₃₋₆ cyclohydrocarbyl, C₃₋₆ cyclohydrocarbyl-C₁₋₄ alkyl, 3- to 7-membered heterocyclyl, 3- to 7-membered heterocyclyl-C₁₋₄ alkyl, C₆₋₁₀ aryl, C₆₋₁₀ aryl-C₁₋₄ alkyl, 5- to 10-membered heteroaryl, 5- to 10-membered heteroaryl-C₁₋₄ alkyl, —OR$^{y1}$, —SR$^{y1}$, —NR$^{y1}$R$^{y2}$, —C(=O)OR$^{y1}$, —C(=O)NR$^{y1}$R$^{y2}$, —C(=O)R$^{y1}$, —S(=O)₂OR$^{y1}$, —S(=O)₂R$^{y1}$, —S(=O)₂NR$^{y1}$R$^{y2}$ and —S(=O)R$^{y1}$, wherein the alkyl, alkenyl, alkynyl, cyclohydrocarbyl, heterocyclyl, aryl or heteroaryl are optionally substituted with one or more substituents selected from =O, =S, —OR$^{y3}$, —SR$^{y3}$, —NR$^{y3}$R$^{y4}$, —C(=O)R$^{y3}$, —C(=O)OR$^{y3}$ and —C(=O)NR$^{y3}$R$^{y4}$;

at each occurrence, R$^{y1}$, R$^{y2}$, R$^{y3}$, R$^{y4}$ are each independently selected from H, C₁₋₈ alkyl, —C₃₋₁₀ cyclohydrocarbyl, C₃₋₁₀ cyclohydrocarbyl, C₃₋₁₀ cyclohydrocarbyl-C₁₋₄ alkyl, 3- to 10-membered heterocyclyl, 3- to 10-membered heterocyclyl-C₁₋₄ alkyl, C₆₋₁₀ aryl, C₆₋₁₀ aryl-C₁₋₄ alkyl, 5- to 10-membered heteroaryl, and 5- to 10-membered heteroaryl-C₁₋₄ alkyl, wherein the alkyl, alkenyl, alkynyl, cyclohydrocarbyl, heterocyclyl, aryl or heteroaryl are optionally substituted with one or more substituents selected from halogen, —NO₂, —CN, C₁₋₈ alkyl, C₂₋₈ alkenyl, C₂₋₈ alkynyl, —OH, —SH, —NH₂, =O and —COOH.

<2> Use of <1> above, wherein ring B is saturated or unsaturated 6-membered heterocycle; wherein the heterocycle contains one or two heteroatoms each independently selected from N and O.

<3> Use of <1> or <2> above, wherein ring B is dihydropyrimidine.

<4> Use of <1> or <2> above, wherein ring B is 2H-pyran or 4H-pyran; preferably is 2H-pyran.

<5> Use of any one of <1> to <4> above, wherein R¹ is =O.

<6> Use of <3> above, wherein A-B ring system is

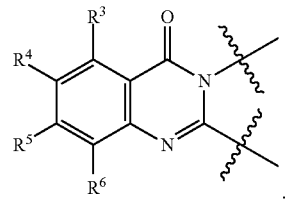

<7> Use of <4> above, wherein A-B ring system is

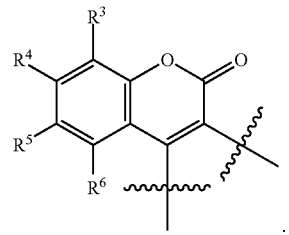

<8> Use of any one of <1> to <7> above, wherein L¹ is a bond, or is a C₁-C₂ hydrocarbon chain.

<9> Use of any one of <1> to <8> above, wherein R² is selected from H, halogen, —NO₂, —CN and C₁₋₆ alkyl, wherein the alkyl is optionally substituted with one or more substituents selected from halogen, —NO₂, —CN, C₁₋₆ alkyl and —NR$^{a2}$R$^{b2}$; preferably, R² is selected from H, halogen and C₁₋₆ alkyl, wherein the alkyl is optionally substituted with one or more substituents selected from halogen, C₁₋₆ alkyl and —NR$^{a2}$R$^{b2}$, more preferably, R² is H or C₁₋₄ alkyl, wherein the alkyl is optionally substituted with one or more substituents selected from —NR$^{a2}$R$^{b2}$, especially preferably, R² is H or C₁₋₄ alkyl, wherein the alkyl is —CH[CH(CH₃)₂]—, and is optionally substituted with one or more substituents selected from —NR$^{a2}$R$^{b2}$.

<10> Use of <9> above, wherein R² is H.

<11> Use of any one of <1> to <10> above, wherein at each occurrence, R$^{X1}$ and R$^{X2}$ are each independently selected from halogen, C₁₋₆ alkyl, —OR⁷ and —NR⁷R⁸; preferably, at each occurrence, R$^{X1}$ and R$^{X2}$ are each independently selected from halogen, C₁₋₆ alkyl, —OW and —NR⁷R⁸; more preferably, at each occurrence, R$^{X1}$ and R$^{X2}$ are each independently selected from halogen and —OW; further preferably, at each occurrence, R$^{X1}$ and R$^{X2}$ are each independently selected from C₁, Br, —OH and —O(C₁₋₆ alkyl); especially preferably, at each occurrence, R$^{X1}$ and R$^{X2}$ are each independently selected from C₁ and —OH; wherein at each occurrence, R⁷, R⁸ are each independently selected from H and C₁₋₆ alkyl.

<12> Use of any one of <1> to <11> above, wherein at each occurrence, R$^{a1}$, R$^{b1}$, R$^{c1}$, R$^{a2}$, R$^{b2}$, R$^{c2}$ are each independently selected from H, $C_{1-6}$ alkyl, $-OR^{Y1}$, $-NR^{Y1}R^{Y2}$, $-C(=O)OR^{Y1}$, $-C(=O)NR^{Y1}R^{Y2}$ and $-C(=O)R^{Y1}$, wherein the alkyl is optionally substituted with one or more substituents selected from $-OR^{Y3}$ and $-NR^{Y3}R^{Y4}$; preferably, at each occurrence, $R^{a1}$, $R^{b1}$, $R^{c1}$, $R^{a2}$, $R^{b2}$, $R^{c2}$ are each independently selected from H, $C_{1-6}$ alkyl, $-OR^{Y1}$, $-NR^{Y1}R^{Y2}$ and $-C(=O)R^{Y1}$, wherein the alkyl is optionally substituted with one or more substituents selected from $-OR^{Y3}$ and $-NR^{Y3}R^{Y4}$; more preferably, at each occurrence, $R^{a1}$, $R^{b1}$, $R^{c1}$, $R^{a2}$, $R^{b2}$, $R^{c2}$ are each independently selected from H, $C_{1-6}$ alkyl, $-OR^{Y1}$, $-NR^{Y1}R^{Y2}$ and $-C(=O)R^{Y1}$, wherein the alkyl is optionally substituted with one or more substituents selected from $-NR^{Y3}R^{Y4}$; especially preferably, at each occurrence, $R^{a1}$, $R^{b1}$, $R^{c1}$, $R^{a2}$, $R^{b2}$, $R^{c2}$ are each independently selected from H, $C_{1-3}$ alkyl, $-OH$ and p-methylbenzoyl; wherein the alkyl is optionally substituted with one or more substituents selected from $-NH_2$.

<13> Use of any one of <1> to <12> above, wherein at each occurrence, $R^{Y1}$, $R^{Y2}$, $R^{Y3}$, $R^{Y4}$ are each independently selected from H, $C_{1-6}$ alkyl, phenyl, phenyl-$C_{1-4}$ alkyl, 5- to 6-membered heteroaryl, and 5- to 6-membered heteroaryl-$C_{1-4}$ alkyl, wherein the alkyl or phenyl is optionally substituted with one or more substituents selected from halogen, $-NO_2$, $-CN$, $-OH$, $-SH$, $-NH_2$, $-COOH$ and $C_{1-6}$ alkyl; preferably, at each occurrence, $R^{Y1}$, $R^{Y2}$, $R^{Y3}$, $R^{Y4}$ are each independently selected from H, $C_{1-6}$ alkyl, phenyl and phenyl-$C_{1-4}$ alkyl, wherein the alkyl or phenyl is optionally substituted with one or more substituents selected from halogen and $C_{1-6}$ alkyl; especially preferably, at each occurrence, $R^{Y1}$, $R^{Y2}$, $R^{Y3}$, $R^{Y4}$ are each independently selected from H and p-methylphenyl.

<14> Use of any one of <1> to <13> above, wherein the compound of formula (I') is selected from:

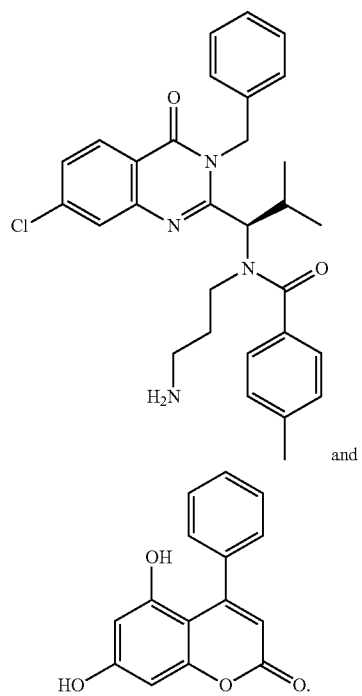

and

<15> Use of pharmaceutical composition in the preparation of a medicament for preventing or treating a polyQ-related neurodegenerative disorders; the pharmaceutical composition comprises a compound of formula (I') in any one of <1> to <14> above, or a pharmaceutically acceptable salt, stereoisomer, solvate, polymorph, tautomer, isotopic compound, metabolite or prodrug thereof, and at least one pharmaceutically acceptable carrier.

<16> Use of any one of <1> to <15> above, wherein the polyQ-related neurodegenerative disorder is selected from the group consisting of spinocerebellar ataxia type 1, spinocerebellar ataxia type 2, spinocerebellar ataxia type 3, spinocerebellar ataxia type 7, spinocerebellar ataxia type 12, spinocerebellar ataxia type 17, dentatorubral-pallidoluysian atrophy, Huntington's disease, and spinal-bulbar muscular atrophy, especially Huntington's disease and spinocerebellar ataxia type 3.

Beneficial Effect

The compound of the present invention has the effect of reducing the level of polyQ-GFP fusion protein with expanded polyQ in cells and does not reduce the level of polyQ-GFP fusion protein with shorter polyQ. Therefore, the compound of the present invention can reduce the level of polyQ protein with expanded polyQ in cells or tissues, thereby having a preventive or therapeutic effect on polyQ protein-related disorders.

The inventors further found that the compound of the present invention have an unexpected regulatory effect on mHTT levels in cells and had good safety. Administration of the compound of the present invention can improve the survival rate and climbing performance of *Drosophila* in HD model. Administration of the compound of the present invention through intraventricular or intraperitoneal injection can allele-selectively reduce the level of mHTT in the cerebral cortices and striata of HD model mice without affecting the level of wtHTT which has important physiological functions, and improved behavioral defects in mice. In the HD patient induced stem cells (iPSC) derived neurons, the compound of the present invention reduces mHTT levels, rescues disease-related phenotypes, and delays neuronal apoptosis. Therefore, the compound of the present invention has good selectivity, therapeutic effects and safety, and is easy to pass through the BBB, potentially facilitating oral administration.

In addition, the compound of the present invention can significantly reduce the level of mutant ATXN3 protein in cells, so it can be used for the treatment or prevention of spinocerebellar ataxia type 3.

Therefore, the compound of the present invention can be used to treat polyQ protein-related disorders and has the advantages of high selectivity and good safety, as well as a good prospect for development of an oral drug.

EXAMPLES

Unless otherwise specified, the instruments and reagents used herein are all commercially available.

In all statistical analyses in this article, * represents $p<0.05$;  represents $p<0.01$; * represents $p<0.001$, **** represents $p<0.0001$. For the comparison between the two groups, the statistical analysis method used is the two-tailed unpaired t test. For comparisons between three or more groups, two-tailed one-way ANOVA was applied when there is only one variable, and two-tailed two-way ANOVA was applied when there are two variables.

Abbreviation

| ATXN | ataxin | HTT | Huntingtin |
|---|---|---|---|
| TBP | TATA binding protein | ATN | atrophin |
| fl | full-length | | |
| BBB | blood-brain barrier | | |
| AR | androgen receptor | | |
| BDNF | brain derived neurotrophic factor | | |

Experimental Materials, Reagents and Method Steps
Compounds
Compound 1: ispinesib, PubChem CID: 6851740, can be purchased from Selleck, catalog number S1452;
Compound 2: PubChem CID 5398649, can be purchased from ChemDiv, catalog numberD715-2435;
Compound 3: Semaxanib, can be purchased from Selleck, CAS No. 194413-58-6;
Compound 4: Su9516, can be purchased from Selleck, CAS No. 377090-84-1;
Compound 5: can be purchased from Sinopharm Chemical Reagent Co. Ltd, CAS No. 779-30-6;
Compound 6: can be purchased from TargetMol, CAS No. 842-01-3; Compound 7: can be purchased from Chem-Div.

Antibody

The antibodies used for Western-blots, HTRF and/or immunofluorescence/immunohistochemistry are as follows: HTT antibody 2B7 (Weiss et al. Anal Biochem 2009, 395, 8-15), 4C9, ab1 (Sapp et al. J Biol Chem 2012, 287, 13487-13499) and MW1 (Ko et al. Brain research bulletin 2001, 56, 319-329) were prepared by the method of the prior art; the antibody S830 used for immunostaining to detect HTT aggregates was gifted from Dr. Gillian Bates; other antibodies were purchased from companies such as Millipore and Sigma.

Preparation and Verification of Recombinant Human Full-Length HTT Protein (1) The human HTT gene (GenBank: NM_002111.8) with $(CAG)_{23}$ or $(CAG)_{73}$ was synthesized de novo by Genewiz Inc. The human HTT gene was cloned into the modified pCAG vector (from Addgene) with N-terminal protein A tag.

(2) The plasmid was transfected into human embryonic kidney E293 cells for expression using polyethyleneimine (PEI, from Polysciences, 23966). The protein is purified with IgG monoclonal antibody-agarose (Smart-lifesciences, SA030010), digested with TEV protease to remove the protein A tag, and further purified with Mono Q and Superose 6 (5/150 GL) columns from GE healthcare. Validation is conducted using Coomassie blue staining and Western-blots.

Cells Used for Tests

Primary cultured cortical neurons: The brains of $Hdh^{Q140/Q7}$ and $Hdh^{Q7/Q7}$ newborn mice (P0) were dissected, digested, dissociated, and cultured.

Some primary patient fibroblasts and wild-type cells are from HD patients (Q47, Q55) of the Mongolian Huntington's disease family and healthy controls (WT, Q19). SCA3 cell line was from patient (Q74). The HD Q68 fibroblast cell line was from Coriell Cell Repositories (Camden, N.J., USA). Immortalized fibroblasts and induced stem cells (iPSCs) are prepared from primary fibroblasts. HEK293T cells were from ATCC.

Animals Used for Tests
Huntington's Disease Drosophila

Nervous system driver line elav-GAL4 (c155), HTT expressing lines UAS-fl-HTT-Q16 and UAS-fl-HTT-Q128 were from Bloomington Drosophila Stock Center (http://flystocks.bio.indiana.edu/) and kept in a 25° C. incubator.

Crosses were set up between virgin female Drosophilae carrying elav-GAL4 driver and the UAS-fl-HTT-Q16 or UAS-fl-HTT-Q128 male Drosophilae to generate a transgenic Drosophilae driven by elav-GAL4 to express human HTT full-length protein (Q16) or (Q128) in the nervous system.

Huntington's Disease Mice

Mice expressing wild-type HTT gene ($Hdh^{Q7/Q7}$) were from the Marian Difiglia laboratory of Massachusetts General Hospital, Harvard University. The Q140 gene knock-in heterozygous mouse ($Hdh^{Q140/Q7}$) was prepared according to the method of the prior art (Menalled et al., J Comp Neurol, 2003, 465: 11-26).

Protein Analysis

Homogeneous time-resolved fluorescence (HTRF) analysis: the cell or tissue lysate was diluted with the original lysis buffer PBS+1% (v/v) Triton X-100+1×cOmplete™ protease inhibitor to lyse the sample, then HTRF assay buffer (50 mM $NaH_2PO_4$, 400 mM NaF, 0.1% BSA, 0.05% (v/v) Tween-20, 1% (v/v) Triton X-100, pH 7.4) was used to dilute the specified antibody pair for detection. In HTRF buffer, the donor antibody concentration was 0.023 ng/µL and the acceptor antibody concentration was 1.4 ng/µL.

Determination of the amount of protein: the amount of protein was determined by the above method. Background correction was performed using blank sample. The protein concentration for all samples were determined to correct the loadings. Different protein concentrations or cell numbers per well were measured to ensure that the signals are within the linear range.

Cell Analysis

Immunofluorescence: cells were washed, fixed, permeabilized and blocked, then incubated with primary antibody overnight at 4° C., then washed three times with blocking buffer, and incubated with secondary antibody for 1 hour at room temperature, stained with DAPI, and mounted. Images were taken by Zeiss Axio Vert A1 confocal microscope. TUBB3 or co-localization was analyzed using ImageJ.

Example 1 Effects of the Compounds on the Levels of Proteins Containing Expanded Polyglutamine The inventors used HEK293T cells exogenously expressing polyQ-GFP fusion proteins (Q72-GFP or Q25-GFP) to detect compounds that can control the level of proteins containing expanded polyglutamine in the cells. The method was as follows:

(1) PolyQ-GFP cDNA sequence (expressing Met-polyQ-GFP, wherein polyQ was Q72 or Q25) was synthesized de novo and subcloned into pcDNA vector. It was transfected into HEK293T cells (ATCC, CRL-3216) through forward transfection to obtain Q72-GFP expressing cells and Q25-GFP expressing cells, respectively. And the same method was used to obtain cells expressing Q53-GFP, cells expressing Q46-GFP, and cells expressing Q38-GFP.

(2) The polyQ-GFP proteins expressed by (1) were purified separately to obtain Q72-GFP, Q53-GFP, Q46-GFP, Q38-GFP and Q25-GFP (SEQ ID NO: 1). Among them, Q72-GFP, Q53-GFP, Q46-GFP, Q38-GFP differed from the amino acid sequence of SEQ ID NO: 1 in the length of the expanded polyglutamine.

(3) The Q72-GFP expressing cells and Q25-GFP expressing cells obtained in step (1) were used. The cells were treated with 100 nM compound 1, or 50 nM compound 2 for 2 days. Then the level of polyQ-GFP was measured by Incucyte fluorescence counting (FIG. 1). It was observed that compound 1 and compound 2 effectively reduced the level of the protein containing expanded polyglutamine (Q72-GFP) in HEK293T cells, but did not reduce the level of the protein containing the shorter polyglutamine (Q25-GFP). This result indicated that the compound of the present invention can selectively reduce the level of abnormally amplified polyQ protein in cells.

Example 2 Interaction of the Compounds with Proteins Containing Expanded Polyglutamine 2.1 OI-RD Detection of the Affinity of Compounds to Proteins Containing Expanded Polyglutamine Compound chips were prepared using a contact microarray printer (SmartArrayer 136, CapitalBio Corporation) according to the prior art (Zhu et al., Sensors (Basel) 2016, 16(3), 378; Fei et al., J Biomed Opt 2010, 15(1), 016018). Each compound was printed in triplicate on the microarray. OI-RD was used to measure the affinity reaction parameters between the compounds and GFP or the polyQ-GFP protein obtained in step (2) of Example 1. These compounds did not bind to Q25-GFP or GFP, but binded to proteins with expanded polyglutamine. For example, compound 2 showed certain binding affinity to proteins with 38 or more glutamine repeats. The affinity reaction parameters are shown in Table 1.

TABLE 1

The association rate constants, dissociation rate constants, and equilibrium dissociation constants of the affinity reactions of compound 2 with Q72-GFP, Q53-GFP, Q46-GFP, and Q38-GFP

|  | $K_{on}$ (min · nM)$^{-1}$ | $K_{off}$ (min)$^{-1}$ | $K_d$ (nM) |
| --- | --- | --- | --- |
| Q72-GFP | $6.20 \times 10^{-5}$ | $1.92 \times 10^{-2}$ | 309.7 |
| Q53-GFP | $1.08 \times 10^{-4}$ | $4.65 \times 10^{-3}$ | 43.1 |
| Q46-GFP | $7.65 \times 10^{-6}$ | $2.5^7 \times 10^{-2}$ | 3359.5 |
| Q38-GFP | $2.99 \times 10^{-6}$ | $1.5 \times 10^{-2}$ | 5016.7 |

2.2 MST Detection of the Affinity of Compounds to Proteins Containing Expanded Polyglutamine Furthermore, the affinity of compound 2 with proteins containing expanded polyglutamine was detected with micro thermophoresis (MST) using Monolith NT.115 instrument from NanoTemper Technologies. The reaction buffer was 20 mM HEPES, pH 7.4, 150 mM NaCl, and protein concentration was 500 nM. Compound 2 showed no binding affinity with Q25-GFP, and its $K_d$ with Q72-GFP is 2.80 μM.

In summary, the results of OI-RD detection and MST detection indicated that the compound of the present invention selectively binded to proteins containing expanded polyglutamine.

Figure 2:
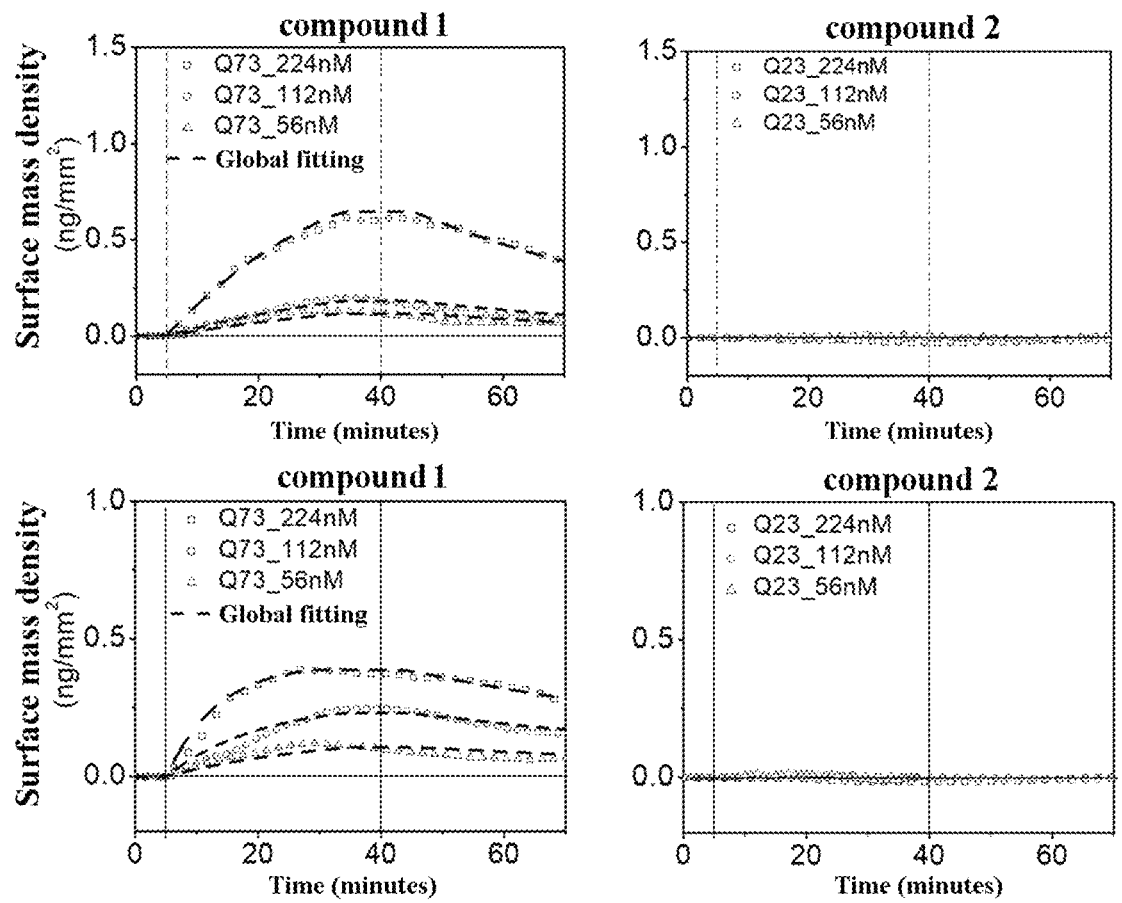
FIG. 2. Affinity binding curves determined by OI-RD of compounds with full-length HTT of different concentrations. The vertical dashed lines indicate the beginning of the association phase and the dissociation phase during the affinity binding. The dashed curve is the result of the global fitting of the Langmuir reaction model.

Example 3 Effect of the Compounds with Full-Length mHTT 3.1 OI-RD Detection of Affinity Between Compounds and Full-Length HTT Compound chips were prepared using a contact microarray printer (SmartArrayer 136, CapitalBio Corporation) according to the prior art (Zhu et al., Sensors (Basel) 2016, 16(3), 378; Fei et al., J Biomed Opt 2010, 15(1), 016018). Each compound was printed in triplicate on the microarray. OI-RD was used to measure the affinity reaction parameters of the compounds with full-length mHTT (flHTT-Q73) and full-length HTT-Q23 (flHTT-Q23, SEQ ID NO: 2) (FIG. 2). The compound showed no binding affinity with flHTT-Q23, and the association rate constants, dissociation rate constants and equilibrium dissociation constants of the affinity reactions with flHTT-Q73 are shown in Table 2.

TABLE 2

The association rate constants, dissociation rate constants and equilibrium dissociation constants of the affinity reactions of the compounds with flHTT-Q73

|  | $K_{on}$ (min · nM)$^{-1}$ | $K_{off}$ (min)$^{-1}$ | $K_d$ (nM) |
| --- | --- | --- | --- |
| compound 1 | $6.43 \times 10^{-5}$ | $2.0^7 \times 10^{-2}$ | 321.9 |
| compound 2 | $4.81 \times 10^{-4}$ | $1.19 \times 10^{-2}$ | 24.7 |

3.2 MST Detection of the Affinity of the Compound with Full-Length HTT

Figure 3:
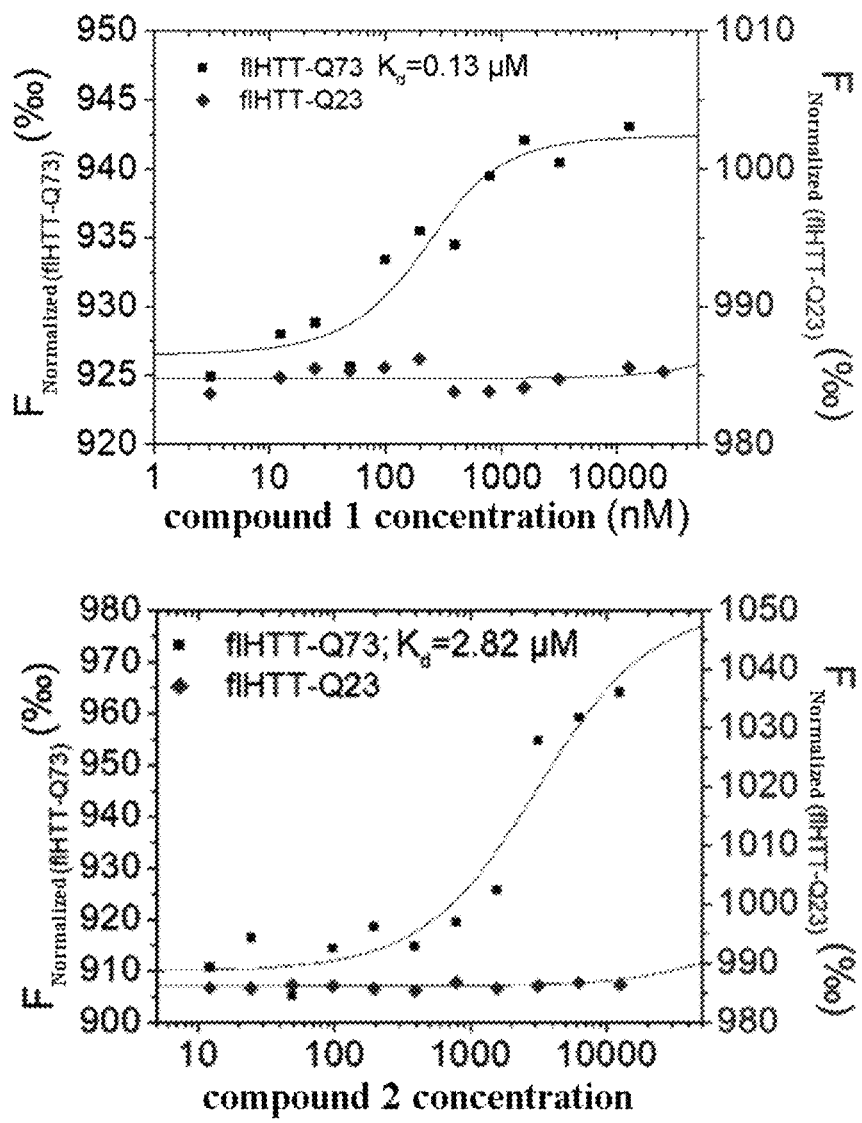
FIG. 3. Affinity binding curve determined by MST of compound with full-length HTT.

The affinity of the compounds with full-length HTT was verified with micro thermophoresis (MST) using Monolith NT.115 instrument from NanoTemper Technologies (FIG. 3). The reaction buffer was 20 mM HEPES, pH 7.4, 150 mM NaCl. Protein concentration was 500 nM. The compound of the present invention showed no binding affinity with flHTT-Q23. The $K_d$ of compound 1 and flHTT-Q73 was 0.13 μM; the $K_d$ of compound 2 and flHTT-Q73 was 2.82 μM.

In summary, the results of OI-RD measurement and MST assay both showed that the compound of the present invention selectively binded with flHTT-Q73. This conclusion was inherently consistent with the phenomenon that the compound selectively reduced protein levels containing expanded polyglutamine in HEK293T cells, indicating that the compound's effect on the above-mentioned protein levels may be achieved by selectively binding with proteins containing expanded polyglutamine.

Figure 4:
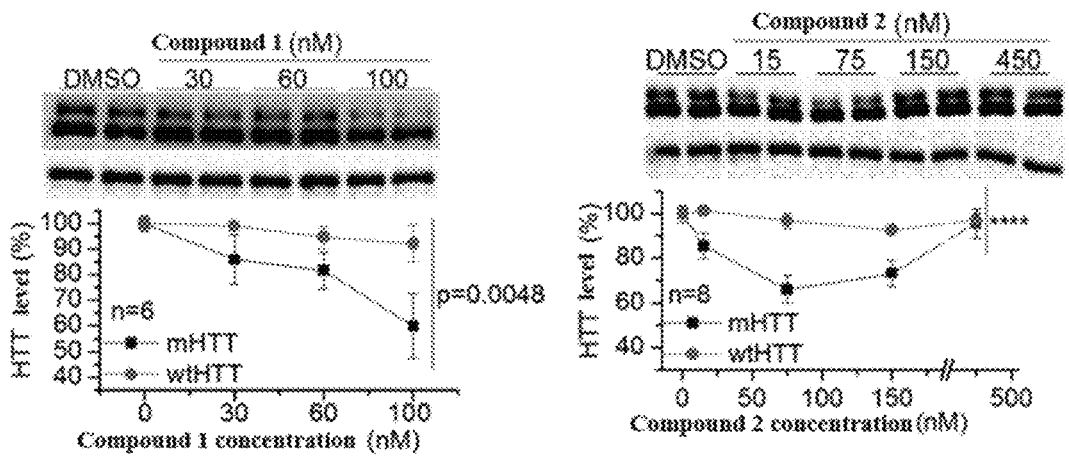
FIG. 4. Effects of compounds on HTT levels in cortical neurons of Hdh$^{Q140/Q7}$ mice.
Figure 5:
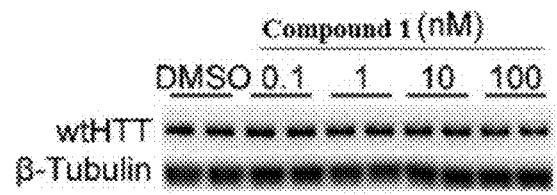
FIG. 5. Effects of compound 1 on HTT levels in cortical neurons of Hdh$^{Q7/Q7}$ mice.

Example 4 Effects of the Compounds on Cortical Neurons in HD Model Mice 4.1 Effects on mHTT and wtHTT Levels (1) The primary cultured Hdh$^{Q140/Q7}$ and Hdh$^{Q7/Q7}$ mouse cortical neuron cells were treated with the compound for 2 days. Then the levels of mHTT and wtHTT were detected by Western-blots (antibody 2166) (FIG. 4 and FIG. 5). Compound 1 and compound 2 reduced the level of mHTT in cortical neurons of Q140 knock-in heterozygous mice (Hdh$^{Q140/Q7}$), but hardly affected the level of wtHTT. Compound 1 did not reduce wtHTT levels in cortical neurons of Hdh$^{Q7/Q7}$ mice.

Figure 6:
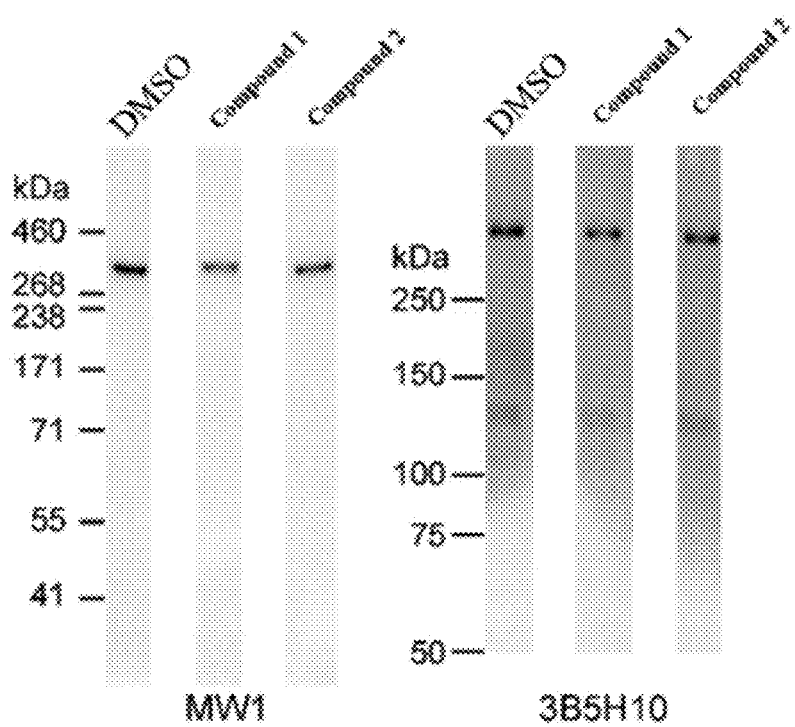
FIG. 6. Detection of N-terminal fragments of mHTT with antibodies MW1 and 3B5H10.

(2) mHTT was detected using anti-polyQ antibodies MW1 and 3B5H10, and observed for bands of proteins with smaller molecular weights. As a result, no increase in the N-terminal fragments of mHTT was observed (FIG. 6). The detected decrease in mHTT level was not due to an increase in site-specific cleavage.

4.2 Cytotoxicity Test

Figure 7:
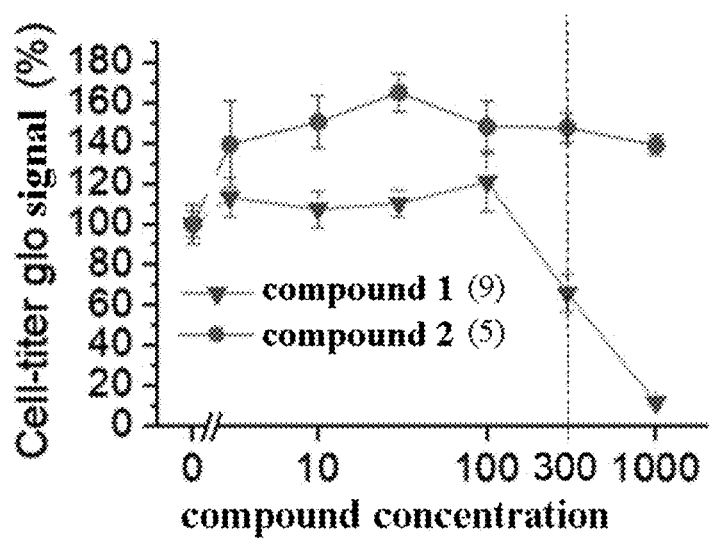
FIG. 7. Cell viability test results of Hdh$^{Q140/Q7}$ mouse cortical neurons after treatment with the compounds.

CellTiter-glo (Promega, G7570) was used according to the protocol provided in the kit to determine the viability of Hdh$^{Q140/Q7}$ mouse cortical neurons after treatment with the specified compound (FIG. 7).

The compound of the present invention showed no cytotoxicity to Hdh$^{Q140/Q7}$ mouse cortical neurons at the test concentration described in 4.1. The detected decrease in mHTT level was not due to neuronal cell loss.

In summary, the compound of the present invention allele-selectively reduced the level of mHTT in cells, and had no cytotoxicity, and had good safety.

Example 5 Effects of the Compounds on mHTT and wtHTT Levels of Huntington's Disease Patient Fibroblasts 5.1 Effect on the Levels of mHTT and wtHTT in HD Patient Primary Fibroblasts Preliminary experiments were conducted. As a result, the compound exhibited the best mHTT reduction effect at a concentration of 100 nM.

Figure 8:
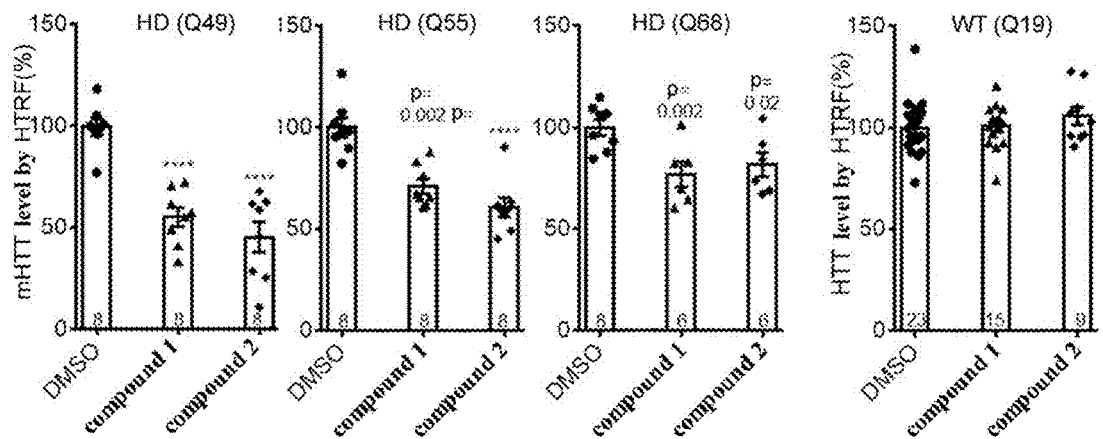
FIG. 8. Effects of compounds on mHTT levels in primary fibroblasts of HD patients at the concentration of 100 nM.

Experiment method: The fibroblasts (Q49, Q55, Q68) of HD patients were treated with 100 nM compound for 2 days. Then mHTT (antibody pair: 2B7/MW1) and total HTT (antibody pair: 2B7/2166) were detected by HTRF. The results are shown in FIG. 8. Reduced mHTT levels were observed in primary fibroblasts (Q49, Q55, Q68) of HD patients. No reduction in HTT levels was observed in wild-type primary fibroblasts.

5.2 Effects on the Level of mHTT in HD Patient Immortalized Fibroblasts

Figure 9:
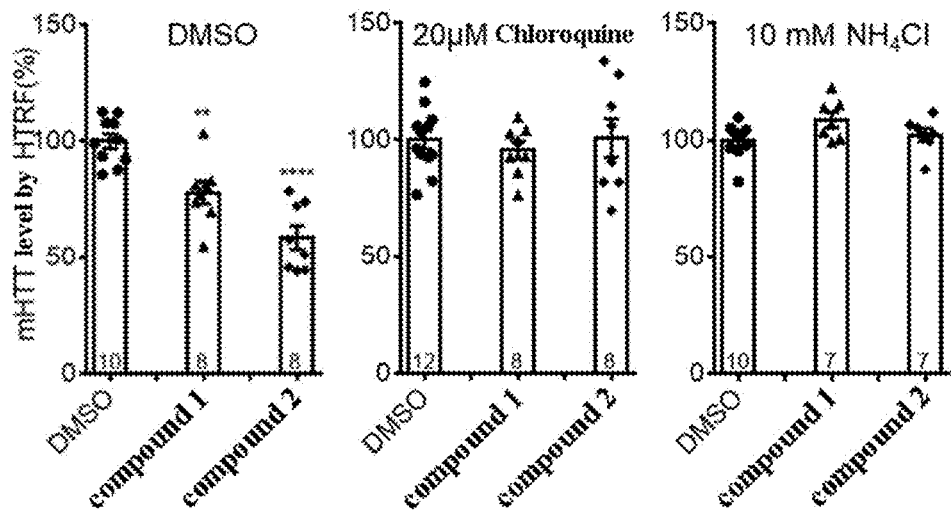
FIG. 9. Effects of compounds on mHTT levels in immortalized fibroblasts of HD patients.
Figure 10:
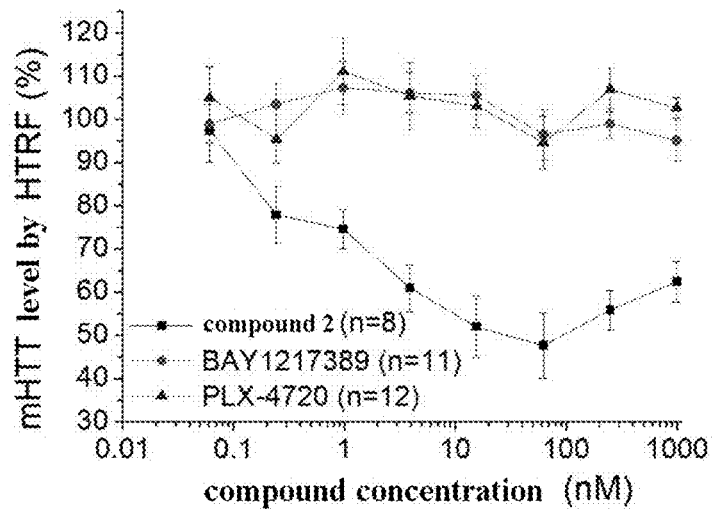
FIG. 10. Compound 2 reduces mHTT levels in immortalized fibroblasts of HD patients.

A test method similar to that described in 5.1, HTRF (antibody pair: 2B7/MW1) was used to detect the effects of the compound of the present invention on the level of mHTT in HD patient immortalized fibroblasts (FIG. 9). Decreased mHTT levels were observed on HD patient immortalized fibroblasts. FIG. 10 shows that compound 2 reduced the level of mHTT in HD patient immortalized fibroblasts at different doses.

Figure 11:
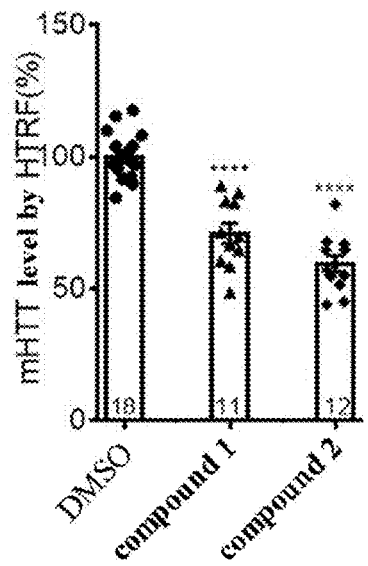
FIG. 11. Effects of compounds on mHTT levels in HD patient iPSC-derived neurons.

Example 6 Effects of the Compounds on mHTT Level and Neuronal Apoptosis of HD Patient iPSC-Derived Neurons 6.1 Effect on mHTT and wtHTT Levels
Experimental Materials:

A test method similar to that described in 5.1, HTRF (antibody pair: 2B7/MW1) was used to detect the effects of compound 1 and compound 2 on the level of mHTT in HD patient iPSC-derived neurons (Q47) (FIG. 11). Decreased mHTT levels were observed in HD patient iPSC-derived neurons.

Using the same method, the following compound 3, compound 4, compound 5, compound 6, and compound 7 were observed to reduce the mHTT level in the HD patient iPSC-derived neurons; wherein compound 3 reduced mHTT levels by approximately 12.2%, compound 4 reduced mHTT levels by approximately 24.9%, compound 5 reduced mHTT levels by approximately 26.8%, compound 6 reduced mHTT levels by approximately 24.2%, and compound 7 reduced mHTT levels by approximately 19.7%.

The compound of the present invention rescued disease-related phenotypes in HD patient iPSC-derived neurons through autophagy.

6.2 Effects on Neuronal Apoptosis
(1) Immunostaining

HD patient iPSC-derived neurons (Q47) were treated using 100 nM compound 1 or 50 nM compound 2 for 1 day. Then the cells were stressed (by BDNF removal).

Figure 12:
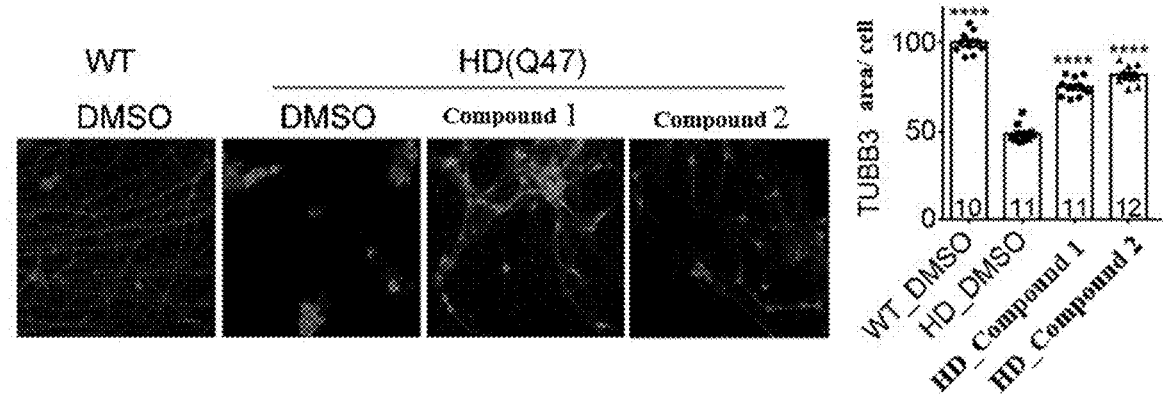
FIG. 12. Effects of compounds on the apoptosis of HD patient iPSC-derived neurons. The scale bar is 50 μm.

Neuronal specific tubulin marker TUBB3 was stained with DAPI. The TUBB3 signal covered area was normalized to the cell nuclei counts, and the data was normalized to the wild type controls to analyze neuronal apoptosis (FIG. 12).

(2) Caspase-3 Activity Detection

After removing BDNF, loss of processes and shrinkage of neurons were observed in HD neurons.

Figure 13:
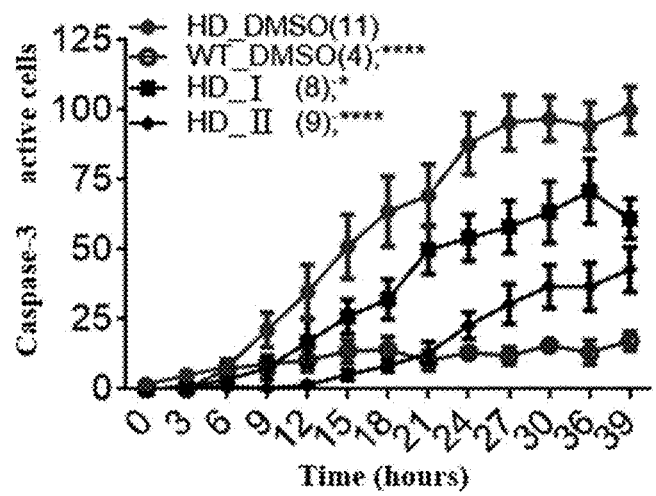
FIG. 13. Effects of compounds on the apoptosis of HD patient iPSC-derived neurons.

NucView 488 (Biotium, 30029) was used to detect active caspase-3. After removing BDNF, Incucyte (Essen Bioscience, IncuCyte FLR) was used to capture images every 3 hours in the incubator, which were analyze with Incucyte 2011A software. Three batches were tested and the results were consistent (FIG. 13). Compound 1 and compound 2 significantly improved the loss of processes and shrinkage of HD neurons after removal of BDNF.

Example 7 Effects of the Compounds on Huntington's Disease Drosophilae 7.1 Effects on mHTT Level
Experimental Method:

Q128 Drosophilae and Q16 Drosophilae were randomized into a negative control group and a positive drug group (compound 1, compound 2), with 75 drosophilae in each group. The negative control group was given the corresponding solvent DMSO, and the positive drug groups was given the corresponding positive drug.

Drosophilae were kept in standard food at 25° C. The newly hatched Drosophilae were transferred to vials with food containing the positive drug (10 μM in 400 μL DMSO) or DMSO for control. The corn food was changed every other day.

Figure 14:
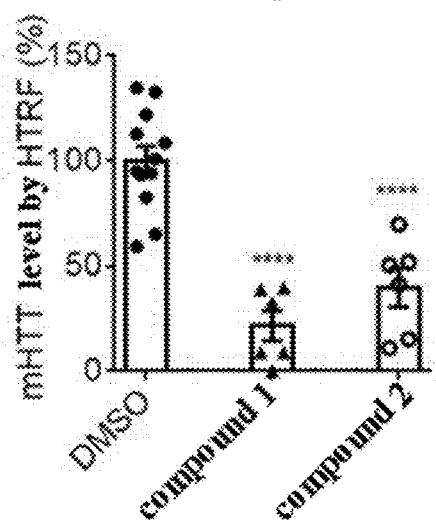
FIG. 14. Effects of compounds on mHTT levels in Huntington's disease Drosophilae.

After fed for 6 consecutive days, the *Drosophila* head protein was extracted on the 7th day. The mHTT level was measured by HTRF (antibody pair: 2B7/MW1), where each sample included head proteins from five *Drosophila* (FIG. 14). Compound 1 and compound 2 reduced mHTT levels in transgenic Drosophilae expressing human HTT full-length protein (Q128).

Figure 15:
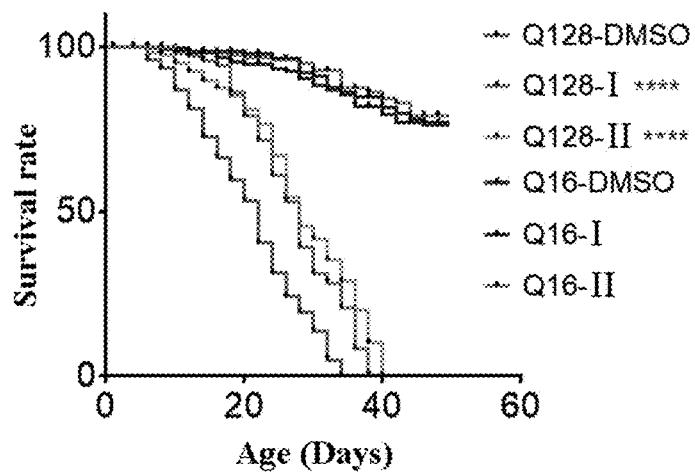
FIG. 15. Effects of compounds on the survival rate of Huntington's disease Drosophilae.

7.2 Effects of Compound on Survival Rate 75 age-matched virgin Drosophilae were put into empty plastic vials containing standard food, and the survival rate of each vial was recorded daily to measure the lifespan (FIG. 15). The survival rate of the Q128 *Drosophila* positive drug group was improved compared to the control group.

7.3 Effects on Climbing Performance 15 age-matched virgin Drosophilae was put into empty vials and tapped down so that they were at the bottom of the vials. The percentage of Drosophilae that had climbed past a 7-cm-high line after 15 seconds was recorded. The mean of five observations for each vial was plotted every day, and the data from multiple vials containing different batches of Drosophilae was plotted and analyzed.

Figure 16:
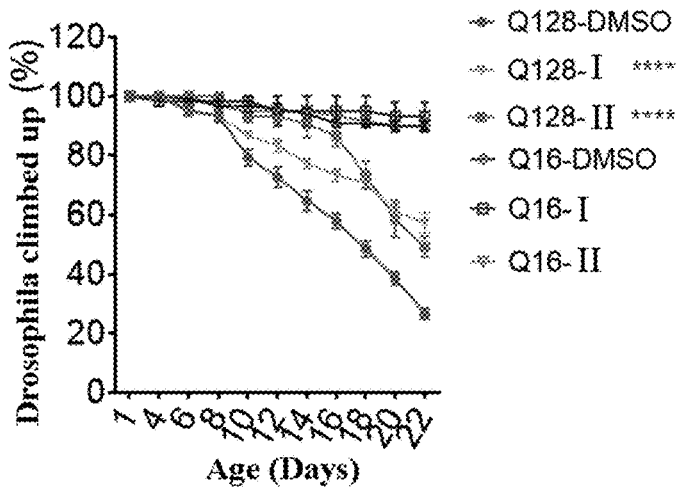
FIG. 16. Effects of compounds on the climbing performance of Huntington's disease Drosophilae.

The results are shown in FIG. 16. The number in brackets indicates the number of tested vials. The Q128 *Drosophila* positive drug group showed improved the climbing performance compared to the control group.

In the above experiments in 7.2 and 7.3, no compound was observed to have an effect on Q16 Drosophilae.

Example 8 Effects of the Compounds on HD Model Mice

Experimental animal: The mice were grouped and housed in individually vented cages with a 12-hour light/dark cycle, with a maximum of 5 adult mice per cage.

8.1 Effects of Intracerebroventricular Injection of Compounds on the Levels of mHTT and wtHTT in the Cortices of HD Mice Experimental animals: Hdh$^{Q140/Q7}$ mice (3 months old), 4 in each group.

Experimental method: one icy-injection was conducted per day using 2 μL artificial cerebrospinal fluid (ACSF: 1 mM glucose, 119 mM NaCl, 2.5 mM KCl, 1.3 mM MgSO$_4$, 2.5 mM CaCl$_2$, 26.2 mM, NaHCO$_3$, 1 mM NaH$_2$PO$_4$)

containing a compound at a concentration of 25 µM. 2 µL ACSF containing the same amount of DMSO was used as a control.

Figure 17:
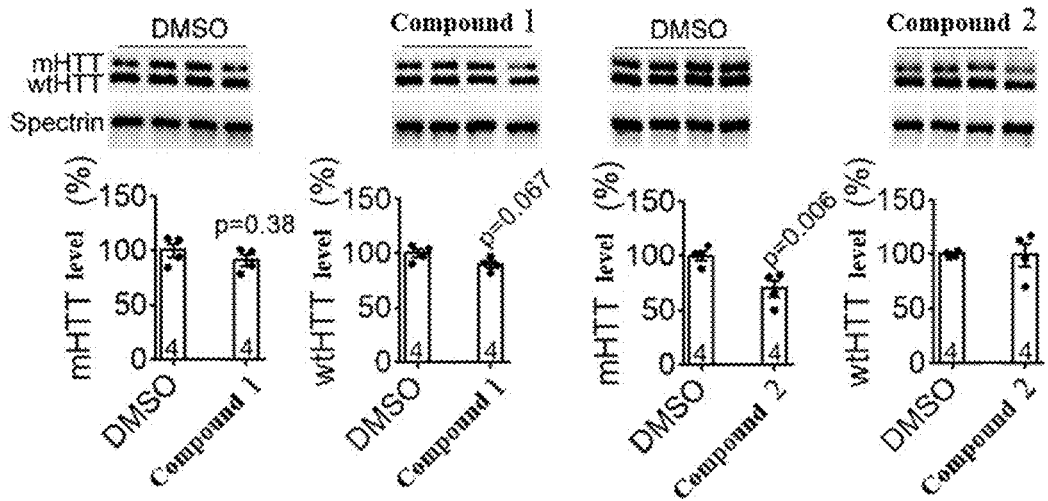
FIG. 17. Effects of intracerebroventricular injection of compounds on the levels of mHTT and wtHTT in the cortices of Huntington's disease mice.

After 10 days of injection, the brain cortical neuron proteins of the mice were extracted, and the levels of mHTT and wtHTT were detected by Western-blots (antibody 2166). Each test includes three repetitions for each sample, and the mean values was calculated (FIG. 17). Compound 2 significantly reduced mHTT level in Hdh$^{Q140/Q7}$ mouse cortices and showed mHTT selectivity relative to wtHTT.

8.2 Compound 2 Administered by Intraperitoneal Injection

Experimental method: The compound or control DMSO was diluted with 0.9% NaCl intravenous infusion solution to 0.05 µg/µL. One ip-injection (0.5 mg/kg) was conducted per day. After 14 days of injection, tissue extraction or behavioral experiment were conducted.

In vivo compound detection in brain tissues of ip-injected mice: 2 hours after ip-injection of DMSO or compound in mice, the brain was dissected, weighed, and the compound in the brain tissue was extracted, analyzed with UPLC-MS (Acquity Ultra Performance Liquid Chromatography System, Acquity UPLC BEH C18 (1.7 µm, 2.1×50 mm) column and Xevo TQ-S mass spectrometer, Waters Corporation, Milford, MA, USA) for LC-MS/MS analysis. The level of compound 2 reached the brain tissue was 9.48 ng/g. No mass spectrum signal of compound was observed for the control (DMSO) group. The compound of the present invention can be delivered to the brain of mice through the BBB smoothly, which potentially facilitates oral administration of the compound.

8.3 Effects of Intraperitoneal Injection of Compounds on the Levels of mHTT and wtHTT in the Cortices and Striata of HD Mice (1) 13 Hdh$^{Q140/Q7}$ mice (5 months old) were randomized into 2 groups.

Figure 18:
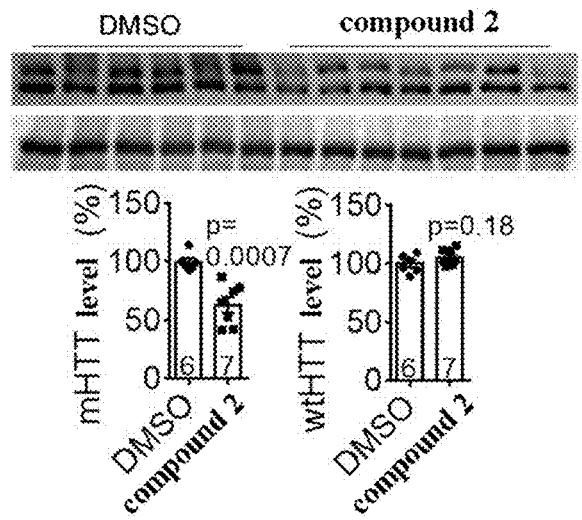
FIG. 18. Effects of intraperitoneal injection of compound 2 on the levels of mHTT and wtHTT in the cortices of Huntington's disease mice.

Administer compound 2 as described in 8.2. One ip-injection was conducted per day. After 14 days of injection, the protein was extracted and the levels of mHTT and wtHTT in the cortices of HD mice were detected by Western-blots (FIG. 18).

Figure 19:
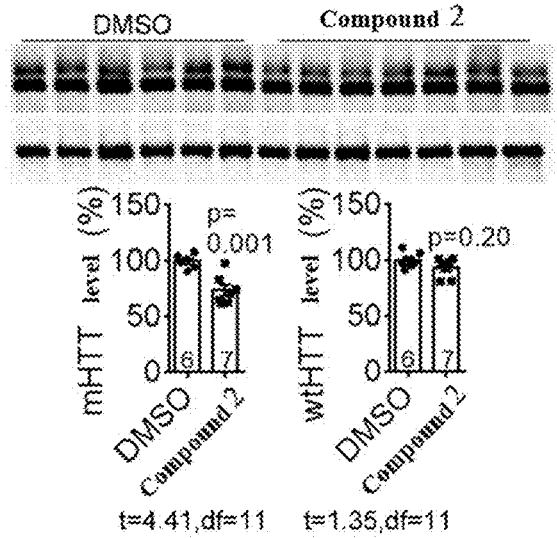
FIG. 19. Effects of intraperitoneal injection of compound 2 on the levels of mHTT and wtHTT in the striata of Huntington's disease mice.

(2) A total of 13 mice Hdh$^{Q140/Q7}$ mice (10 months old) were used, 6-7 mice in each group. According to the above method, the mouse brain striatum neuronal protein was extracted and the levels of mHTT and wtHTT were detected by Western-blots (FIG. 19).

Figure 20:
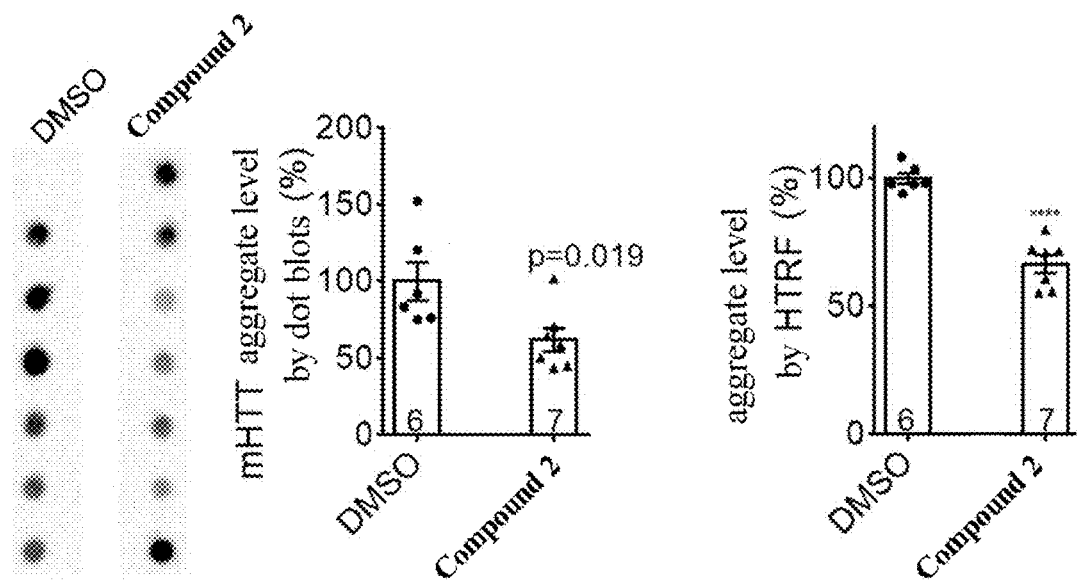
FIG. 20. Detection of mHTT aggregates in the cortices of Huntington's disease mice after intraperitoneal injection of compound 2.

(3) mHTT aggregates in the cortices of Hdh$^{Q140/Q7}$ mice were detected by dot-blot experiment (antibody: 4C9, bar plot showing the results of two repetitions) and HTRF (antibody pair: 4C9/4C$_9$). Sampling was repeated for each mouse two to three times on average (FIG. 20). No increase in mHTT aggregates was observed. The decrease in mHTT levels in the compound 2 treated group was not due to changes in mHTT solubility.

In summary, intraperitoneal injection of compound 2 reduced the levels of mHTT in the cortices and striata of Hdh$^{Q140/Q7}$ mice, and showed mHTT selectivity relative to wtHTT. Therefore, compound 2 had the prospect of being developed to an oral drug.

8.4 Effects of Intraperitoneal Injection of Compound 2 on Behavioral Defects in HD Mice Experimental animals: 32 Hdh$^{Q140/Q7}$ mice were randomized into 2 groups; 28 (Hdh$^{Q7/Q7}$) mice were randomized into 2 groups.

Experimental method: administer compound 2 according to the procedure described in 8.2. One ip-injection was conducted per day, and behavioral experiments were conducted after 14 days of injection.

All behavioral experiments were carried out during the light phase. Before starting the experiments, all mice were kept in the behavioral test room under dim red light for one hour.

Figure 21:
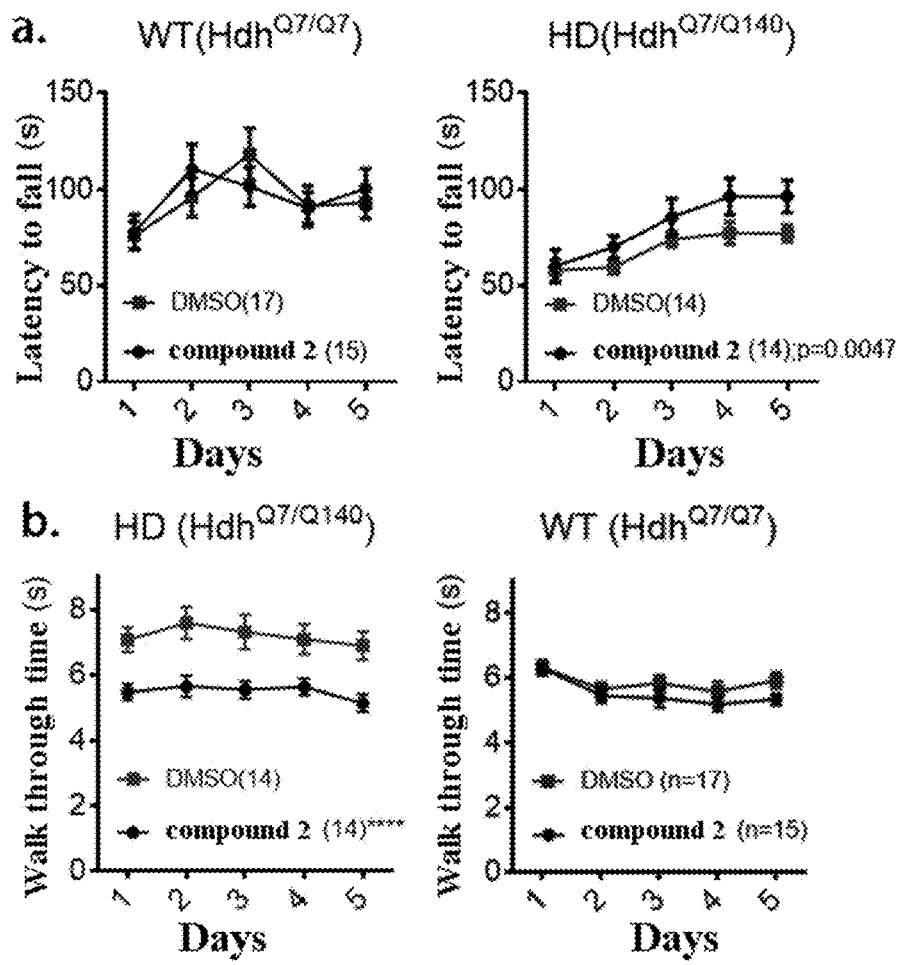
FIG. 21. Effects of intraperitoneal injection of compound 2 on behavioral defects in Huntington's disease mice.

Rotarod test: The mice were pre-trained for 3 consecutive days (on the rotarod rotating at 4 rpm for 2 minutes). The result of each experiment was recorded as time on the rod (time on the rotating rod), until falling from the rod or until the end of the task. Each test include three repetitions with an inter-trial interval of 60 min in order to reduce stress and fatigue. The means of three trials were analyzed for each mouse (FIG. 21a).

Balance beam test: a 2 cm thick meter stick with a total length of 100 cm was suspended on the platform on both sides. There was a bright light at the starting point and a dark box with food at the endpoint. The total time for each mouse to walk through the balance beam was recorded (FIG. 21b).

The compound of the present invention improved the Huntington's disease related behavioral defects in HD model mice, and had no effect on wild-type mice.

Example 9 Effects of the Compounds and the ATXN3 with Abnormally Expanded polyQ 9.1 Preparation of Recombinant Human MBP-ATXN3

(1) His8 tag and TEV protease cleavage site is added in pMal-C2x plasmid (from New England Biolabs) to prepare prokaryotic expression vector pMBP. The ATXN3 gene (GenBank: NM_001127696.2) is edited to control the length of the expanded polyglutamine, the gene is amplified and cloned into the prepared pMBP to obtain the pMBP-ATXN3-Q28 and pMBP-ATXN3-Q68 plasmids with polyQ repeated 28 and 68 times, respectively.

(2) The expression plasmids pMBP-ATXN3-Q28 and pMBP-ATXN3-Q68 were introduced into *Escherichia coli* Rosetta(DE3)pLsyS for expression. Preliminary purification was conducted with HisTrap HP column (GE Healthcare, 17524701). The product was concentrated by ultrafiltration and then further purified with Superose 6 Increase 10/300 GL size exclusion column (GE Healthcare).

(3) As verified by SDS-PAGE, the purity of the prepared human MBP-ATXN3-Q28 and MBP-ATXN3-Q68 exceeds 98%.

9.2 MST Detection of the Affinity of the Compound to ATXN3 with Abnormally Expanded polyQ Following the method in 2.2, the affinity of compound 2 with MBP-ATXN3-Q28 and MBP-ATXN3-Q68 protein was verified by microscale thermophoresis.

The results showed that compound 2 did not bind with normal ATXN3 protein (MBP-ATXN3-Q28), and the $K_d$ of compound 2 with abnormal ATXN3 protein (MBP-ATXN3-Q68) was 2.77 µM. The compound of the present invention selectively binded to ATXN3 with abnormally expanded polyQ.

Example 10 Effects of the Compounds on ATXN3 Level in Fibroblasts of Patients with Spinocerebellar Ataxia Type 3

Figure 22:
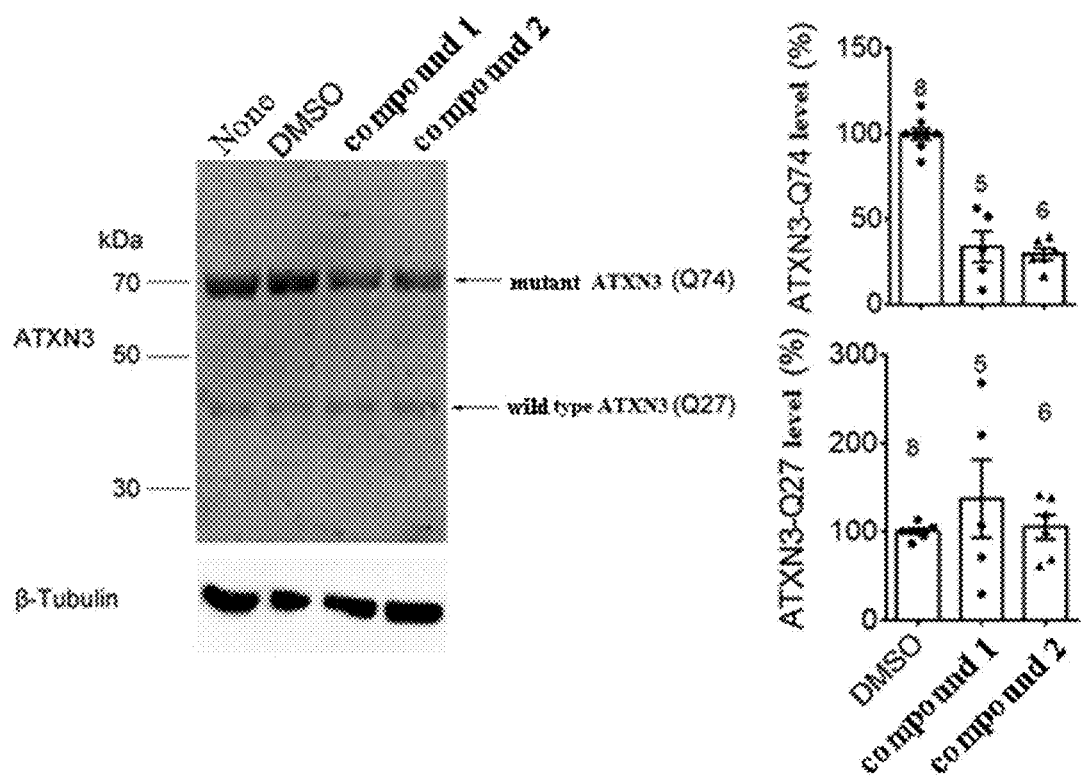
FIG. 22. Effects of compounds on the level of ATXN3 protein in fibroblasts of patients with spinocerebellar ataxia type 3.

SCA3 patient fibroblasts (Q74), wild-type cells (Q27) were treated with 100 nM compound 1 or 50 nM compound 2 for 2 days. Then the levels of mutant ATXN3 protein (ATXN3-Q74, SEQ ID NO: 3) and wild-type ATXN3 protein (ATXN3-Q27, SEQ ID NO: 4) were determined by Western-blots (FIG. 22). A decrease in mutant ATXN3 protein level was observed on SCA3 patient fibroblasts (Q74), but no decrease in wild-type ATXN3 protein level was observed. Therefore, the compound can be used to treat SCA3.

Example 11 Effects of the Compounds on the Level of ATXN1 with Abnormally Expanded polyQ in Cells (1) PolyQ-ATXN1 cDNA (where polyQ is Q92) was synthesized de novo and subcloned into pcDNA vector. It transfected into HEK293T cells (ATCC, CRL-3216) to obtain cells expressing His-ATXN1-Q92.

Figure 23:
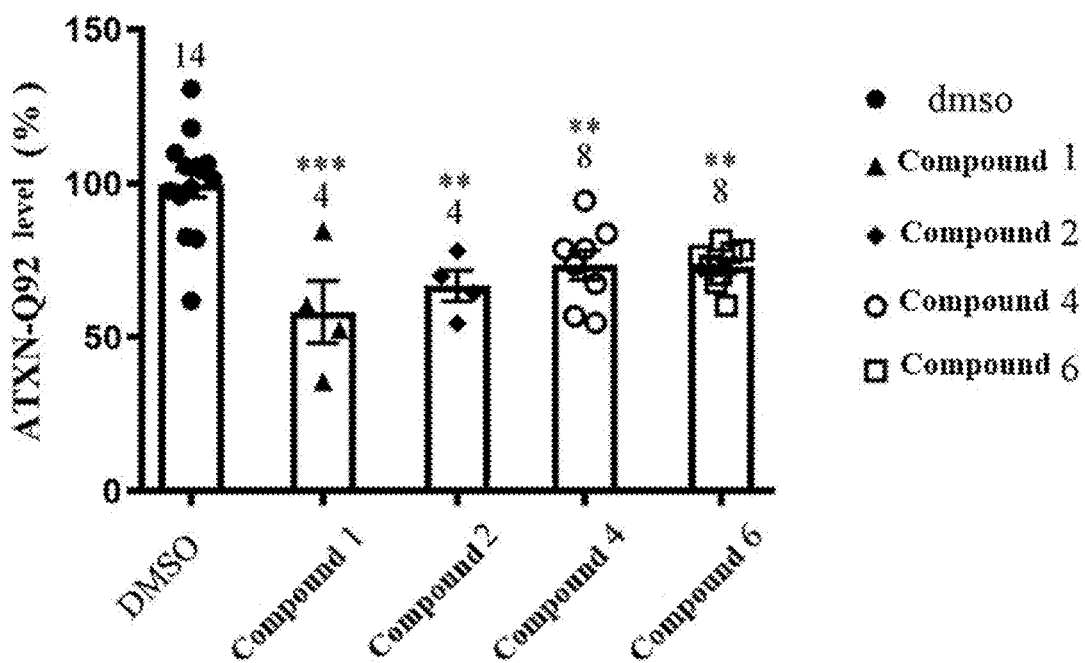
FIG. 23. Effects of compounds on the level of mutant ATXN1 protein in HEK293T cells.

(2) Cells prepared in (1) were treated with 100 nM compound (compound 1, or compound 2, or compound 4, or compound 6) for 2 days. Then the level of mutant ATXN1 protein (His-ATXN1-Q92, SEQ ID NO: 5 with His tag at the N-terminal) was detected by HTRF (antibody pair: anti-His-Tb/MW1-D2, FIG. 23). Decreased levels of mutant ATXN1 were observed on fibroblasts (Q92) of SCA1 patients. Therefore, the compound of the present invention can be used to treat or prevent spinocerebellar ataxia type 1.

```
Sequence Listing
Q25-GFP:
                                                          [SEQ ID NO: 1]
MQQQQQQQQQQQQQQQQQQQQQQQQQQQMSKGEELFTGVVPILVELDGDVNGH

KFSVRGEGEGDATNGKLTLKFICTTGKLPVPWPTLVTTLTYGVQCFSRYPDHMKRHD

FFKSAMPEGYVQERTISFKDDGTYKTRAEVKFEGDTLVNRIELKGIDFKEDGNILGHK

LEYNFNSHNVYITADKQKNGIKANFKIRHNVEDGSVQLADHYQQNTPIGDGPVLLPD

NHYLSTQSVLSKDPNEKRDHMVLLEFVTAAGITHGGSG

HTT-Q23:
                                                          [SEQ ID NO: 2]
MATLEKLMKAFESLKSFQQQQQQQQQQQQQQQQQQQQQQQPPPPPPPPPPPQLPQPP

PQAQPLLPQPQPPPPPPPPPPGPAVAEEPLHRPKKELSATKKDRVNHCLTICENIVAQSV

RNSPEFQKLLGIAMELFLLCSDDAESDVRMVADECLNKVIKALMDSNLPRLQELELYK

EIKKNGAPRSLRAALWRFAELAHLVRPQKCRPYLVNLLPCLTRTSKRPEESVQETLAA

AVPKIMASFGNFANDNEIKVLLKAFIANLKSSSPTIRRTAAGSAVSICQHSRRTQYFYS

WLLNVLLGLLVPVEDEHSTLLILGVLLTLRYLVPLLQQQVKDTSLKGSFGVTRKEMEV

SPSAEQLVQVYELTLHHTQHQDHNVVTGALELLQQLFRTPPPELLQTLTAVGGIGQLT

AAKEESGGRSRSGSIVELIAGGGSSCSPVLSRKQKGKVLLGEEEALEDDSESRSDVSSS

ALTASVKDEISGELAASSGVSTPGSAGHDIITEQPRSQHTLQADSVDLASCDLTSSATD

GDEEDILSHSSSQVSAVPSDPAMDLNDGTQASSPISDSSQTTTEGPDSAVTPSDSSEIVL

DGTDNQYLGLQIGQPQDEDEEATGILPDEASEAFRNSSMALQQAHLLKNMSHCRQPS

DSSVDKFVLRDEATEPGDQENKPCRIKGDIGQSTDDDSAPLVHCVRLLSASFLLTGGK

NVLVPDRDVRVSVKALALSCVGAAVALHPESFFSKLYKVPLDTTEYPEEQYVSDILNY

IDHGDPQVRGATAILCGTLICSILSRSRFHVGDWMGTIRTLTGNTFSLADCIPLLRKTLK

DESSVTCKLACTAVRNCVMSLCSSSYSELGLQLIIDVLTLRNSSYWLVRTELLETLAEI

DFRLVSFLEAKAENLHRGAHHYTGLLKLQERVLNNVVIHLLGDEDPRVRHVAAASLI

RLVPKLFYKCDQGQADPVVAVARDQSSVYLKLLMHETQPPSHFSVSTITRIYRGYNLL

PSITDVTMENNLSRVIAAVSHELITSTTRALTFGCCEALCLLSTAFPVCIWSLGWHCGV

PPLSASDESRKSCTVGMATMILTLLSSAWFPLDLSAHQDALILAGNLLAASAPKSLRSS

WASEEEANPAATKQEEVWPALGDRALVPMVEQLFSHLLKVINICAHVLDDVAPGPAIK

AALPSLTNPPSLSPIRRKGKEKEPGEQASVPLSPKKGSEASAASRQSDTSGPVTTSKSSS

LGSFYHLPSYLKLHDVLKATHANYKVTLDLQNSTEKFGGFLRSALDVLSQILELATLQ

DIGKCVEEILGYLKSCFSREPMMATVCVQQLLKTLFGTNLASQFDGLSSNPSKSQGRA

QRLGSSSVRPGLYHYCFMAPYTHFTQALADASLRNMVQAEQENDTSGWFDVLQKVS

TQLKTNLTSVTKNRADKNAIHNHIRLFEPLVIKALKQYTTTTCVQLQKQVLDLLAQLV

QLRVNYCLLDSDQVFIGFVLKQFEYIEVGQFRESEAIIPNIFFFLVLLSYERYHSKQIIGIP
```

-continued

```
KIIQLCDGIMASGRKAVTHAIPALQPIVHDLFVLRGTNKADAGKELETQKEVVVSMLL

RLIQYHQVLEMFILVLQQCHKENEDKWKRLSRQIADIILPMLAKQQMHIDSHEALGV

LNTLFEILAPSSLRPVDMLLRSMFVTPNTMASVSTVQLWISGILAILRVLISQSTEDIVL

SRIQELSFSPYLISCTVINRLRDGDSTSTLEEHSEGKQIKNLPEETFSRFLLQLVGILLEDI

VTKQLKVEMSEQQHTFYCQELGTLLMCLIHIFKSGMFRRITAAATRLFRSDGCGGSFY

TLDSLNLRARSMITTHPALVLLWCQILLLVNHTDYRWWAEVQQTPKRHSLSSTKLLSP

QMSGEEEDSDLAAKLGMCNREIVRRGALILFCDYVCQNLHDSEHLTWLIVNHIQDLIS

LSHEPPVQDFISAVHRNSAASGLFIQAIQSRCENLSTPTMLKKTLQCLEGIHLSQSGAVL

TLYVDRLLCTPFRVLARMVDILACRRVEMLLAANLQSSMAQLPMEELNRIQEYLQSS

GLAQRHQRLYSLLDRFRLSTMQDSLSPSPPVSSHPLDGDGHVSLETVSPDKDWYVHL

VKSQCWTRSDSALLEGAELVNRIPAEDMNAFMMNSEFNLSLLAPCLSLGMSEISGGQ

KSALFEAAREVTLARVSGTVQQLPAVHHVFQPELPAEPAAYWSKLNDLFGDAALYQS

LPTLARALAQYLVVVSKLPSHLHLPPEKEKDIVKFVVATLEALSWHLIHEQIPLSLDLQ

AGLDCCCLALQLPGLWSVVSSTEFVTHACSLIYCVHFILEAVAVQPGEQLLSPERRTNT

PKAISEEEEEVDPNTQNPKYITAACEMVAEMVESLQSVLALGHKRNSGVPAFLTPLLR

NIIISLARLPLVNSYTRVPPLVWKLGWSPKPGGDFGTAFPEIPVEFLQEKEVFKEFIYRIN

TLGWTSRTQFEETWATLLGVLVTQPLVMEQEESPPEEDTERTQINVLAVQAITSLVLSA

MTVPVAGNPAVSCLEQQPRNKPLKALDTRFGRKLSIIRGIVEQEIQAMVSKRENIATHH

LYQAWDPVPSLSPATTGALISHEKLLLQINPERELGSMSYKLGQVSIHSVWLGNSITPL

REEEWDEEEEEEADAPAPSSPPTSPVNSRKHRAGVDIHSCSQFLLELYSRWILPSSSAR

RTPAILISEVVRSLLVVSDLFTERNQFELMYVTLTELRRVHPSEDEILAQYLVPATCKAA

AVLGMDKAVAEPVSRLLESTLRSSHLPSRVGALHGVLYVLECDLLDDTAKQLIPVISD

YLLSNLKGIAHCVNIHSQQHVLVMCATAFYLIENYPLDVGPEFSASIIQMCGVMLSGS

EESTPSIIYHCALRGLERLLLSEQLSRLDAESLVKLSVDRVNVHSPHRAMAALGLMLT

CMYTGKEKVSPGRTSDPNPAAPDSESVIVAMERVSVLFDRIRKGFPCEARVVARILPQF

LDDFFPPQDIMNKVIGEFLSNQQPYPQFMATVVYKVFQTLHSTGQSSMVRDWVMLSL

SNFTQRAPVAMATWSLSCFFVSASTSPWVAAILPHVISRMGKLEQVDVNLFCLVATDF

YRHQIEEELDRRAFQSVLEVVAAPGSPYHRLLTCLRNVHKVTTC

ATXN3-Q74:
                                              [SEQ ID NO: 3]
MESIFHEKQEGSLCAQHCLNNLLQGEYFSPVELSSIAHQLDEEERMRMAEGGVTSED

YRTFLQQPSGNMDDSGFFSIQVISNALKVWGLELILFNSPEYQRLRIDPINERSFICNYK

EHWFTVRKLGKQWFNLNSLLTGPELISDTYLALFLAQLQQEGYSIFVVKGDLPDCEA

DQLLQMIRVQQMHRPKLIGEELAQLKEQRVHKTDLERMLEANDGSGMLDEDEEDLQ

RALALSRQEIDMEDEEADLRRAIQLSMQGSSRNISQDMTQTSGTNLTSEELRKRREAY

FEKQQQKQQQQQQQQQQQQQQQQQQQQQQQQQQQQQQQQQQQQQQQQQQQ

QQQQQQQQQQQQQQQQQQQQQQQQQRDLSGQSSHPCERPATSSGALGSDLG

KACSPFIMFATFTLYLT

ATXN3-Q27:
                                              [SEQ ID NO: 4]
MESIFHEKQEGSLCAQHCLNNLLQGEYFSPVELSSIAHQLDEEERMRMAEGGVTSED

YRTFLQQPSGNMDDSGFFSIQVISNALKVWGLELILFNSPEYQRLRIDPINERSFICNYK

EHWFTVRKLGKQWFNLNSLLTGPELISDTYLALFLAQLQQEGYSIFVVKGDLPDCEA
```

-continued

DQLLQMIRVQQMHRPKLIGEELAQLKEQRVHKTDLERMLEANDGSGMLDEDEEDLQ

RALALSRQEIDMEDEEADLRRAIQLSMQGSSRNISQDMTQTSGTNLTSEELRKRREAY

FEKQQQKQQQQQQQQQQQQQQQQQQQQQQQQQQRDLSGQSSHPCERPATSSGAL

GSDLGKACSPFIMFATFTLYLT

ATXN1-Q92:

[SEQ ID NO: 5]

MKSNQERSNECLPPKKREIPATSRSSEEKAPTLPSDNHRVEGTAWLPGNPGGRGH

GGGRHGPAGTSVELGLQQGIGLHKALSTGLDYSPPSAPRSVPVATTLPAAYATPQPGTP

VSPVQYAHLPHTFQFIGSSQYSGTYASFIPSQLIPPTANPVTSAVASAAGATTPSQRSQLE

AYSTLLANMGSLSQTPGHKAEQQQQQQQQQQQQQQQQQQQQQQQQQQQQQQQQ

QQQQQQQQQQQQQQQQQQQQQQQQQQQQQQQQQQQQQQQQQQQQQQQQQQQ

QQQQQQQHQHQQQQQQQQQQQQQHLSRAPGLITPGSPPPAQQNQYVHISSSPQNT

GRTASPPAIPVHLHPHQTMIPHTLTLGPPSQVVMQYADSGSHFVPREATKKAESSRLQQ

AIQAKEVLNGEMEKSRRYGAPSSADLGLGKAGGKSVPHPYESRHVVVHPSPSDYSSR

DPSGVRASVMVLPNSNTPAADLEVQQATHREASPSTLNDKSGLHLGKPGHRSYALSP

HTVIQTTHSASEPLPVGLPATAFYAGTQPPVIGYLSGQQQAITYAGSLPQHLVIPGTQPL

LIPVGSTDMEASGAAPAIVTSSPQFAAVPHTFVTTALPKSENFNPEALVTQAAYPAMVQ

AQIHLPVVQSVASPAAAPPTLPPYFMKGSIIQLANGELKKVEDLKTEDFIQSAEISNDL

KIDSSTVERIEDSHSPGVAVIQFAVGEHRAQVSVEVLVEYPFFVFGQGWSSCCPERTSQ

LFDLPCSKLSVGDVCISLTLKNLKNGSVKKGQPVDPASVLLKHSKADGLAGSRHRYA

EQENGINQGSAQMLSENGELKFPEKMGLPAAPFLTKIEPSKPAATRKRRWSAPESRKL

EKSEDEPPLTLPKPSLIPQEVKICIEGRSNVGK

---

What is claimed is:

1. A method for treating a polyQ-related neurodegenerative disorder in a subject, the method comprising administering an effective amount of a compound or a pharmaceutically acceptable salt thereof to the subject, wherein
the polyQ-related neurodegenerative disorder is Huntington's disease; and
the compound is selected from:

(compound 2)
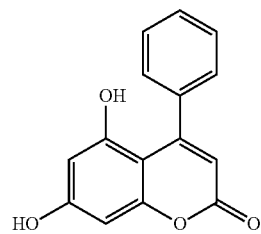

(compound 5)
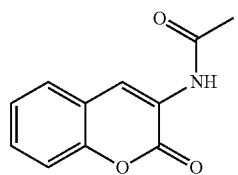

(compound 6)
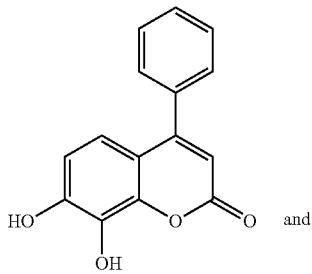
and (compound 7)
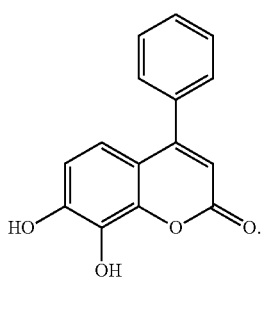

2. The method of claim 1, wherein the compound or the pharmaceutically acceptable salt thereof is administerd in a pharmaceutical composition, and the pharmaceutical composition comprises the compound or the pharmaceutically acceptable salt and at least one pharmaceutically acceptable carrier.

3. A method for treating a polyQ-related neurodegenerative disorder in a subject, the method comprising administering an effective amount of a compound, or a pharmaceutically acceptable salt thereof, to the subject, wherein
the polyQ-related neurodegenerative disorder is spinocerebellar ataxia type 1; and
the compound is selected from:

(compound 2)

(compound 6)
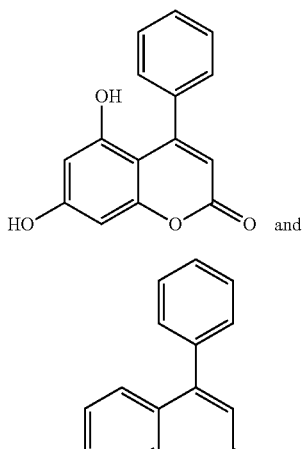
and

4. The method of claim 3, wherein the compound or the pharmaceutically acceptable salt thereof is administered in a pharmaceutical composition, and the pharmaceutical composition comprises the compound or the pharmaceutically acceptable salt and at least one pharmaceutically acceptable carrier.

5. A method for treating a polyQ-related neurodegenerative disorder in a subject, the method comprising administering an effective amount of a compound, or a pharmaceutically acceptable salt thereof, to the subject, wherein
the polyQ-related neurodegenerative disorder is spinocerebellar ataxia type 3; and
the compound is:

(compound 2)
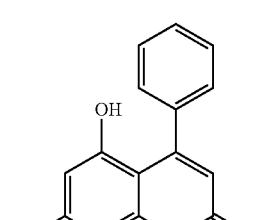

6. The method of claim 5, wherein the compound or the pharmaceutically acceptable salt thereof is administered in a pharmaceutical composition, and the pharmaceutical composition comprises the compound or the pharmaceutically acceptable salt and at least one pharmaceutically acceptable carrier.

* * * * *